United States Patent
Sagi et al.

(10) Patent No.: US 10,610,588 B2
(45) Date of Patent: Apr. 7, 2020

(54) METHODS OF PREVENTING SECONDARY INFECTIONS

(71) Applicant: Yeda Research and Development Co. Ltd., Rehovot (IL)

(72) Inventors: Irit Sagi, Rehovot (IL); Dalit Talmi-Frank, Rehovot (IL); Inna Solomonov, Rehovot (IL); Ido Amit, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 15/549,161

(22) PCT Filed: Feb. 9, 2016

(86) PCT No.: PCT/IL2016/050156
§ 371 (c)(1),
(2) Date: Aug. 6, 2017

(87) PCT Pub. No.: WO2016/128975
PCT Pub. Date: Aug. 18, 2016

(65) Prior Publication Data
US 2018/0028650 A1 Feb. 1, 2018

Related U.S. Application Data

(60) Provisional application No. 62/113,551, filed on Feb. 9, 2015.

(51) Int. Cl.
| | | |
|---|---|---|
| A61K 31/351 | (2006.01) | |
| A61K 39/395 | (2006.01) | |
| A61K 31/215 | (2006.01) | |
| C07K 16/40 | (2006.01) | |
| A61K 45/06 | (2006.01) | |
| A61K 31/196 | (2006.01) | |
| A61K 39/00 | (2006.01) | |

(52) U.S. Cl.
CPC ........ A61K 39/3955 (2013.01); A61K 31/196 (2013.01); A61K 31/215 (2013.01); A61K 31/351 (2013.01); A61K 45/06 (2013.01); C07K 16/40 (2013.01); A61K 2039/505 (2013.01)

(58) Field of Classification Search
CPC .. Y02A 90/24; Y02A 90/26; A61K 2039/505; C07K 16/40; C12N 9/6491
See application file for complete search history.

(56) References Cited

U.S. PATENT DOCUMENTS

2003/0036560 A1  2/2003  Sonis et al.

FOREIGN PATENT DOCUMENTS

| WO | WO 2004/064728 | 8/2004 |
|---|---|---|
| WO | WO 2004/103364 | 12/2004 |
| WO | WO 2015/031654 | 3/2015 |
| WO | WO 2016/128975 | 8/2016 |

OTHER PUBLICATIONS

International Preliminary Report on Patentability dated Aug. 24, 2017 From the International Bureau of WIPO Re. Application No. PCT/2016/050156. (9 Pages).
International Search Report and the Written Opinion dated Apr. 14, 2016 From the International Searching Authority Re. Application No. PCT/IL2016/050156.
Abdulkhalek et al. "Neu1 Sialidase and Matrix Metalloproteinase-9 Cross-Talk Is Essential for Toll-Like Rceptor Activation and Cellular Signaling", The Journal of Biological Chemistry, 286(42): 36532-36549, Published Online Aug. 26, 2011.
Chow et al. "Acute Actions and Novel Targets of Matrix Metalloproteinases in the Heart and Vasculature", British Journal of Pharmacology, 152(2): 189-205, Published Online Jun. 25, 2007.
Devy et al. "New Strategies for the Next Generation of Matrix-Metalloproteinase Inhibitors: Selectively Targeting Membrane-Anchored MMPs With Therapeutic Antibiodies", Biochemistry Research International, 2011: 1-11, Published Online Oct. 28, 2010.
Elkington et al. "The Paradox of Matrix Metalloproteinases in Infectious Disease", Clinical and Experimental Immunology, 142(1): 12-20, Published Online Jun. 16, 2005.
Fujita et al. "Doxycycline Attenuated Lung Injury by Its Biological Effect Apart From Its Antimicrobial Function", Pulmonary Pharmacology & Therapeutics, 20(6): 669-675, Published Online Sep. 14, 2007. p. 669, Last Para, p. 670, 2nd Para, p. 673, 1st Para, Figs.2, 4.
Musher et al. "Resistance of *Streptococcus pneumoniae* to the Macrolides, Azalides, Lincosamines, and Ketolides", UpToDate, Written, Reprint, 3 P., Dec. 31, 2007. Introduction.
Ng et al. "Doxycycline Treatment Attenuates Acute Lung Injury in Mice Infected With Virulent Influenza H3N2 Virus: Involvement of Matrix Metalloproteinases", Experimental and Molecular Pathology, 92(3): 287-295, Available Online Mar. 7, 2012. Abstract, p. 288, 1st and 2nd Para, Result Section, p. 294, 2nd Para.
Renckens et al. "Matrix Metalloproteinase-9 Deficiency Impairs Host Defense Against Abdominal Sepsis", The Journal of Immunology, 176(6):3735-3741, Mar. 15, 2006.
Sagi "Tissue and Extracellular Remodelling/MMPs", 41st Lorne Conference on Protein Structure and Function 2016, Lorne, Victoria, Australia, Feb. 7-11, 2016, Oral Presentation, # 02, Feb. 7, 2016.
Talmi-Frank et al. "Controlling Extra Cellular Degradation Rescues Tissue Phenotypes During Influenza Infection", ILANIT Meeting, Elat, Israel, Poster, Feb. 10-13, 2014.

(Continued)

Primary Examiner — Bao Q Li

(57) ABSTRACT

A method of treating or preventing a disease associated with a secondary infection in a subject infected with a pathogen is provided. The method comprises administering to the subject a therapeutically effective amount of an anti-pathogenic agent directed towards the pathogen and a therapeutically effective amount of an agent which down-regulates at least one extracellular matrix-associated polypeptide.

4 Claims, 22 Drawing Sheets
(15 of 22 Drawing Sheet(s) Filed in Color)
Specification includes a Sequence Listing.

(56) References Cited

OTHER PUBLICATIONS

Udi et al. "Inhibition Mechanism of Membrane Metalloproteinase by An Exosite-Swiveling Conformational Antibody", Structure, 23(1): 104-115, Published Online Dec. 4, 2014.
Udi et al. "Novel Inhibition Mechanism of Membrane Metalloproteinase by An Exosite-Swiveling Conformational Antibody", Supplemental Information, Structure, 23(1): 1-18, Published Online Dec. 4, 2014.
Vandenbroucke et al. "Is There New Hope for Therapeutic Matrix Metalloproteinase Inhibition?", Nature Reviews Drug Discovery, 13(12): 904-927, Published Online Nov. 7, 2014. p. 8, 2nd Para , 2 Last Para, p. 9, Right Line, 2nd Para, p. 10, 1st Para-p. 13, Left col., 2nd Para, Tables 1, 2, Fig.3.
Vanlaere et al. "Matrix Metalloproteinases as Drug Targets in Infections Caused by Gram-Negative Bacteria and in Septic Shock", Clinical Microbiology Reviews, 22(2): 224-239, Apr. 2009.
Supplementary European Search Report and the European Search Opinion dated May 29, 2018 From the European Patent Office Re. Application No. 16748836.0. (10 Pages).
Leib et al "Inhibition of Matrix Metalloproteinases and Tumour Necrosis Factor Alpha Converting Enzyme as Adjuvant Therapy in Pneumococcal Meningitis", Brain, XP055476051, 124(9): 1734-1742, Sep. 2001. Abstract, p. 1734-1741.

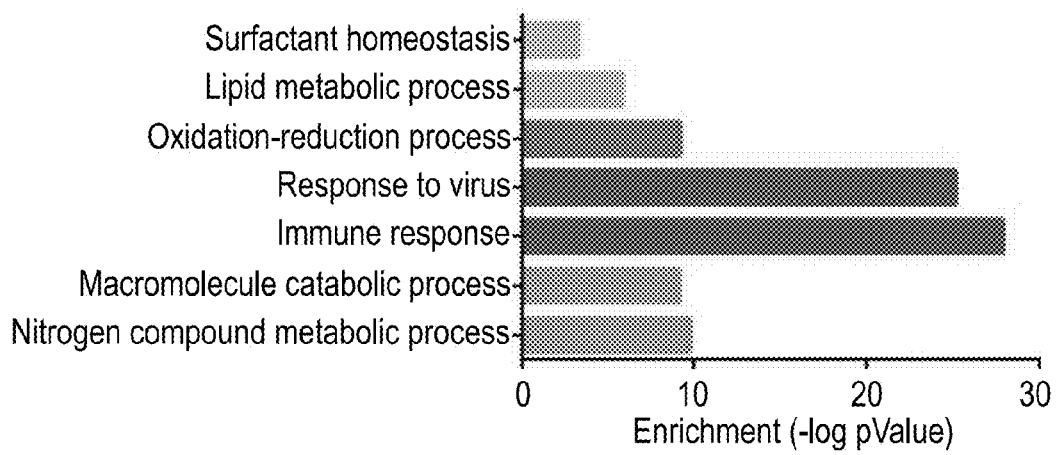
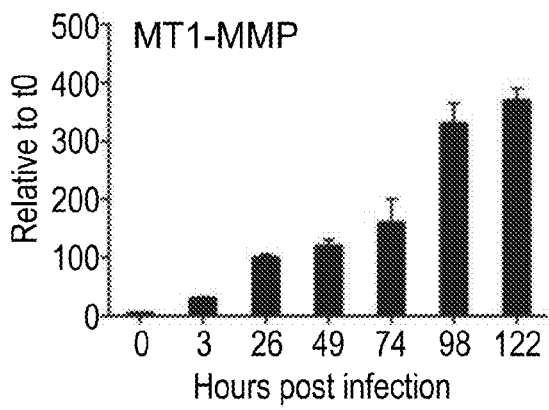
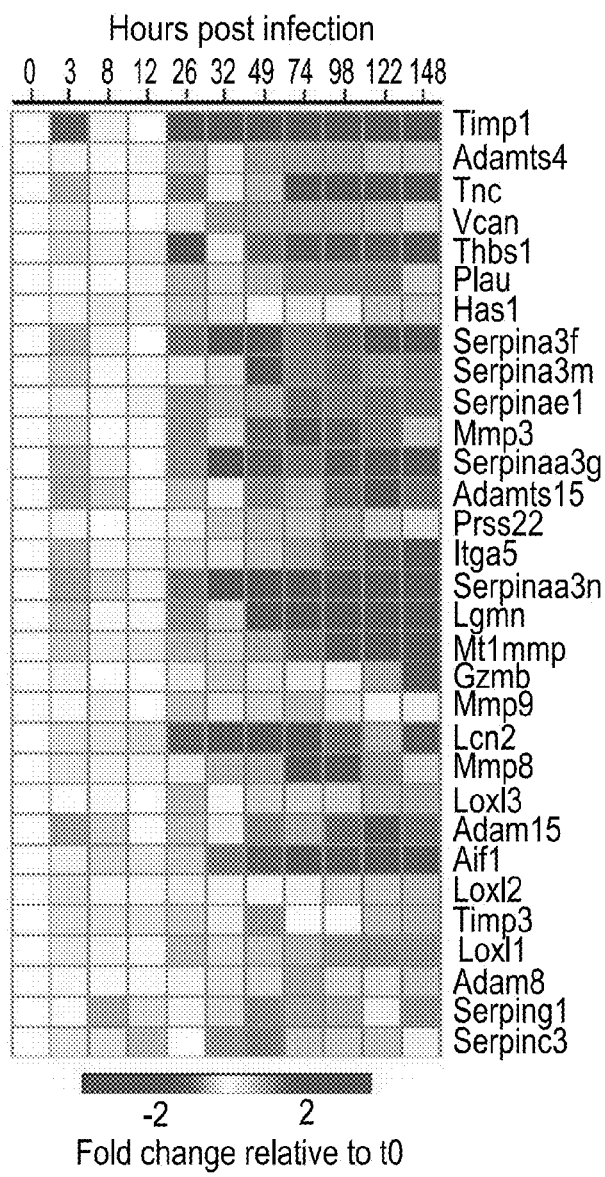

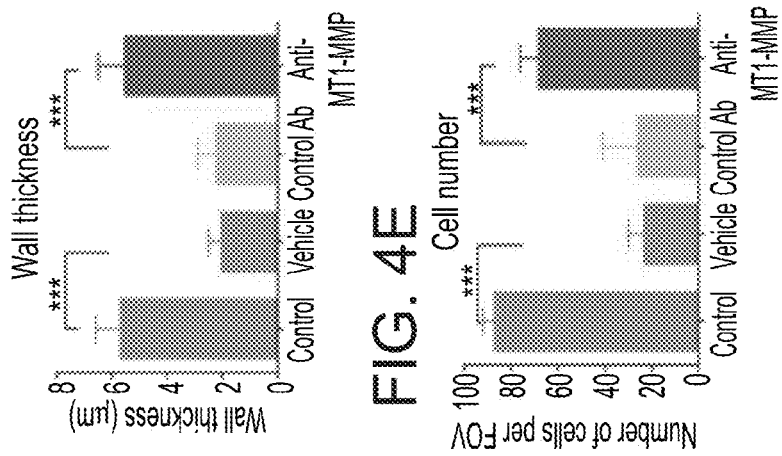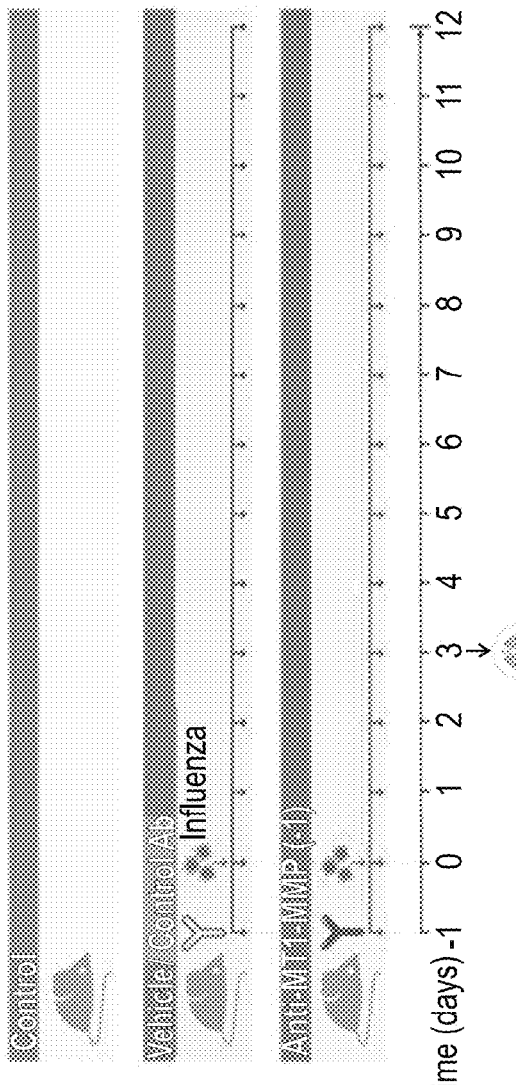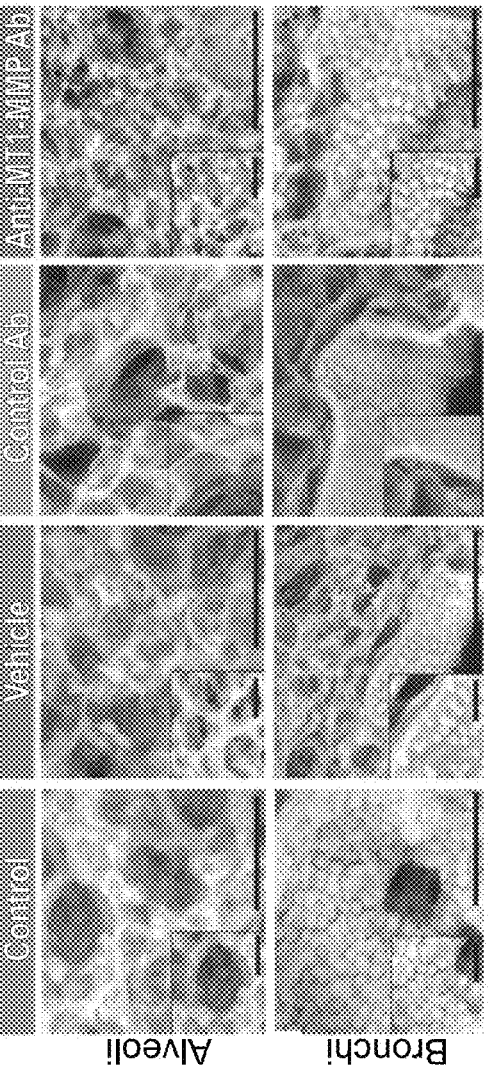
FIG. 4A
FIG. 4B
FIG. 4C
FIG. 4D
FIG. 4E

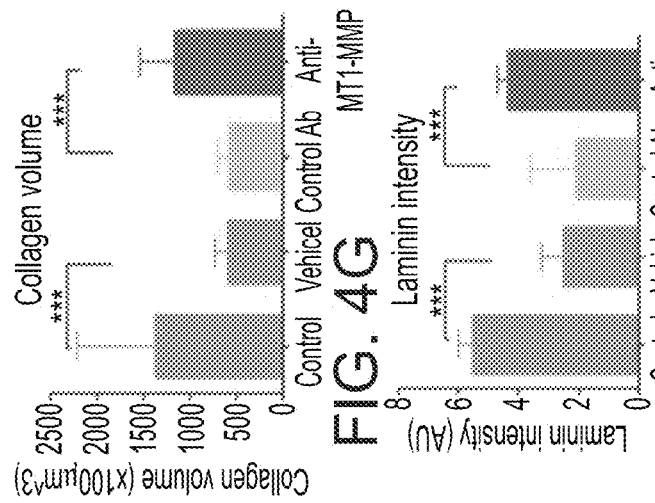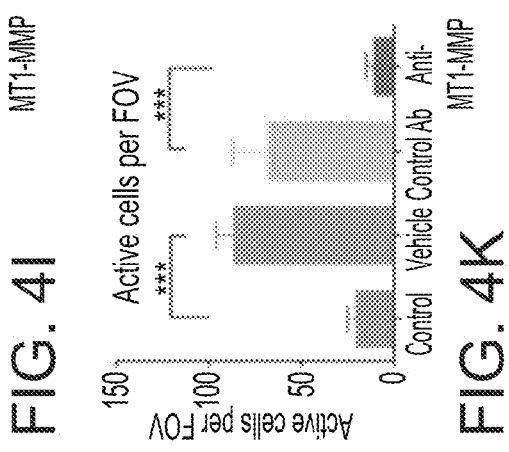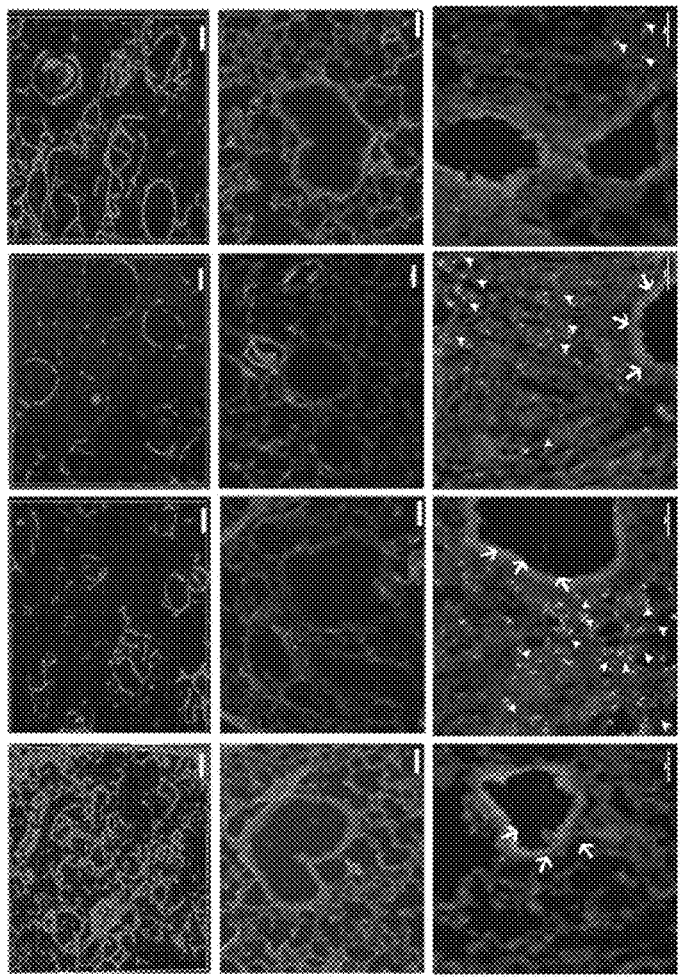

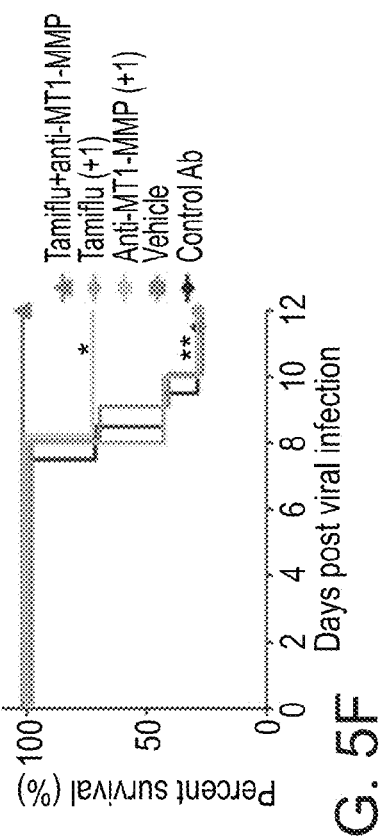
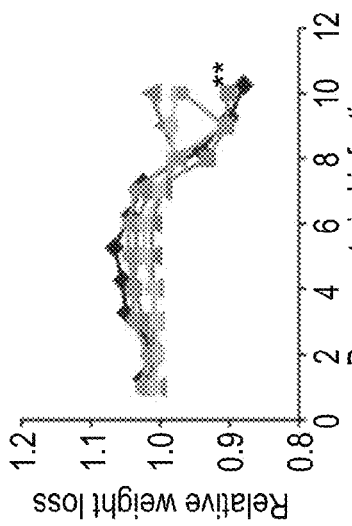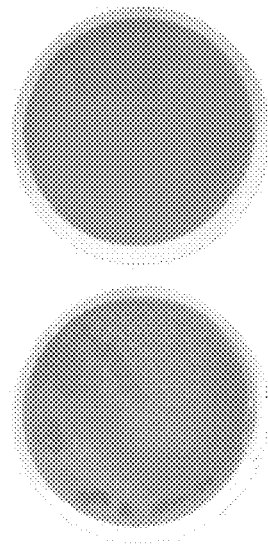
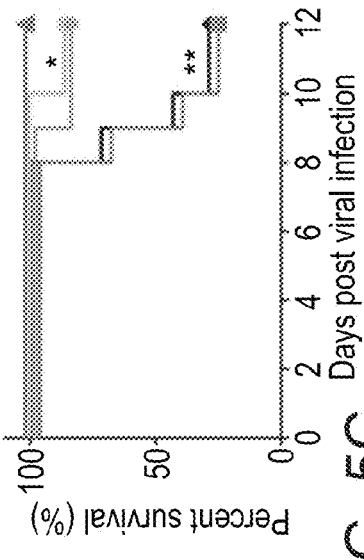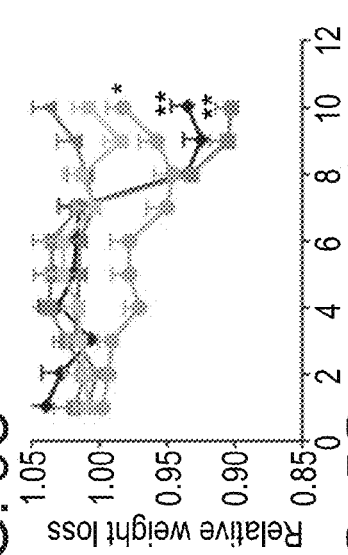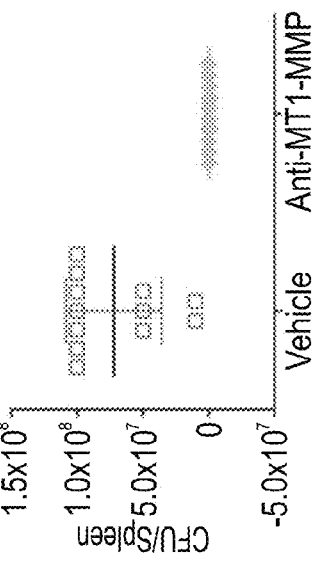

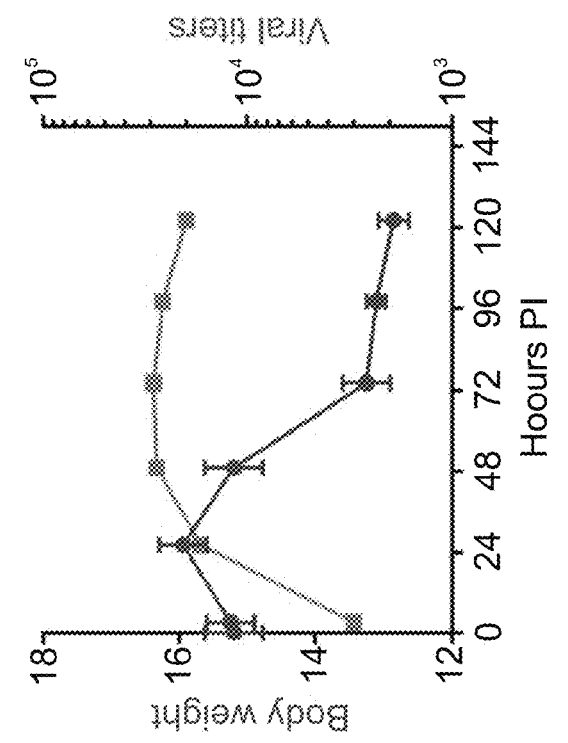
FIG. 6D
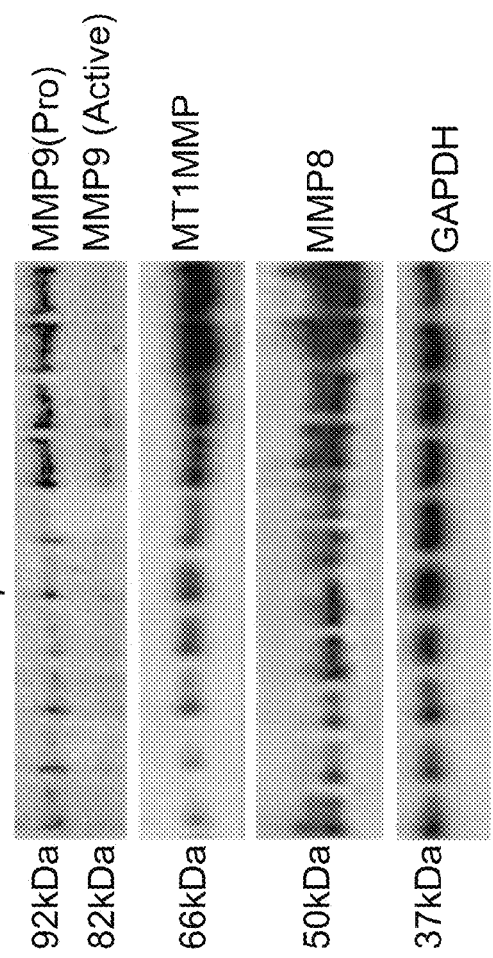
FIG. 6B
FIG. 6C

FIG. 9A
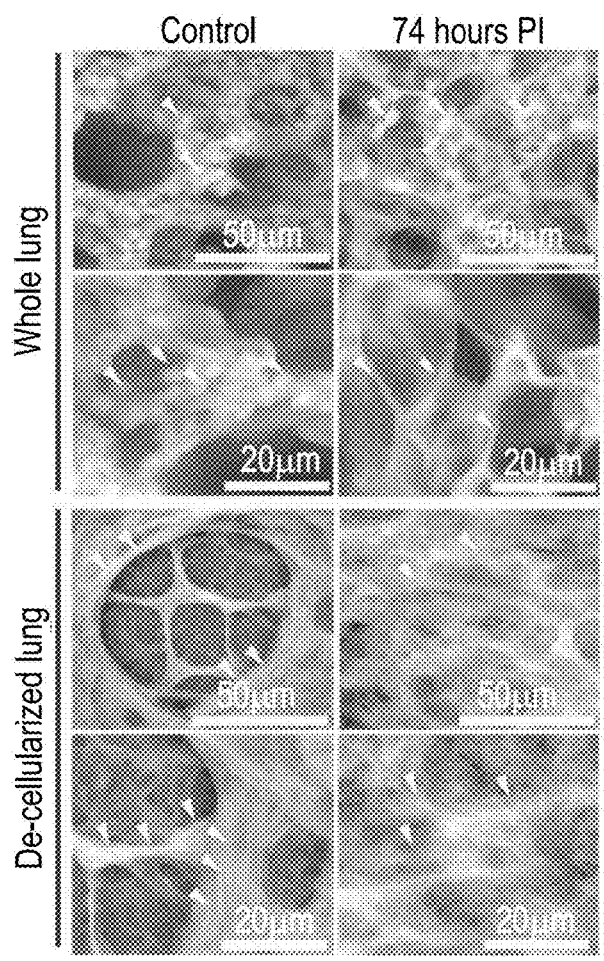
FIG. 9B
FIG. 9C
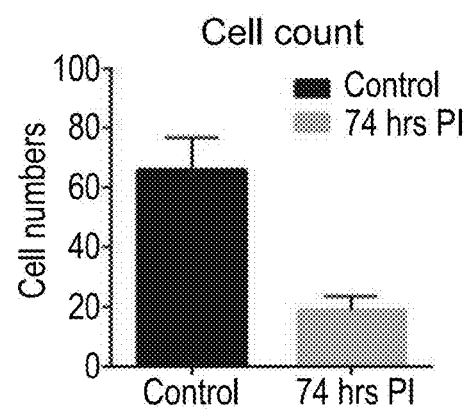
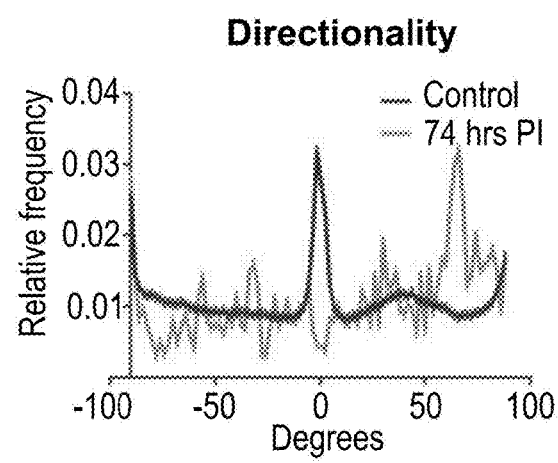
FIG. 9D

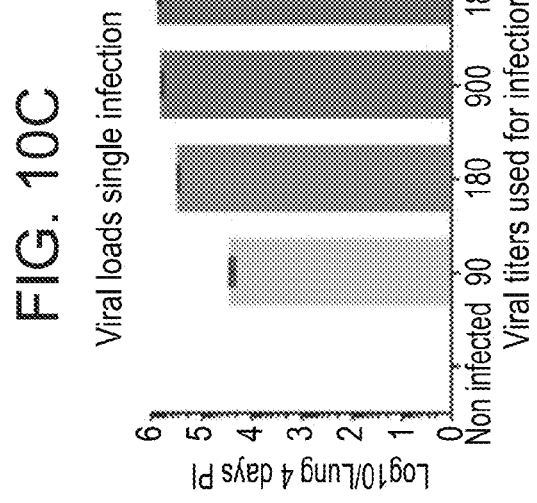
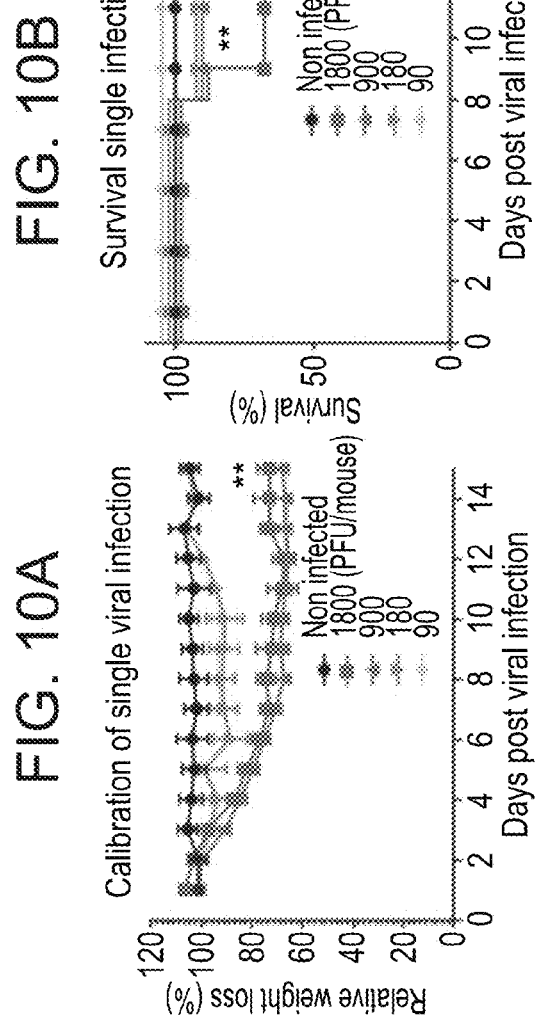

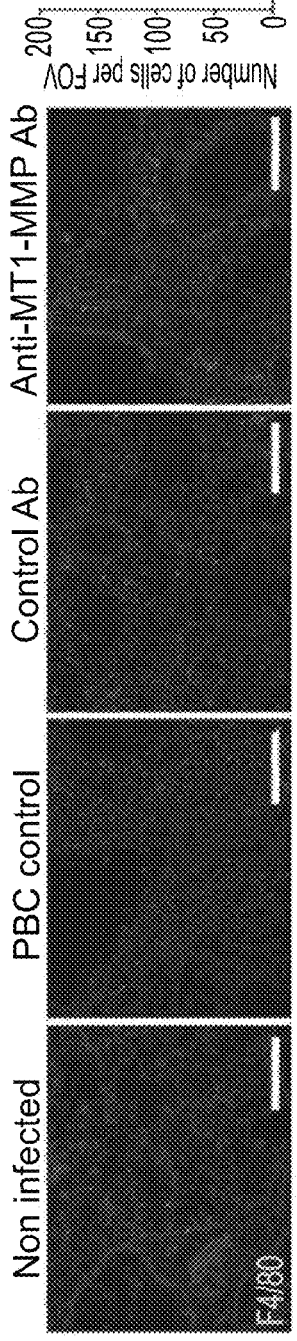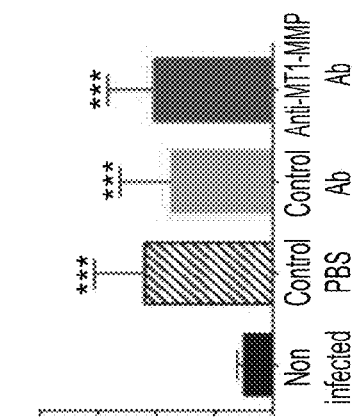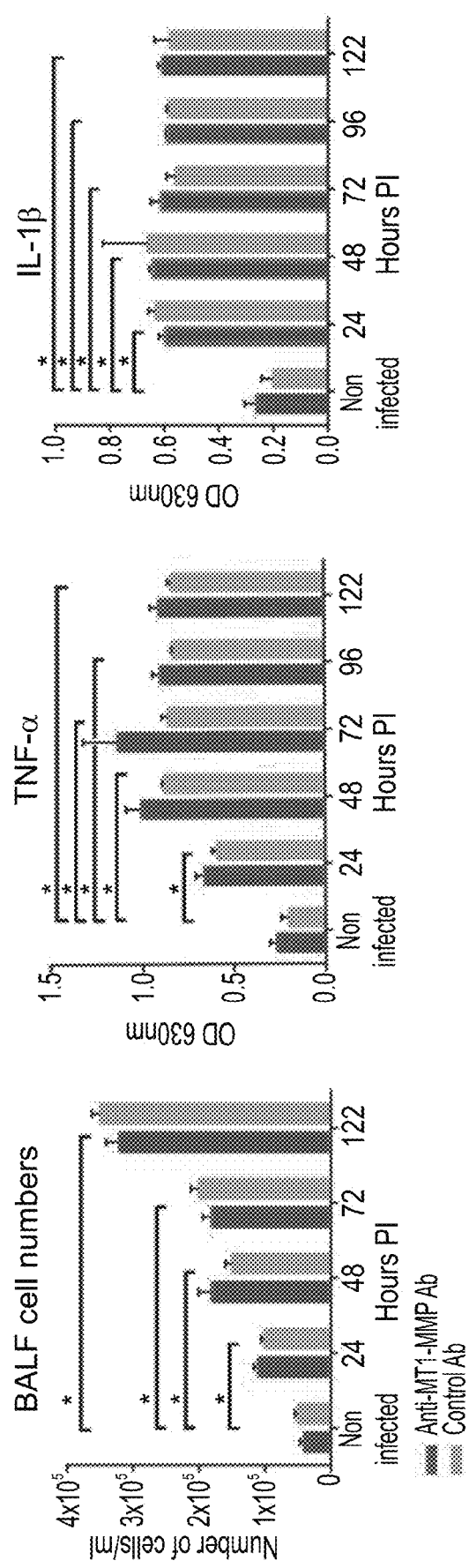

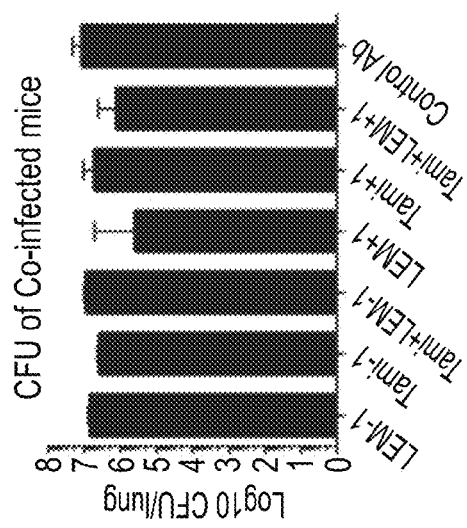
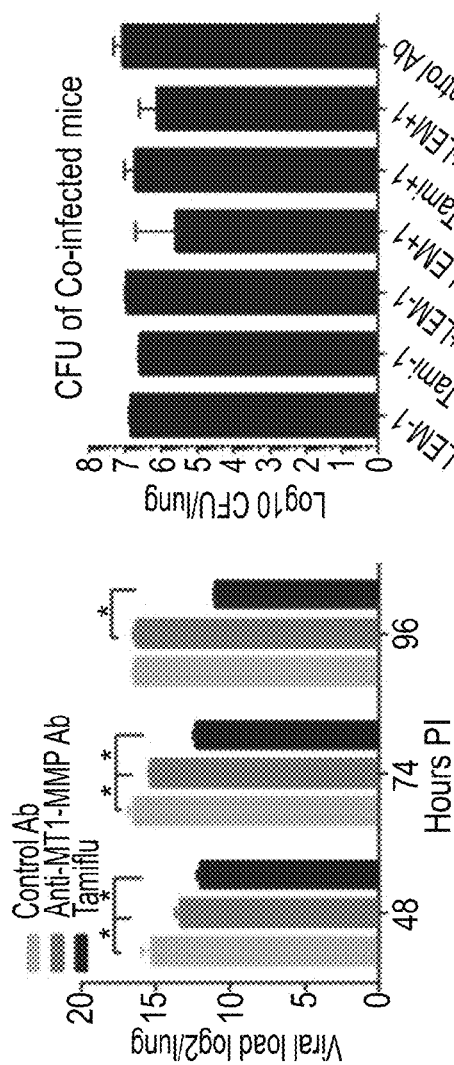
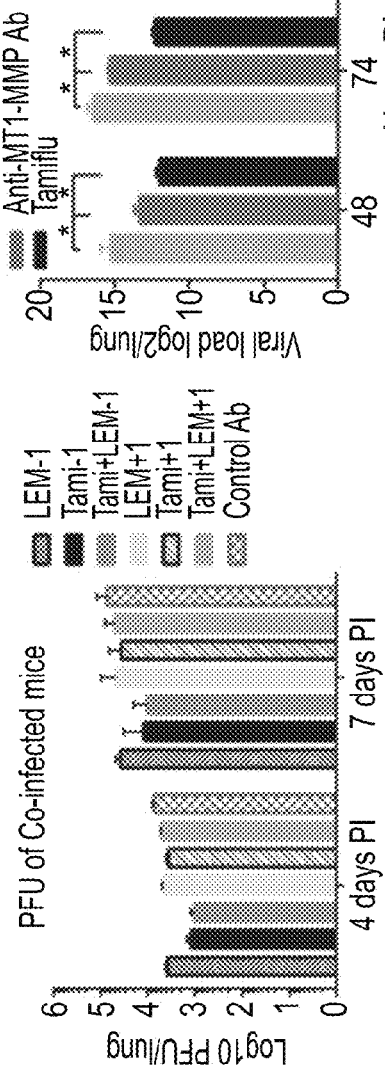
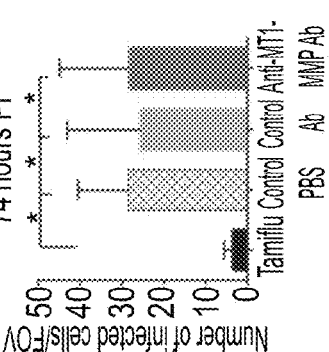
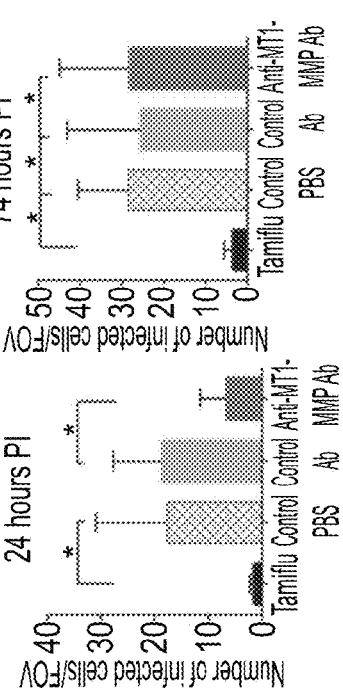
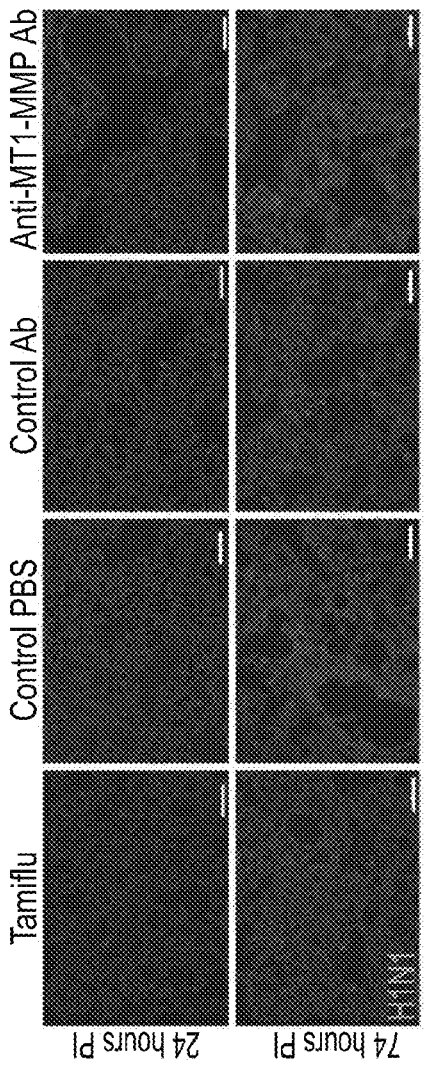

SEQUENCE LISTING

<160> NUMBER OF SEQ ID NOS: 55

<210> SEQ ID NO 1
<211> LENGTH: 931
<212> TYPE: DNA
<213> ORGANISM: homo sapiens

<400> SEQUENCE: 1

```
tttcgtcggc ccgccccttg gcttctgcac tgatggtggg tggatgagta atgcatccag      60
gaagcctgga ggcctgtggt ttccgcaccc gctgccaccc ccgcccctag cgtggacatt     120
tatcctctag cgctcaggcc ctgccgccat cgccgcagat ccagcgccca gagagacacc     180
agagaaccca ccatggcccc ctttgagccc ctggcttctg gcatcctgtt gttgctgtgg     240
ctgatagccc ccagcagggc ctgcacctgt gtcccacccc acccacagac ggccttctgc     300
aattccgacc tcgtcatcag ggccaagttc gtggggacaa cagaagtcaa ccagaccacc     360
ttataccagc gttatgagat caagatgacc aagatgtata aagggttcca agccttaggg     420
```

| | |
|---|---|
| gatgccgctg acatccggtt cgtctacacc cccgccatgg agagtgtctg cggatacttc | 480 |
| cacaggtccc acaaccgcag cgaggagttt ctcattgctg aaaaactgca ggatggactc | 540 |
| ttgcacatca ctacctgcag ttttgtggct ccctggaaca gcctgagctt agctcagcgc | 600 |
| cggggcttca ccaagaccta cactgttggc tgtgaggaat gcacagtgtt tccctgttta | 660 |
| tccatcccct gcaaactgca gagtggcact cattgcttgt ggacggacca gctcctccaa | 720 |
| ggctctgaaa agggcttcca gtcccgtcac cttgcctgcc tgcctcggga gccagggctg | 780 |
| tgcacctggc agtccctgcg gtcccagata gcctgaatcc tgcccggagt ggaagctgaa | 840 |
| gcctgcacag tgtccaccct gttcccactc ccatctttct tccggacaat gaaataaaga | 900 |
| gttaccaccc agcagaaaaa aaaaaaaaaa a | 931 |

<210> SEQ ID NO 2
<211> LENGTH: 4410
<212> TYPE: DNA
<213> ORGANISM: homo sapiens

<400> SEQUENCE: 2

| | |
|---|---|
| ggggagaacc cacagggaga cccacagaca catatgcacg agagagacag aggaggaaag | 60 |
| agacagagac aaaggcacag cggaagaagg cagagacagg gcaggcacag aagcggccca | 120 |
| gacagagtcc tacagaggga gaggccagag aagctgcaga agacacaggc agggagagac | 180 |
| aaagatccag gaaggagggg ctcaggagga gagtttggag aagccagacc cctgggcacc | 240 |
| tctcccaagc ccaaggacta agttttctcc atttccttta acggtcctca gcccttctga | 300 |
| aaactttgcc tctgaccttg gcaggagtcc aagcccccag gctacagaga ggagcttttcc | 360 |
| aaagctaggg tgtggaggac ttggtgccct agacggcctc agtccctccc agctgcagta | 420 |
| ccagtgccat gtcccagaca ggctcgcatc ccgggagggg cttggcaggg cgctggctgt | 480 |
| ggggagccca accctgcctc ctgctcccca ttgtgccgct ctcctggctg gtgtggctgc | 540 |
| ttctgctact gctggcctct ctcctgccct cagcccggct ggccagcccc ctcccccggg | 600 |
| aggaggagat cgtgtttcca gagaagctca acggcagcgt cctgcctggc tcgggcgccc | 660 |
| ctgccaggct gttgtgccgc ttgcaggcct ttggggagac gctgctacta gagctggagc | 720 |
| aggactccgg tgtgcaggtc gagggggctga cagtgcagta cctgggccag gcgcctgagc | 780 |
| tgctgggtgg agcagagcct ggcacctacc tgactggcac catcaatgga gatccggagt | 840 |
| cggtggcatc tctgcactgg gatgggggag ccctgttagg cgtgttacaa tatcgggggg | 900 |
| ctgaactcca cctccagccc ctggaggag gcaccccctaa ctctgctggg gaccctgggg | 960 |
| ctcacatcct acgccggaag agtcctgcca gcggtcaagg tccatgtgc aacgtcaagg | 1020 |
| ctcctcttgg aagccccagc cccagacccc gaagagccaa gcgctttgct tcactgagta | 1080 |
| gatttgtgga gacactggtg gtggcagatg acaagatggc cgcattccac ggtgcggggc | 1140 |
| taaagcgcta cctgctaaca gtgatggcag cagcagccaa ggccttcaag cacccaagca | 1200 |
| tccgcaatcc tgtcagcttg gtggtgactc ggctagtgat cctggggtca ggcgaggagg | 1260 |
| ggccccaagt ggggcccagt gctgcccaga ccctgcgcag cttctgtgcc tggcagcggg | 1320 |
| gcctcaacac ccctgaggac tcggaccctg accactttga cacagccatt ctgtttaccc | 1380 |
| gtcaggacct gtgtggagtc tccacttgcg acacgctggg tatggctgat gtgggcaccg | 1440 |
| tctgtgaccc ggctcggagc tgtgccattg tggaggatga tgggctccag tcagccttca | 1500 |
| ctgctgctca tgaactgggt catgtcttca acatgctcca tgacaactcc aagccatgca | 1560 |
| tcagtttgaa tgggcctttg agcacctctc gccatgtcat ggcccctgtg atggctcatg | 1620 |

```
tggatcctga ggagccctgg tcccctgca gtgcccgctt catcactgac ttcctggaca    1680
atggctatgg gcactgtctc ttagacaaac cagaggctcc attgcatctg cctgtgactt    1740
tccctggcaa ggactatgat gctgaccgcc agtgccagct gaccttcggg cccgactcac    1800
gccattgtcc acagctgccg ccgccctgtg ctgccctctg gtgctctggc cacctcaatg    1860
gccatgccat gtgccagacc aaacactcgc cctgggccga tggcacaccc tgcgggcccg    1920
cacaggcctg catgggtggt cgctgcctcc acatggacca gctccaggac ttcaatattc    1980
cacaggctgg tggctggggt ccttggggac catggggtga ctgctctcgg acctgtgggg    2040
gtggtgtcca gttctcctcc cgagactgca cgaggcctgt cccccggaat ggtggcaagt    2100
actgtgaggg ccgccgtacc cgcttccgct cctgcaacac tgaggactgc ccaactggct    2160
cagccctgac cttccgcgag gagcagtgtg ctgcctacaa ccaccgcacc gacctcttca    2220
agagcttccc agggcccatg gactgggttc ctcgctacac aggcgtggcc ccccaggacc    2280
agtgcaaact cacctgccag gcccaggcac tgggctacta ctatgtgctg agccacgggt    2340 ggtagatgg accccctgt tccccggaca gctcctcggt ctgtgtccag ggccgatgca    2400
tccatgctgc tgtgatcgc atcattggct ccaagaagaa gtttgacaag tgcatggtgt    2460
gcggagggga cggttctggt tgcagcaagc agtcaggctc cttcaggaaa ttcaggtacg    2520
gatacaacaa tgtggtcact atccccgcgg gggccaccca cattcttgtc cggcagcagg    2580
gaaaccctgg ccaccggagc atctacttgg ccctgaagct gccagatggc tcctatgccc    2640
tcaatggtga atacacgctg atgccctccc cacagatgt ggtactgcct ggggcagtca    2700
gcttgcgcta cagcggggcc actgcagcct cagagacact gtcaggccat gggccactgg    2760
cccagccttt gacactgcaa gtcctagtgg ctggcaaccc ccaggacaca cgcctccgat    2820
acagcttctt cgtgccccgg ccgacccctt caacgccacg ccccactccc caggactggc    2880
tgcaccgaag agcacagatt ctggagatcc ttcggcggcg cccctgggcg ggcaggaaat    2940
aacctcacta tcccggctgc cctttctggg caccggggcc tcggacttag ctgggagaaa    3000
gagagagctt ctgttgctgc ctcatgctaa gactcagtgg ggaggggctg tgggcgtgag    3060
acctgcccct cctctctgcc ctaatgcgca ggctggccct gccctggttt cctgccctgg    3120
gaggcagtga tgggttagtg gatggaaggg gctgacagac agccctccat ctaaactgcc    3180
ccctctgccc tgcgggtcac aggagggagg gggaaggcag ggagggcctg ggccccagtt    3240
gtatttattt agtatttatt cacttttatt tagcaccagg gaaggggaca aggactaggg    3300
tcctggggaa cctgacccct gaccctcat agccctcacc ctggggctag gaaatccagg    3360
gtggtggtga taggtataag tggtgtgtgt atgcgtgtgt gtgtgtgtga aaatgtgtgt    3420
gtgcttatgt atgaggtaca acctgttctg ctttcctctt cctgaatttt atttttgggg    3480
aaaagaaaag tcaagggtag ggtgggcctt cagggagtga gggattatct ttttttttt    3540 ttctttcttt ctttctttt ttttttgag acagaatctc gctctgtcgc ccaggctgga    3600
gtgcaatggc acaatctcgg ctcactgcat cctccgcctc ccgggttcaa gtgattctca    3660
tgcctcagcc tcctgagtag ctgggattac aggctcctgc caccgcgcc ggctaatttt    3720 tgttttgttt tgtttggaga cagagtctcg ctattgtcac cagggctgga atgatttcag    3780
ctcactgcaa ccttcgccac ctgggttcca gcaattctcc tgcctcagcc tcccgagtag    3840
ctgagattat aggcacctac caccacgccc ggctaatttt tgtatttta gtagagacgg    3900 ggtttcacca tgttggccag gctggtctcg aactcctgac cttaggtgat ccactcgcct    3960
```

| | |
|---|---|
| tcatctccca aagtgctggg attacaggcg tgagccaccg tgcctggcca cgcccaacta | 4020 |
| atttttgtat ttttagtaga gacagggttt caccatgttg gccaggctgc tcttgaactc | 4080 |
| ctgacctcag gtaatcgacc tgcctcggcc tcccaaagtg ctgggattac aggtgtgagc | 4140 |
| caccacgccc ggtacatatt ttttaaattg aattctacta tttatgtgat ccttttggag | 4200 |
| tcagacagat gtggttgcat cctaactcca tgtctctgag cattagattt ctcatttgcc | 4260 |
| aataataata cctcccttag aagtttgttg tgaggattaa ataatgtaaa taaagaacta | 4320 |
| gcataacact caaaaaaaaa aaaaaaaaaa aaaaaaaaaa aaaaaaaaaa aaaaaaaaaa | 4380 |
| aaaaaaaaaa aaaaaaaaaa aaaaaaaaaa | 4410 |

<210> SEQ ID NO 3
<211> LENGTH: 8605
<212> TYPE: DNA
<213> ORGANISM: homo sapiens

<400> SEQUENCE: 3

| | |
|---|---|
| aattcgccaa ctgaaaaagt gggaaaggat gtctggaggc gaggcgtccc attacagagg | 60 |
| aaggagctcg ctatataagc cagccaaagt tggctgcacc ggccacagcc tgcctactgt | 120 |
| cacccgcctc tcccgcgcgc agatacacgc ccccgcctcc gtgggcacaa aggcagcgct | 180 |
| gctggggaac tcgggggaac gcgcacgtgg gaaccgccgc agctccacac tccaggtact | 240 |
| tcttccaagg acctaggtct ctcgcccatc ggaaagaaaa taattctttc aagaagatca | 300 |
| gggacaactg atttgaagtc tactctgtgc ttctaaatcc ccaattctgc tgaaagtgag | 360 |
| ataccctaga gccctagagc cccagcagca cccagccaaa cccacctcca ccatgggggc | 420 |
| catgactcag ctgttggcag gtgtctttct tgctttcctt gccctcgcta ccgaaggtgg | 480 |
| ggtcctcaag aaagtcatcc ggcacaagcg acagagtggg gtgaacgcca ccctgccaga | 540 |
| agagaaccag ccagtggtgt ttaaccacgt ttacaacatc aagctgccag tgggatccca | 600 |
| gtgttcggtg gatctggagt cagccagtgg ggagaaagac ctggcaccgc cttcagagcc | 660 |
| cagcgaaagc tttcaggagc acacagtgga tgggaaaaac cagattgtct tcacacatcg | 720 |
| catcaacatc ccccgccggg cctgtggctg tgccgcagcc cctgatgtta aggagctgct | 780 |
| gagcagactg gaggagctgg agaacctggt gtcttccctg agggagcaat gtactgcagg | 840 |
| agcaggctgc tgtctccagc ctgccacagg ccgcttggac accaggccct tctgtagcgg | 900 |
| tcggggcaac ttcagcactg aaggatgtgg ctgtgtctgc gaacctggct ggaaaggccc | 960 |
| caactgctct gagcccgaat gtccaggcaa ctgtcacctt cgaggccggt gcattgatgg | 1020 |
| gcagtgcatc tgtgacgacg gcttcacggg cgaggactgc agccagctgg cttgccccag | 1080 |
| cgactgcaat gaccagggca gtgcgtaaa tggagtctgc atctgtttcg aaggctacgc | 1140 |
| cggggctgac tgcagccgtg aaatctgccc agtgccctgc agtgaggagc acggcacatg | 1200 |
| tgtagatggc ttgtgtgtgt gccacgatgg cttttcaggc gatgactgca acaagcctct | 1260 |
| gtgtctcaac aattgctaca accgtggacg atgcgtggaa aatgagtgcg tgtgtgatga | 1320 |
| gggtttcacg ggcgaagact gcagtgagct catctgcccc aatgactgct tcgaccgggg | 1380 |
| ccgctgcatc aatggcacct gctactgcga agaaggcttc acaggtgaag actgcgggaa | 1440 |
| acccacctgc ccacatgcct gccacaccca gggccggtgt gaggaggggc agtgtgtatg | 1500 |
| tgatgagggc tttgccggtg tggactgcag cgagaagagg tgtcctgctg actgtcacaa | 1560 |
| tcgtggccgc tgtgtagacg ggcggtgtga gtgtgatgat ggtttcactg gagctgactg | 1620 |
| tgggagctc aagtgtccca atggctgcag tggccatggc cgctgtgtca atgggcagtg | 1680 |

```
tgtgtgtgat gagggctata ctggggagga ctgcagccag ctacggtgcc ccaatgactg    1740
tcacagtcgg ggccgctgtg tcgagggcaa atgtgtatgt gagcaaggct caagggcta    1800 tgactgcagt gacatgagct gccctaatga ctgtcaccag cacggccgct gtgtgaatgg    1860
catgtgtgtt tgtgatgacg gctacacagg ggaagactgc cgggatcgcc aatgccccag    1920
ggactgcagc aacaggggcc tctgtgtgga cggacagtgc gtctgtgagg acggcttcac    1980
cggccctgac tgtgcagaac tctcctgtcc aaatgactgc catggccagg tcgctgtgt    2040 gaatgggcag tgcgtgtgcc atgaaggatt tatgggcaaa gactgcaagg agcaaagatg    2100
tcccagtgac tgtcatggcc agggccgctg cgtggacggc cagtgcatct gccacgaggg    2160
cttcacaggc ctggactgtg gccagcactc ctgccccagt gactgcaaca acttaggaca    2220
atgcgtctcg ggccgctgca tctgcaacga gggctacagc ggagaagact gctcagaggt    2280
gtctcctccc aaagacctcg ttgtgacaga agtgacggaa gagacggtca acctggcctg    2340
ggacaatgag atgcgggtca cagagtacct tgtcgtgtac acgcccaccc acgagggtgg    2400
tctggaaatg cagttccgtg tgcctgggga ccagacgtcc accatcatcc aggagctgga    2460
gcctggtgtg gagtacttta tccgtgtatt tgccatcctg gagaacaaga gagcattcc    2520 tgtcagcgcc agggtggcca cgtacttacc tgcacctgaa ggcctgaaat tcaagtccat    2580
caaggagaca tctgtggaag tggagtggga tcctctagac attgcttttg aaacctggga    2640
gatcatcttc cggaatatga ataaagaaga tgagggagag atcaccaaaa gcctgaggag    2700
gccagagacc tcttaccggc aaactggtct agctcctggg caagagtatg agatatctct    2760
gcacatagtg aaaaacaata cccggggccc tggcctgaag agggtgacca ccacacgctt    2820
ggatgccccc agccagatcg aggtgaaaga tgtcacagac accactgcct tgatcacctg    2880
gttcaagccc ctggctgaga tcgatggcat tgagctgacc tacggcatca agacgtgcc    2940 aggagaccgt accaccatcg atctcacaga ggacgagaac cagtactcca tcgggaacct    3000
gaagcctgac actgagtacg aggtgtccct catctcccgc agaggtgaca tgtcaagcaa    3060
cccagccaaa gagaccttca caacaggcct cgatgctccc aggaatcttc gacgtgtttc    3120
ccagacagat aacagcatca ccctggaatg gaggaatggc aaggcagcta ttgacagtta    3180
cagaattaag tatgccccca tctctggagg ggaccacgct gaggttgatg ttccaaagag    3240
ccaacaagcc acaaccaaaa ccacactcac aggtctgagg ccgggaactg aatatgggat    3300
tggagtttct gctgtgaagg aagacaagga gagcaatcca gcgaccatca acgcagccac    3360
agagttggac acgcccaagg accttcaggt ttctgaaact gcagagacca gcctgaccct    3420
gctctggaag acaccgttgg ccaaatttga ccgctaccgc tcaattaca gtctccccac    3480 aggccagtgg gtgggagtgc agcttccaag aaacaccact tcctatgtcc tgagaggcct    3540
ggaaccagga caggagtaca atgtcctcct gacagccgag aaaggcagac acaagagcaa    3600 gccccgcacgt gtgaaggcat ccactgaaca agccctgag ctggaaaacc tcaccgtgac    3660
tgaggttggc tgggatggcc tcagactcaa ctggaccgca gctgaccagg cctatgagca    3720
ctttatcatt caggtgcagg aggccaacaa ggtggaggca gctcggaacc tcaccgtgcc    3780
tggcagcctt cgggctgtgg ataccgggcc ctcaaggct gctacgcctt atacagtctc    3840
catctatggg gtgatccagg gctatagaac accagtgctc tctgctgagg cctccacagg    3900
ggaaactccc aatttgggag aggtcgtggt ggccgaggtg ggctgggatg ccctcaaact    3960
caactggact gctccagaag gggcctatga gtacttttc attcaggtgc aggaggctga    4020
```

-continued

| | | | | |
|---|---|---|---|---|
| cacagtagag | gcagcccaga | acctcaccgt | cccaggagga | ctgaggtcca cagacctgcc | 4080 |
| tgggctcaaa | gcagccactc | attataccat | caccatccgc | ggggtcactc aggacttcag | 4140 |
| cacaacccct | ctctctgttg | aagtcttgac | agaggaggtt | ccagatatgg gaaacctcac | 4200 |
| agtgaccgag | gttagctggg | atgctctcag | actgaactgg | accacgccag atggaaccta | 4260 |
| tgaccagttt | actattcagg | tccaggaggc | tgaccaggtg | gaagaggctc acaatctcac | 4320 |
| ggttcctggc | agcctgcgtt | ccatggaaat | cccaggcctc | agggctggca ctccttacac | 4380 |
| agtcaccctg | cacggcgagg | tcaggggcca | cagcactcga | ccccttgctg tagaggtcgt | 4440 |
| cacagaggat | ctcccacagc | tgggagattt | agccgtgtct | gaggttggct gggatggcct | 4500 |
| cagactcaac | tggaccgcag | ctgacaatgc | ctatgagcac | tttgtcattc aggtgcagga | 4560 |
| ggtcaacaaa | gtggaggcag | cccagaacct | cacgttgcct | ggcagcctca gggctgtgga | 4620 |
| catcccgggc | ctcgaggctg | ccacgcctta | tagagtctcc | atctatgggg tgatccgggg | 4680 |
| ctatagaaca | ccagtactct | ctgctgaggc | ctccacagcc | aaagaacctg aaattggaaa | 4740 |
| cttaaatgtt | tctgacataa | ctcccgagag | cttcaatctc | tcctggatgg ctaccgatgg | 4800 |
| gatcttcgag | acctttacca | ttgaaattat | tgattccaat | aggttgctgg agactgtgga | 4860 |
| atataatatc | tctggtgctg | aacgaactgc | ccatatctca | gggctacccc ctagtactga | 4920 |
| ttttattgtc | tacctctctg | gacttgctcc | cagcatccgg | accaaaacca tcagtgccac | 4980 |
| agccacgaca | gaggccctgc | cccttctgga | aaacctaacc | atttccgaca ttaatcccta | 5040 |
| cgggttcaca | gtttcctgga | tggcatcgga | gaatgccttt | gacagctttc tagtaacggt | 5100 |
| ggtggattct | gggaagctgc | tggacccca | ggaattcaca | ctttcaggaa cccagaggaa | 5160 |
| gctggagctt | agaggcctca | taactggcat | tggctatgag | gttatggtct ctggcttcac | 5220 |
| ccaagggcat | caaaccaagc | ccttgagggc | tgagattgtt | acagaagccg aaccggaagt | 5280 |
| tgacaacctt | ctggtttcag | atgccacccc | agacggtttc | cgtctgtcct ggacagctga | 5340 |
| tgaagggtc | ttcgacaatt | ttgttctcaa | aatcagagat | accaaaaagc agtctgagcc | 5400 |
| actggaaata | accctacttg | ccccgaacg | taccagggac | ataacaggtc tcagagaggc | 5460 |
| tactgaatac | gaaattgaac | tctatggaat | aagcaaagga | aggcgatccc agacagtcag | 5520 |
| tgctatagca | acaacagcca | tgggctcccc | aaaggaagtc | attttctcag acatcactga | 5580 |
| aaattcggct | actgtcagct | ggagggcacc | cacagcccaa | gtggagagct tccggattac | 5640 |
| ctatgtgccc | attacaggag | gtacaccctc | catggtaact | gtggacggaa ccaagactca | 5700 |
| gaccaggctg | tgaaaactca | tacctggcgt | ggagtacctt | gtcagcatca tcgccatgaa | 5760 |
| gggctttgag | gaaagtgaac | ctgtctcagg | gtcattcacc | acagctctgg atggcccatc | 5820 |
| tggcctggtg | acagccaaca | tcactgactc | agaagcttg | gccaggtggc agccagccat | 5880 |
| tgccactgtg | gacagttatg | tcatctccta | cacaggcgag | aaagtgccag aaattacacg | 5940 |
| cacggtgtcc | gggaacacag | tggagtatgc | tctgaccgac | ctcgagcctg ccacggaata | 6000 |
| cacactgaga | atctttgcag | agaaagggcc | ccagaagagc | tcaaccatca ctgccaagtt | 6060 |
| cacaacagac | ctcgattctc | caagagactt | gactgctact | gaggttcagt cggaaactgc | 6120 |
| cctccttacc | tggcgacccc | ccgggcatc | agtcaccggt | tacctgctgg tctatgaatc | 6180 |
| agtggatggc | acagtcaagg | aagtcattgt | gggtccagat | accacctcct acagcctggc | 6240 |
| agacctgagc | ccatccaccc | actacacagc | caagatccag | gcactcaatg ggcccctgag | 6300 |
| gagcaatatg | atccagacca | tcttcaccac | aattggactc | ctgtaccccct tcccaaggaa | 6360 |
| ctgctcccaa | gcaatgctga | atggagacac | gacctctggc | ctctacacca tttatctgaa | 6420 |

```
tggtgataag gctgaggcgc tggaagtctt ctgtgacatg acctctgatg ggggtggatg    6480
gattgtgttc ctgagacgca aaaacggacg cgagaacttc taccaaaact ggaaggcata    6540
tgctgctgga tttggggacc gcagagaaga attctggctt gggctggaca acctgaacaa    6600
aatcacagcc caggggcagt acgagctccg ggtggacctg cgggaccatg gggagacagc    6660
ctttgctgtc tatgacaagt tcagcgtggg agatgccaag actcgctaca agctgaaggt    6720
ggaggggtac agtgggacag caggtgactc catggcctac cacaatggca gatccttctc    6780
cacctttgac aaggacacag attcagccat caccaactgt gctctgtcct acaaaggggc    6840
tttctggtac aggaactgtc accgtgtcaa cctgatgggg agatatgggg acaataacca    6900
cagtcagggc gttaactggt ccactggaaa gggccacgaa cactcaatcc agtttgctga    6960
gatgaagctg agaccaagca acttcagaaa tcttgaaggc aggcgcaaac gggcataaat    7020
tccagggacc actgggtgag agaggaataa ggcccagagc gaggaaagga ttttaccaaa    7080
gcatcaatac aaccagccca accatcggtc cacacctggg catttggtga gagtcaaagc    7140
tgaccatgga tccctggggc caacggcaac agcatgggcc tcacctcctc tgtgatttct    7200
ttctttgcac caaagacatc agtctccaac atgtttctgt tttgttgttt gattcagcaa    7260
aaatctccca gtgacaacat cgcaatagtt ttttacttct cttaggtggc tctgggaatg    7320
ggagaggggt aggatgtaca ggggtagttt gttttagaac cagccgtatt ttacatgaag    7380
ctgtataatt aattgtcatt attttgtta gcaaagatta aatgtgtcat tggaagccat    7440 ccctttttt acatttcata caacagaaac cagaaaagca atactgtttc cattttaagg    7500
atatgattaa tattattaat ataataatga tgatgatgat gatgaaaact aaggattttt    7560
caagagatct ttcttccaa acatttctg gacagtacct gattgtattt ttttttaaa     7620 taaaagcaca agtactttg agtttgttat tttgctttga attgttgagt ctgaatttca    7680
ccaaagccaa tcatttgaac aaagcgggga atgttgggat aggaaaggta agtagggata    7740
gtggtcaagt gggaggggtg gaaaggagac taaagactgg gagagaggga agcactttt    7800 ttaaataaag ttgaacacac ttgggaaaag cttacaggcc aggcctgtaa tcccaacact    7860
ttgggaggcc aaggtgggag gatagcttaa ccccaggagt ttgagaccag cctgagcaac    7920
atagtgagaa cttgtctcta cagaaaaaaa aaaaaaaaa aatttaatta ggcaagcgtg    7980
gtagtgcgca cctgtcgtcc cagctactca ggaggctgag gtaggaaaat cactggagcc    8040
caggagttag aggttacagt gagctatgat cacactactg cactccagcc tgggcaacag    8100
agggagaccc tgtctctaaa taaaaaaga aagaaaaaa aaagcttaca acttgagatt    8160
cagcatcttg ctcagtattt ccaagactaa tagattatgg tttaaaagat gcttttatac    8220
tcattttcta atgcaactcc tagaaactct atgatatagt tgaggtaagt attgttacca    8280
cacatgggct aagatcccca gaggcagact gcctgagttc aattcttggc tccaccattc    8340
ccaagttccc taacctctct atgcctcagt ttcctcttct gtaaagtagg gacactcata    8400
cttctcattt cagaacattt ttgtgaagaa taaattatgt tatccatttg aggcccttag    8460
aatggtaccc ggtgtatatt aagtgctagt acatgttagc tatcatcatt atcactttat    8520
atgagatgga ctggggttca tagaaaccca atgacttgat tgtggctact actcaataaa    8580
taatagaatt tggatttaaa aaaaa                                         8605
```

<210> SEQ ID NO 4
<211> LENGTH: 4193
<212> TYPE: DNA

<213> ORGANISM: homo sapiens

<400> SEQUENCE: 4

```
cttcttctcg ctgagtctcc tcctcggctc tgacggtaca gtgatataat gatgatgggt      60
gtcacaaccc gcatttgaac ttgcaggcga gctgccccga gcctttctgg ggaagaactc     120
caggcgtgcg gacgcaacag ccgagaacat taggtgttgt ggacaggagc tgggaccaag     180
atcttcggcc agccccgcat cctcccgcat cttccagcac cgtcccgcac cctccgcatc     240
cttccccggg ccaccacgct tcctatgtga cccgcctggg caacgccgaa cccagtcgcg     300
cagcgctgca gtgaattttc cccccaaact gcaataagcc gccttccaag gccaagatgt     360
tcataaatat aaagagcatc ttatggatgt gttcaacctt aatagtaacc catgcgctac     420
ataaagtcaa agtgggaaaa agcccaccgg tgagggctc cctctctgga aaagtcagcc      480
taccttgtca tttttcaacg atgcctactt tgccacccag ttacaacacc agtgaatttc     540
tccgcatcaa atggtctaag attgaagtgg acaaaaatgg aaaagatttg aaagagacta     600
ctgtccttgt ggcccaaaat ggaaatatca agattggtca ggactacaaa gggagagtgt     660
ctgtgcccac acatcccgag gctgtgggcg atgcctccct cactgtggtc aagctgctgg     720
caagtgatgc gggtctttac cgctgtgacg tcatgtacgg gattgaagac acacaagaca     780
cggtgtcact gactgtggat ggggttgtgt ttcactacag gcggcaacc agcaggtaca     840
cactgaattt tgaggctgct cagaaggctt gtttggacgt tgggcagtc atagcaactc      900
cagagcagct ctttgctgcc tatgaagatg gatttgagca gtgtgacgca ggctggctgg     960
ctgatcagac tgtcagatat cccatccggg ctcccagagt aggctgttat ggagataaga    1020
tgggaaaggc aggagtcagg acttatggat tccgttctcc ccaggaaact tacgatgtgt    1080
attgttatgt ggatcatctg gatggtgatg tgttccacct cactgtcccc agtaaattca    1140
ccttcgagga ggctgcaaaa gagtgtgaaa accaggatgc caggctggca acagtggggg    1200
aactccaggc ggcatggagg aacggctttg accagtgcga ttacgggtgg ctgtcggatg    1260
ccagcgtgcg ccaccctgtg actgtggcca gggcccagtg tggaggtggt ctacttgggg    1320
tgagaacccct gtatcgtttt gagaaccaga caggcttccc tccccctgat agcagatttg    1380
atgcctactg ctttaaacga cctgatcgct gcaaaatgaa cccgtgcctt aacggaggca    1440
cctgttatcc tactgaaact tcctacgtat gcacctgtgt gccaggatac agcggagacc    1500
agtgtgaact tgattttgat gaatgtcact ctaatccctg tcgtaatgga gccacttgtg    1560
ttgatggttt taacacattc aggtgcctct gccttccaag ttatgttggt gcactttgtg    1620
agcaagatac cgagacatgt gactatggct ggcacaaatt ccaagggcag tgctacaaat    1680
actttgccca tcgacgcaca tgggatgcag ctgaacggga atgccgtctg cagggtgccc    1740
atctcacaag catcctgtct cacgaagaac aaatgtttgt taatcgtgtg ggccatgatt    1800
atcagtggat aggcctcaat gacaagatgt ttgagcatga cttccgttgg actgatggca    1860
gcacactgca atacgagaat tggagaccca accagccaga cagcttcttt tctgctggag    1920
aagactgtgt tgtaatcatt tggcatgaga atggccagtg gaatgatgtt ccctgcaatt    1980
accatctcac ctatacgtgc aagaaaggaa cagtcgcttg cggccagccc cctgttgtag    2040
aaaatgccaa gacctttgga aagatgaaac ctcgttatga aatcaactcc ctgattagat    2100
accactgcaa agatggttc attcaacgtc accttccaac tatccggtgc ttaggaaatg     2160
gaagatgggc tatacctaaa attacctgca tgaacccatc tgcataccaa aggacttatt    2220
ctatgaaata cttaaaaat tcctcatcag caaaggacaa ttcaataaat acatccaaac     2280
```

```
atgatcatcg ttggagccgg aggtggcagg agtcgaggcg ctgatcccta aaatggcgaa    2340
catgtgtttt catcatttca gccaaagtcc taacttcctg tgcctttcct atcacctcga    2400
gaagtaatta tcagttggtt tggattttg gaccaccgtt cagtcatttt gggttgccgt     2460
gctcccaaaa cattttaaat gaaagtattg gcattcaaaa agacagcaga caaaatgaaa    2520
gaaaatgaga gcagaaagta agcatttcca gcctatctaa tttctttagt tttctatttg    2580
cctccagtgc agtccatttc ctaatgtata ccagcctact gtactattta aaatgctcaa    2640
tttcagcacc gatggccatg taaataagat gatttaatgt tgattttaat cctgtatata    2700
aaataaaaag tcacaatgag tttgggcata tttaatgatg attatggagc cttagaggtc    2760
tttaatcatt ggttcggctg cttttatgta gtttaggctg gaaatggttt cacttgctct    2820
ttgactgtca gcaagactga agatggcttt tcctggacag ctagaaaaca caaaatcttg    2880
taggtcattg cacctatctc agccataggt gcagtttgct tctacatgat gctaaaggct    2940
gcgaatggga tcctgatgga actaaggact ccaatgtcga actcttcttt gctgcattcc    3000 ttttttcttca cttacaagaa aggcctgaat ggaggacttt tctgtaacca ggaacatttt    3060
ttaggggtca aagtgctaat aattaactca accaggtcta cttttttaatg ctttcataa    3120 cactaactca taaggttacc gatcaatgca tttcatacgg atatagacct agggctctgg    3180
agggtggggg attgttaaaa cacatgcaaa aaaaaaaaa aaaaaaaaaa aagaaatttt     3240
gtatatataa ccatttaat cttttataaa gttttgaatg ttcatgtatg aatgctgcag    3300
ctgtgaagca tacataaata aatgaagtaa gccatactga tttaatttat tggatgttat    3360
tttccctaag acctgaaaat gaacatagta tgctagttat ttttcagtgt tagccttta     3420 ctttcctcac acaatttgga atcatataat ataggtactt tgtccctgat taaataatgt    3480
gacggataga atgcatcaag tgtttattat gaaaagagtg gaaaagtata tagcttttag    3540 caaaggtgt ttgcccattc taagaaatga gcgaatatat agaaatagtg tgggcatttc     3600
ttcctgttag gtggagtgta tgtgttgaca tttctcccca tctcttccca ctctgttttc    3660
tccccattat ttgaataaag tgactgctga agatgacttt gaatccttat ccacttaatt    3720
taatgtttaa agaaaaacct gtaatggaaa gtaagactcc ttccctaatt tcagtttaga    3780
gcaacttgaa gaagagtaga caaaaaataa aatgcacata gaaaaagaga aaaagggcac    3840
aaagggattg gcccaatatt gattctttt tttataaaacc tcctttggct tagaaggaat    3900
gactctagct acaataatac acagtatgtt taagcaggtt cccttggttg ttgcattaaa    3960
tgtaatccac cttaggtat tttagagcac agaacaacac tgtgttgatc tagtaggttt    4020
ctatttttcc tttctctta caatgcacat aatactttcc tgtatttata tcataacgtg    4080
tatagtgtaa aatgtgaatg acttttttg tgaatgaaaa tctaaaatct ttgtaacttt    4140
ttatatctgc ttttgtttca ccaaagaaac ctaaaatcct tcttttacta cac         4193

<210> SEQ ID NO 5
<211> LENGTH: 7253
<212> TYPE: DNA
<213> ORGANISM: homo sapiens

<400> SEQUENCE: 5
agccgctgcg cccgagctgg cctgcgagtt cagggctcct gtcgctctcc aggagcaacc       60
tctactccgg acgcacaggc attccccgcg ccctccagc cctcgccgcc ctcgccaccg      120 ctccccggccg ccgcgctccg gtacacacag gatccctgct gggcaccaac agctccacca    180
```

```
tggggctggc ctggggacta ggcgtcctgt tcctgatgca tgtgtgtggc accaaccgca    240
ttccagagtc tggcggagac aacagcgtgt tgacatctt tgaactcacc ggggccgccc    300
gcaaggggtc tgggcgccga ctggtgaagg cccccgaccc ttccagccca gctttccgca    360
tcgaggatgc caacctgatc cccctgtgc ctgatgacaa gttccaagac ctggtggatg    420
ctgtgcgggc agaaaagggt ttcctccttc tggcatccct gaggcagatg aagaagaccc    480
ggggcacgct gctggccctg gagcggaaag accactctgg ccaggtcttc agcgtggtgt    540
ccaatggcaa ggcgggcacc ctggacctca gcctgaccgt ccaaggaaag cagcacgtgg    600
tgtctgtgga agaagctctc ctggcaaccg ccagtggaa gagcatcacc ctgtttgtgc    660
aggaagacag ggcccagctg tacatcgact gtgaaaagat ggagaatgct gagttggacg    720
tccccatcca aagcgtcttc accagagacc tggccagcat cgccagactc cgcatcgcaa    780
aggggggcgt caatgacaat ttccagggggg tgctgcagaa tgtgaggttt gtctttggaa    840
ccacaccaga agacatcctc aggaacaaag gctgctccag ctctaccagt gtcctcctca    900
cccttgacaa caacgtggtg aatggttcca gccctgccat ccgcactaac tacattggcc    960
acaagacaaa ggacttgcaa gccatctgcg gcatctcctg tgatgagctg tccagcatgg   1020
tcctggaact caggggcctg cgcaccattg tgaccacgct gcaggacagc atccgcaaag   1080
tgactgaaga gaacaaagag ttggccaatg agctgaggcg gcctccccta tgctatcaca   1140
acggagttca gtacagaaat aacgaggaat ggactgttga tagctgcact gagtgtcact   1200
gtcagaactc agttaccatc tgcaaaaagg tgtcctgccc catcatgccc tgctccaatg   1260
ccacagttcc tgatggagaa tgctgtcctc gctgttggcc cagcgactct gcggacgatg   1320
gctggtctcc atggtccgag tggacctcct gttctacgag ctgtggcaat ggaattcagc   1380
agcgcggccg ctcctgcgat agcctcaaca accgatgtga gggctcctcg gtccagacac   1440
ggacctgcca cattcaggag tgtgacaaga gatttaaaca ggatggtggc tggagccact   1500
ggtccccgtg gtcatcttgt tctgtgacat gtggtgatgg tgtgatcaca aggatccggc   1560
tctgcaactc tcccagcccc cagatgaacg ggaaaccctg tgaaggcgaa gcgcgggaga   1620
ccaaagcctg caagaaagac gcctgcccca tcaatggagg ctgggtcct tggtcaccat   1680 gggacatctg ttctgtcacc tgtggaggag gggtacagaa acgtagtcgt ctctgcaaca   1740
accccacacc ccagtttgga ggcaaggact gcgttggtga tgtaacagaa aaccagatct   1800
gcaacaagca ggactgtcca attgatggat gcctgtccaa tccctgcttt gccggcgtga   1860
agtgtactag ctaccctgat ggcagctgga aatgtggtgc ttgtccccct ggttacagtg   1920
gaaatggcat ccagtgcaca gatgttgatg agtgcaaaga agtgcctgat gcctgcttca   1980
accacaatgg agagcaccgg tgtgagaaca cggaccccgg ctacaactgc ctgccctgcc   2040
ccccacgctt caccggctca cagcccttcg gccagggtgt cgaacatgcc acggccaaca   2100
aacaggtgtg caagcccgt aaccctgca cggatgggac ccacgactgc aacaagaacg   2160
ccaagtgcaa ctacctgggc cactatagcg accccatgta ccgctgcgag tgcaagcctg   2220
gctacgctgg caatggcatc atctgcgggg aggacacaga cctggatggc tggcccaatg   2280
agaacctggt gtgcgtggcc aatgcgactt accactgcaa aaaggataat tgccccaacc   2340
ttcccaactc agggcaggaa gactatgaca aggatggaat tggtgatgcc tgtgatgatg   2400
acgatgacaa tgataaaatt ccagatgaca gggacaactg tccattccat tacaacccag   2460
ctcagtatga ctatgacaga gatgatgtgg gagaccgctg tgacaactgt ccctacaacc   2520
acaacccaga tcaggcagac acagacaaca atgggggaagg agacgcctgt gctgcagaca   2580
```

```
ttgatggaga cggtatcctc aatgaacggg acaactgcca gtacgtctac aatgtggacc    2640
agagagacac tgatatggat ggggttggag atcagtgtga caattgcccc ttggaacaca    2700
atccggatca gctggactct gactcagacc gcattggaga tacctgtgac aacaatcagg    2760
atattgatga agatggccac cagaacaatc tggacaactg tccctatgtg cccaatgcca    2820
accaggctga ccatgacaaa gatggcaagg gagatgcctg tgaccacgat gatgacaacg    2880
atggcattcc tgatgacaag gacaactgca gactcgtgcc caatcccgac cagaaggact    2940
ctgacggcga tggtcgaggt gatgcctgca agatgatttt gaccatgaca gtgtgccag    3000 acatcgatga catctgtcct gagaatgttg acatcagtga gaccgatttc cgccgattcc    3060
agatgattcc tctggacccc aaagggacat cccaaaatga ccctaactgg gttgtacgcc    3120
atcagggtaa agaactcgtc cagactgtca actgtgatcc tggactcgct gtaggttatg    3180
atgagtttaa tgctgtggac ttcagtggca ccttcttcat caacaccgaa agggacgatg    3240
actatgctgg atttgtcttt ggctaccagt ccagcagccg cttttatgtt gtgatgtgga    3300
agcaagtcac ccagtcctac tgggacacca accccacgag ggctcaggga tactcgggcc    3360
tttctgtgaa agttgtaaac tccaccacag ggcctggcga gcacctgcgg aacgccctgt    3420
ggcacacagg aaacaccct ggccaggtgc gcaccctgtg gcatgacct cgtcacatag    3480 gctggaaaga tttcaccgcc tacagatggc gtctcagcca caggccaaag acgggtttca    3540
ttagagtggt gatgtatgaa gggaagaaaa tcatggctga ctcaggaccc atctatgata    3600
aaacctatgc tggtggtaga ctaggggttgt ttgtcttctc tcaagaaatg gtgttcttct    3660
ctgacctgaa atacgaatgt agagatccct aatcatcaaa ttgttgattg aaagactgat    3720
cataaaccaa tgctggtatt gcaccttctg gaactatggg cttgagaaaa ccccaggat    3780 cacttctcct tggcttcctt cttttctgtg cttgcatcag tgtggactcc tagaacgtgc    3840
gacctgcctc aagaaaatgc agttttcaaa aacagactca gcattcagcc tccaatgaat    3900
aagacatctt ccaagcatat aaacaattgc tttggttccc ttttgaaaaa gcatctactt    3960
gcttcagttg ggaaggtgcc cattccactc tgcctttgtc acagagcagg gtgctattgt    4020
gaggccatct ctgagcagtg gactcaaaag catttttcagg catgtcagag aagggaggac    4080
tcactagaat tagcaaacaa aaccaccctg acatcctcct tcaggaacac ggggagcaga    4140
ggccaaagca ctaaggggag ggcgcatacc cgagacgatt gtatgaagaa aatatggagg    4200
aactgttaca tgttcggtac taagtcattt tcaggggatt gaaagactat tgctggattt    4260
catgatgctg actggcgtta gctgattaac ccatgtaaat aggcacttaa atagaagcag    4320
gaaagggaga caaagactgg cttctggact tcctccctga tccccaccct tactcatcac    4380
ctgcagtggc cagaattagg gaatcagaat caaaccagtg taaggcagtg ctggctgcca    4440
ttgcctggtc acattgaaat tggtggcttc attctagatg tagcttgtgc agatgtagca    4500
ggaaaatagg aaaacctacc atctcagtga gcaccagctg cctcccaaag gaggggcagc    4560
cgtgcttata tttttatggt tacaatggca caaaattatt atcaacctaa ctaaaacatt    4620
ccttttctct ttttttcctga attatcatgg agttttctaa ttctctcttt tggaatgtag    4680 attttttta aatgctttac gatgtaaaat atttatttt tacttattct ggaagatctg    4740
gctgaaggat tattcatgga acaggaagaa gcgtaaagac tatccatgtc atctttgttg    4800
agagtcttcg tgactgtaag attgtaaata cagattattt attaactctg ttctgcctgg    4860
aaatttaggc ttcatacgga aagtgtttga gagcaagtag ttgacattta tcagcaaatc    4920
```

```
tcttgcaaga acagcacaag gaaaatcagt ctaataagct gctctgcccc ttgtgctcag    4980
agtggatgtt atgggattct ttttttctct gttttatctt ttcaagtgga attagttggt    5040
tatccatttg caaatgtttt aaattgcaaa gaaagccatg aggtcttcaa tactgtttta    5100
ccccatccct tgtgcatatt tccagggaga aggaaagcat atacactttt ttctttcatt    5160
tttccaaaag agaaaaaaat gacaaaggt gaaacttaca tacaaatatt acctcatttg     5220
ttgtgtgact gagtaaagaa ttttggatc aagcggaaag agtttaagtg tctaacaaac     5280
ttaaagctac tgtagtacct aaaaagtcag tgttgtacat agcataaaaa ctctgcagag    5340
aagtattccc aataaggaaa tagcattgaa atgttaaata caatttctga agttatgtt    5400 tttttctat catctggtat accattgctt tatttttata aattatttc tcattgccat     5460 tggaatagat atctcagatt gtgtagatat gctatttaaa taatttatca ggaaatactg    5520
cctgtagagt tagtatttct attttatat aatgtttgca cactgaattg aagaattgtt    5580
ggttttttct ttttttgtt ttgtttttt ttttttttt tttgctttt gacctcccat        5640 ttttactatt tgccaatacc ttttctagg aatgtgcttt ttttgtaca cattttatc      5700 cattttacat tctaaagcag tgtaagttgt atattactgt ttcttatgta caaggaacaa    5760
caataaatca tatggaaatt tatatttata cttactgtat ccatgcttat tgttctcta    5820 ctggctttat gtcatgaagt atatgcgtaa ataccattca taaatcaata tagcatatac    5880
aaaaataaat tacagtaagt catagcaaca ttcacagttt gtatgtgatt gagaaagact    5940
gagttgctca ggcctaggct tagaatttgc tgcgtttgtg gaataaaaga acaaaatgat    6000
acattagcct gccatatcaa aaacatataa aagagaaatt atccctaagt caagggcccc    6060
cataagaata aaatttctta ttaaggtcat tagatgtcat tgaatccttt tcaaagtgca    6120
gtatgaaaac aaagggaaaa acactgaagc acacgcaact ctcacagcga cattttctga    6180
cccacgaatg atgccttggg tgggcaacac gattgcatgt tgtggagaca cttcggaagt    6240
aaatgtggat gagggaggag ctgtcccttgc aatgttgagc caagcattac agatacctcc    6300
tcttgaagaa ggaataataa gtttaatcaa aaagaagac taaaaaatgt aaaatttgga     6360
aggaatccat aaatgcgtgt gtgtctaaat acaaattatc atgtgaagaa aaggcccaag    6420
tgtaccaata agcagacctt gattttttgga tgggctaatt atgaatgtgg aatactgacc    6480
agttaatttc cagttttaat gaaaacagat caaagaagaa attttatgag taggttaaag    6540
gtctggcttt gaggtctatt aaacactaga aaggactggc tgggtgagat aaaatcttcc    6600
ttgttgattt tcactctcat tctataaata ctcatctttc tgagtagcca tgatcacata    6660
caaatgtaaa ttgccaaatc attttatagt accaaggtga agaagcagga actagaaagt    6720
gttgataata gctgtggagt taggaaaact gatgtgaagg aaataattct ttgaaatggc    6780
aaagaattaa ataccatcat tcattatcag aagagttcaa cgtttgaagt gctgggagat    6840
aattctaatt cattcttgga tagtgaagca aaactgattg aaaataccaa gataagacag    6900
aaaaagtgac tggaaagagg agcttttctt ccaggcatgt tccagtttca ccctaagact    6960
gaccttcaaa taatcaggtt gtactgaaat aaaggacttg ttaaaaatta aaattatgtc    7020
atcgagatga tagcttttttt cctcctccaa cagtttattg tcatgtgttg tgggagagct    7080
cgagtgaaga gcaataaact ccaggtctta taagaatgta catacaataa aggtggtgcc    7140
agcagttttt ttttttctaa agagtcacat gtagaaaagc ctccagtatt aagctcctga    7200
attcattcct taaataaatt ggctctctct ctcttctata aaaaaaaaaa aaa           7253
```

<210> SEQ ID NO 6
<211> LENGTH: 2683
<212> TYPE: DNA
<213> ORGANISM: homo sapiens

<400> SEQUENCE: 6

| | | | | | |
|---|---|---|---|---|---|
| ctgatataga | gcaggcgccg | cgggtcgcag | cacagtgcgg | agaccgcagc | cccggagccc | 60 |
| gggccagggt | ccacctgtcc | ccgcagcgcc | ggctcgcgcc | ctcctgccgc | agccaccgag | 120 |
| ccgccgtcta | gcgccccgac | ctcgccacca | tgagagccct | gctggcgcgc | ctgcttctct | 180 |
| gcgtcctggt | cgtgagcgac | tccaaagtga | gtgcgctctt | gctttgactg | atgctgccca | 240 |
| aggacctctg | atcagcacca | ggggagagga | ggggctgctc | agggagctgg | ggtcctccgg | 300 |
| attccatcca | cagcagggcc | agactctccc | caggaaatgg | gacagggtgg | cagcggaggc | 360 |
| ttgagaacca | cggggggttgg | cactggctgg | caagggagga | agaggccgcc | gggactgccc | 420 |
| cagcctgcgg | gcatctggta | gatgaagctt | gcttgggtca | atccatttct | cctggctgga | 480 |
| aacccatggt | cttccatttg | agaactagat | acgaacaggc | gaactgtgac | tgtctaaatg | 540 |
| gaggaacatg | tgtgtccaac | aagtacttct | ccaacattca | ctggtgcaac | tgcccaaaga | 600 |
| aattcggagg | gcagcactgt | gaaatagata | agtcaaaaac | ctgctatgag | ggaatggtc | 660 |
| acttttaccg | aggaaaggcc | agcactgaca | ccatgggccg | gccctgcctg | ccctggaact | 720 |
| ctgccactgt | ccttcagcaa | acgtaccatg | cccacagatc | tgatgctctt | cagctgggcc | 780 |
| tggggaaaca | taattactgc | aggaacccag | acaaccggag | gcgaccctgg | tgctatgtgc | 840 |
| aggtgggcct | aaagccgctt | gtccaagagt | gcatggtgca | tgactgcgca | gatggaaaaa | 900 |
| agccctcctc | tcctccagaa | gaattaaaat | ttcagtgtgg | ccaaaagact | ctgaggcccc | 960 |
| gctttaagat | tattggggga | gaattcacca | ccatcgagaa | ccagccctgg | tttgcggcca | 1020 |
| tctacaggag | gcaccggggg | ggctctgtca | cctacgtgtg | tggaggcagc | ctcatcagcc | 1080 |
| cttgctgggt | gatcagcgcc | acacactgct | tcattgatta | cccaaagaag | gaggactaca | 1140 |
| tcgtctacct | gggtcgctca | aggcttaact | ccaacacgca | agggagatg | aagtttgagg | 1200 |
| tggaaaacct | catcctacac | aaggactaca | gcgctgacac | gcttgctcac | cacaacgaca | 1260 |
| ttgccttgct | gaagatccgt | tccaaggagg | gcaggtgtgc | gcagccatcc | cggactatac | 1320 |
| agaccatctg | cctgccctcg | atgtataacg | atcccagtt | tggcacaagc | tgtgagatca | 1380 |
| ctggctttgg | aaaagagaat | tctaccgact | atctctatcc | ggagcagctg | aaaatgactg | 1440 |
| ttgtgaagct | gatttcccac | cgggagtgtc | agcagcccca | ctactacggc | tctgaagtca | 1500 |
| ccaccaaaat | gctgtgtgct | gctgacccac | agtggaaaac | agattcctgc | cagggagact | 1560 |
| caggggggacc | cctcgtctgt | tccctccaag | gccgcatgac | tttgactgga | attgtgagct | 1620 |
| ggggccgtga | atgtgccctg | aaggacaagc | caggcgtcta | cacgagagtc | tcacacttct | 1680 |
| taccctggat | ccgcagtcac | accaaggaag | agaatggcct | ggccctctga | gggtccccag | 1740 |
| ggaggaaacg | ggcaccaccc | gctttcttgc | tggttgtcat | ttttgcagta | gagtcatctc | 1800 |
| catcagctgt | aagaagagac | tgggaagata | ggctctgcac | agatggattt | gcctgtgcca | 1860 |
| cccaccaggg | cgaacgacaa | tagctttacc | ctcaggcata | ggcctgggtg | ctggctgccc | 1920 |
| agacccctct | ggccaggatg | gaggggtggt | cctgactcaa | catgttactg | accagcaact | 1980 |
| tgtcttttc | tggactgaag | cctgcaggag | ttaaaaaggg | cagggcatct | cctgtgcatg | 2040 |
| ggtgaaggga | gagccagctc | ccccgacggt | gggcatttgt | gaggcccatg | gttgagaaat | 2100 |
| gaataatttc | ccaattagga | agtgtaacag | ctgaggtctc | ttgagggagc | ttagccaatg | 2160 |

| | |
|---|---|
| tgggagcagc ggtttgggga gcagagacac taacgacttc agggcagggc tctgatattc | 2220 |
| catgaatgta tcaggaaata tatatgtgtg tgtatgtttg cacacttgtg tgtgggctgt | 2280 |
| gagtgtaagt gtgagtaaga gctggtgtct gattgttaag tctaaatatt tccttaaact | 2340 |
| gtgtggactg tgatgccaca cagagtggtc tttctggaga ggttataggt cactcctggg | 2400 |
| gcctcttggg tcccccacgt gacagtgcct gggaatgtat tattctgcag catgacctgt | 2460 |
| gaccagcact gtctcagttt cactttcaca tagatgtccc tttcttggcc agttatccct | 2520 |
| tccttttagc ctagttcatc caatcctcac tgggtggggt gaggaccact cctgtacact | 2580 |
| gaatatttat atttcactat ttttatttat attttgtaa ttttaaataa aagtgatcaa | 2640 |
| taaaatgtga tttttctgat gacaaaaaaa aaaaaaaaa aaa | 2683 |

<210> SEQ ID NO 7
<211> LENGTH: 2137
<212> TYPE: DNA
<213> ORGANISM: homo sapiens

<400> SEQUENCE: 7

| | |
|---|---|
| cacagagagg ctgggagagc aagccggaga gaagagagag cccggccaga cccactgcga | 60 |
| tgagacagga cgcgcccaag cccactcctg cagcctgccg ctgctccggc ctggcccgga | 120 |
| gggtgctgac catcgccttc gccctgctca tcctgggcct catgacctgg gcctacgccg | 180 |
| ccggggtgcc gctggcctcc gatcgctacg gcctcctggc cttcggcctc tacggggcct | 240 |
| tcctttcagc gcacctggtg gcgcagagcc tcttcgcgta cctggagcac cggcgggtgg | 300 |
| cggcggcggc gcggggggccg ctggatgcag ccaccgcgcg cagtgtggcg ctgaccatct | 360 |
| ccgcctacca ggaggacccc gcgtacctgc gccagtgcct ggcgtccgcc cgcgccctgc | 420 |
| tgtaccgcg cgcgcggctg cgcgtcctca tggtggtgga tggcaaccgc gccgaggacc | 480 |
| tctacatggt cgacatgttc cgcgaggtct tcgctgacga ggaccccgcc acgtacgtgt | 540 |
| gggacggcaa ctaccaccag ccctgggaac ccgcggcggc gggcgcggtg ggcgccggag | 600 |
| cctatcggga ggtggaggcg gaggatcctg ggcggctggc agtggaggcg ctggtgagga | 660 |
| ctcgcaggtg cgtgtgcgtg gcgcagcgct ggggcggcaa gcgcgaggtc atgtacacag | 720 |
| ccttcaaggc gctcggagat cggtggact acgtgcaggt ctgtgactcg gacacaaggt | 780 |
| tggaccccat ggcactgctg gagctcgtgc gggtactgga cgaggacccc cgggtagggg | 840 |
| ctgttggtgg ggacgtgcgg atccttaacc ctctggactc ctgggtcagc ttcctaagca | 900 |
| gcctgcgata ctgggtagcc ttcaatgtgg agcgggcttg tcagagctac ttccactgtg | 960 |
| tatcctgcat cagcggtcct ctaggcctat ataggaataa cctcttgcag cagtttcttg | 1020 |
| aggcctggta caaccagaag ttcctgggta cccactgtac ttttggggat gaccggcacc | 1080 |
| tcaccaaccg catgctcagc atgggttatg ctaccaagta cacctccagg tcccgctgct | 1140 |
| actcagagac gccctcgtcc ttcctgcggt ggctgagcca gcagacacgc tggtccaagt | 1200 |
| cgtacttccg tgagtggctg tacaacgcgc tctggtggca ccggcaccat gcgtggatga | 1260 |
| cctacgaggc ggtggtctcc ggcctgttcc ccttcttcgt ggcggccact gtgctgcgtc | 1320 |
| tgttctacgc gggccgccct gggcgctgc tgtgggtgct gctgtgcgtg cagggcgtgg | 1380 |
| cactggccaa ggcggccttc gcggcctggc tgcggggctg cctgcgcatg gtgcttctgt | 1440 |
| cgctctacgc gccctctac atgtgtggcc tcctgcctgc caagttcctg gcgctagtca | 1500 |
| ccatgaacca gagtggctgg ggcacctcgg gccggcggaa gctggccgct aactacgtcc | 1560 |
| ctctgctgcc cctggcgctc tgggcgctgc tgctgcttgg gggcctggtc cgcagcgtag | 1620 |

```
cacacgaggc cagggccgac tggagcggcc cttcccgcgc agccgaggcc taccacttgg    1680 ccgcggggc cggcgcctac gtgggctact gggtggccat gttgacgctg tactgggtgg    1740
gcgtgcggag gctttgccgg cggcggaccg ggggctaccg cgtccaggtg tgagtccagc    1800
cacgcggatg ccgcctcaag ggtcttcagg ggaggccaga ggagagctgc tgggccccga    1860
gccacgaact tgctgggtgg ttctctgggc ctcagtttcc ctcctctgca aaacgagggg    1920
gtcagcccaa gattcttcag tctggactat attgggactg ggacttctgg gtctccaggg    1980
agggtattta ttggtcaggg tgtgggatct gaggagtgga gggaaagggt cctgctttct    2040
cctcgttctt atttaatctc catttctact gtgtgatcag gatgtaataa agaattttat    2100
ttattttcaa aaaaaaaaaa aaaaaaaaaa aaaaaaa                             2137
```

<210> SEQ ID NO 8
<211> LENGTH: 1629
<212> TYPE: DNA
<213> ORGANISM: homo sapiens

<400> SEQUENCE: 8

```
attcatgaaa atccactact ccagacagac ggctttggaa tccaccagct acatccagct      60
ccctgaggca gagttgagaa tggagagaat gttacctctc ctggctctgg ggctcttggc     120
ggctgggttc tgccctgctg tcctctgcca cctaacagcc ccacttgacg aggagaatct     180
gacccaggag aaccaagacc gagggacaca cgtggacctc ggattagcct ccgccaacgt     240
ggacttcgct ttcagcctgt acaagcagtt agtcctgaag gccccgtata gaatgtcat     300 cttctcccca ctgagcatct ccaccgcctt ggccttcctg tctctggggg cccataatac     360 cacccctgaca gagattctca aaggcctcaa gttcaacctc acggagactt ctgaggcaga    420
aattcaccag agcttccagc acctcctgcg caccctcaat cagtccagcg atgagctgca    480
gctgagtatg ggaaatgcca tgtttgtcaa agagcaactc agtctgctgg acaggttcac    540
ggaggatgcc aagaggctgt atggctccga ggcctttgcc actgactttc aggactcagc    600
tgcagctaag aagctcatca cgactacgt gaagaatgga actaggggga aaatcacaga    660
tctgatcaag gaccttgact cgcagacaat gatggtcctg gtgaattaca tcttctttaa    720
agccaaatgg gagatgccct ttgacccca agatactcat cagtcaaggt tctacttgag    780
caagaaaaag tgggtaatgg tgcccatgat gagtttgcat cacctgacta taccttactt    840
ccgggacgag gagctgtcct gcaccgtggt ggagctgaag tacacaggca atgccagcgc    900
actcttcatc ctccctgatc aagacaagat ggaggaagtg gaagccatgc tgctcccaga    960
gaccctgaag cggtggagag actctctgga gttcagagag ataggtgagc tctacctgcc   1020
aaagttttcc atctcgaggg actataacct gaacgacata cttctccagc tgggcattga   1080
ggaagccttc accagcaagg ctgacctgtc agggatcaca ggggccagga acctagcagt   1140
ctcccaggtg gtccataagg ctgtgcttga tgtatttgag gagggcacag aagcatctgc   1200
tgccacagca gtcaaaatca ccctccttc tgcattagtg gagacaagga ccattgtgcg   1260
tttcaacagg cccttcctga tgatcattgt ccctacagac acccagaaca tcttcttcat   1320
gagcaaagtc accaatccca gcaagcctta gagcttgcca tcaagcagtg gggctctcag   1380
taaggaactt ggaatgcaag ctggatgcct gggtctctgg gcacagcctg cccctgtgc   1440 accgagtggc catggcatgt gtgggcccgt ctgcttatcc ttgaaggtg acagcgattc   1500 cctgtgtagc tctcacatgc acaggggccc atggactctt cagtctggag ggtcctgggc   1560
```

```
ctcctgacag caataaataa tttcgttgga aaaaaaaaaa aaaaaaaaaa aaaaaaaaaa    1620
aaaaaaaaa                                                            1629

<210> SEQ ID NO 9
<211> LENGTH: 3207
<212> TYPE: DNA
<213> ORGANISM: homo sapiens

<400> SEQUENCE: 9
ggcccacaga ggagcacagc tgtgtttggc tgcagggcca agagcgctgt caagaagacc      60
cacacgcccc cctccagcag ctgaattcct gcagctcagc agccgccgcc agagcaggac     120
gaaccgccaa tcgcaaggca cctctgagaa cttcaggatg cagatgtctc cagccctcac     180
ctgcctagtc ctgggcctgg cccttgtctt tggtgaaggg tctgctgtgc accatccccc     240
atcctacgtg gcccacctgg cctcagactt cggggtgagg gtgttttcagc aggtggcgca     300 ggcctccaag gaccgcaacg tggttttctc accctatggg gtggcctcgg tgttggccat     360
gctccagctg acaacaggag gagaaaccca gcagcagatt caagcagcta tgggattcaa     420
gattgatgac aagggcatgg ccccgccct ccggcatctg tacaaggagc tcatggggcc     480
atggaacaag gatgagatca gcaccacaga cgcgatcttc gtccagcggg atctgaagct     540
ggtccagggc ttcatgcccc acttcttcag gctgttccgg agcacggtca agcaagtgga     600
cttttcagag gtgagagag ccagattcat catcaatgac tggtgaaga cacacacaaa     660 aggtatgatc agcaacttgc ttgggaaagg agccgtggac cagctgacac ggctggtgct     720
ggtgaatgcc ctctacttca cggccagtg aagactccc ttccccgact ccagcaccca     780
ccgccgcctc ttccacaaat cagacggcag cactgtctct gtgcccatga tggctcagac     840
caacaagttc aactatactg agttcaccac gcccgatggc cattactacg acatcctgga     900
actgccctac cacggggaca ccctcagcat gttcattgct gccccttatg aaaaagaggt     960
gcctctctct gccctcacca acattctgag tgcccagctc atcagccact ggaaaggcaa    1020
catgaccagg ctgccccgcc tcctggttct gcccaagttc tccctggaga ctgaagtcga    1080
cctcaggaag cccctagaga acctgggaat gaccgacatg ttcagacagt ttcaggctga    1140
cttcacgagt cttttcagacc aagagcctct ccacgtcgcg caggcgctgc agaaagtgaa    1200
gatcgaggtg aacgagagtg gcacggtggc ctcctcatcc acagctgtca tagtctcagc    1260
ccgcatggcc cccgaggaga tcatcatgga cagacccttc ctctttgtgg tccggcacaa    1320
ccccacagga acagtccttt tcatgggcca agtgatggaa ccctgaccct ggggaaagac    1380
gccttcatct gggacaaaac tggagatgca tcgggaaaga agaaactccg aagaaaagaa    1440
ttttagtgtt aatgactctt tctgaaggaa gagaagacat ttgccttttg ttaaaagatg    1500
gtaaaccaga tctgtctcca agaccttggc ctctccttgg aggacctta ggtcaaactc     1560 cctagtctcc acctgagacc ctgggagaga agtttgaagc acaactccct taaggtctcc    1620
aaaccagacg gtgacgcctg cggggaccatc tggggcacct gcttccaccc gtctctctgc    1680
ccactcgggt ctgcagacct ggttcccact gaggcccttt gcaggatgga actacggggc    1740
ttacaggagc ttttgtgtgc ctggtagaaa ctatttctgt tccagtcaca ttgccatcac    1800
tcttgtactg cctgccaccg cggaggaggc tggtgacagg ccaaaggcca gtggaagaaa    1860 cacccttttca tctcagagtc cactgtggca ctggccaccc ctcccagta caggggtgct    1920 gcaggtggca gagtgaatgt ccccccatcat gtggcccaac tctcctggcc tggccatctc    1980
cctccccaga aacagtgtgc atgggttatt ttggagtgta ggtgacttgt ttactcattg    2040
```

```
aagcagattt ctgcttcctt ttattttat aggaatagag gaagaaatgt cagatgcgtg        2100
cccagctctt cacccccaa tctcttggtg gggagggtg tacctaaata tttatcatat          2160
ccttgccctt gagtgcttgt tagagagaaa gagaactact aaggaaaata atattattta        2220
aactcgctcc tagtgtttct ttgtggtctg tgtcaccgta tctcaggaag tccagccact        2280
tgactggcac acacccctcc ggacatccag cgtgacggag cccacactgc caccttgtgg       2340
ccgcctgaga ccctcgcgcc cccgcgcccc ctcttttcc ccttgatgga aattgaccat         2400
acaatttcat cctccttcag gggatcaaaa ggacggagtg ggggacaga gactcagatg        2460 aggacagagt ggtttccaat gtgttcaata gatttaggag cagaaatgca aggggctgca      2520
tgacctacca ggacagaact ttccccaatt acagggtgac tcacagccgc attggtgact      2580
cacttcaatg tgtcatttcc ggctgctgtg tgtgagcagt ggacacgtga ggggggggtg    2640
ggtgagagag acaggcagct cggattcaac taccttagat aatatttctg aaaacctacc     2700
agccagaggg tagggcacaa agatggatgt aatgcacttt gggaggccaa ggcgggagga     2760
ttgcttgagc ccaggagttc aagaccagcc tgggcaacat accaagaccc ccgtctcttt    2820
aaaaatatat atattttaaa tacttaaa tatatatttc taatatcttt aaatatatat       2880
atatatttta aagaccaatt tatgggagaa ttgcacacag atgtgaaatg aatgtaatct     2940
aatagaagcc taatcagccc accatgttct ccactgaaaa atcctctttc tttgggtttt    3000
ttctttcttt cttttttgat tttgcactgg acggtgacgt cagccatgta caggatccac    3060
aggggtggtg tcaaatgcta ttgaaattgt gttgaattgt atgcttttc acttttgata     3120 aataaacatg taaaatgtt tcaaaaaaat aataaaataa ataaatacga agaatatgtc    3180
aggacagtca aaaaaaaaa aaaaaaa                                            3207
```

<210> SEQ ID NO 10
<211> LENGTH: 1906
<212> TYPE: DNA
<213> ORGANISM: homo sapiens

<400> SEQUENCE: 10

```
aaagcaagga tgagtcaagc tgcgggtgat ccaaacaaac actgtcactc tttaaaagct        60
gcgctcccga ggttggacct acaaggaggc aggcaagaca gcaaggcata gagcaacat        120 agagctaagt aaagccagtg gaaatgaaga gtcttccaat cctactgttg ctgtgcgtgg      180
cagtttgctc agcctatcca ttggatggag ctgcaagggg tgaggacacc agcatgaacc     240
ttgttcagaa atatctagaa aactactacg acctcaaaaa agatgtgaaa cagtttgtta    300
ggagaaagga cagtggtcct gttgttaaaa aaatccgaga aatgcagaag ttccttggat    360
tggaggtgac ggggaagctg gactccgaca ctctggaggt gatgcgcaag cccaggtgtg     420
gagttcctga tgttggtcac ttcagaacct ttcctggcat cccgaagtgg aggaaaaccc     480
accttacata caggattgtg aattatacac cagatttgcc aaaagatgct gttgattctg     540
ctgttgagaa agctctgaaa gtctgggaag aggtgactcc actcacattc tccaggctgt    600
atgaaggaga ggctgatata atgatctctt ttgcagttag agaacatgga gacttttacc      660
cttttgatgg acctggaaat gttttggccc atgcctatgc cctgggcca gggattaatg       720 gagatgccca ctttgatgat gatgaacaat ggacaaagga tacaacaggg accaatttat      780
ttctcgttgc tgctcatgaa attggccact ccctgggtct ctttcactca gccaacactg      840
aagctttgat gtacccactc tatcactcac tcacagacct gactcggttc cgcctgtctc      900
```

| | |
|---|---|
| aagatgatat aaatggcatt cagtccctct atggacctcc ccctgactcc cctgagaccc | 960 |
| ccctggtacc cacggaacct gtccctccag aacctgggac gccagccaac tgtgatcctg | 1020 |
| cttttgtcctt tgatgctgtc agcactctga ggggagaaat cctgatcttt aaagacaggc | 1080 |
| acttttggcg caaatccctc aggaagcttg aacctgaatt gcatttgatc tcttcatttt | 1140 |
| ggccatctct tccttcaggc gtggatgccg catatgaagt tactagcaag gacctcgttt | 1200 |
| tcattttaa aggaaatcaa ttctgggcta tcagaggaaa tgaggtacga gctggatacc | 1260 |
| caagaggcat ccacaccca ggtttccctc aaccgtgag gaaaatcgat gcagccattt | 1320 |
| ctgataagga aaagaacaaa acatatttct ttgtagagga caaatactgg agatttgatg | 1380 |
| agaagagaaa ttccatggag ccaggctttc ccaagcaaat agctgaagac tttccaggga | 1440 |
| ttgactcaaa gattgatgct gttttttgaag aatttgggtt cttttatttc tttactggat | 1500 |
| cttcacagtt ggagtttgac ccaaatgcaa agaaagtgac acacactttg aagagtaaca | 1560 |
| gctggcttaa ttgttgaaag agatatgtag aaggcacaat atgggcactt taaatgaagc | 1620 |
| taataattct tcacctaagt ctctgtgaat tgaaatgttc gttttctcct gcctgtgctg | 1680 |
| tgactcgagt cacactcaag ggaacttgag cgtgaatctg tatcttgccg gtcatttta | 1740 |
| tgttattaca gggcattcaa atgggctgct gcttagcttg caccttgtca catagagtga | 1800 |
| tctttcccaa gagaagggga agcactcgtg tgcaacagac aagtgactgt atctgtgtag | 1860 |
| actatttgct tatttaataa agacgatttg tcagttattt tatctt | 1906 |

<210> SEQ ID NO 11
<211> LENGTH: 5676
<212> TYPE: DNA
<213> ORGANISM: homo sapiens

<400> SEQUENCE: 11

| | |
|---|---|
| atgcttctgc tgggcatcct aaccctggct ttcgccgggc gaaccgctgg aggctctgag | 60 |
| ccagagcggg aggtagtcgt tcccatccga ctggacccgg acattaacgg ccgccgctac | 120 |
| tactggcggg gtcccgagga ctccggggat cagggactca ttttcagat cacagcattt | 180 |
| caggaggact tttacctaca cctgacgccg gatgctcagt tcttggctcc cgccttctcc | 240 |
| actgagcatc tgggcgtccc cctccagggg ctcaccgggg gctcttcaga cctgcgacgc | 300 |
| tgcttctatt ctggggacgt gaacgccgag ccggactcgt tcgctgctgt gagcctgtgc | 360 |
| ggggggctcc gcggagcctt tggctaccga ggcgccgagt atgtcattag cccgctgccc | 420 |
| aatgctagcg cgccggcggc gcagcgcaac agccagggcg cacaccttct ccagcgccgg | 480 |
| ggtgttccgg gcgggccttc cggagacccc acctctcgct gcggggtggc ctcgggctgg | 540 |
| aaccccgcca tcctacgggc cctgaccct tacaagccgc ggcgggcggg cttcggggag | 600 |
| agtcgtagcc ggcgcaggtc tgggcgcgcc aagcgtttcg tgtctatccc gcggtacgtg | 660 |
| gagacgctgg tggtcgcgga cgagtcaatg gtcaagttcc acggcgcgga cctgaacat | 720 |
| tatctgctga cgctgctggc aacggcggcg cgactctacc gccatcccag catcctcaac | 780 |
| cccatcaaca tcgttgtggt caaggtgctg cttcttagag atcgtgactc cgggcccaag | 840 |
| gtcaccggca atgcggccct gacgctcgcg aacttctgtg cctggcagaa gaagctgaac | 900 |
| aaagtgagtg acaagcaccc cgagtactgg gacactgcca tcctcttcac caggcaggac | 960 |
| ctgtgtggag ccaccacctg tgacaccctg gcatggctg atgtgggtac catgtgtgac | 1020 |
| cccaagagaa gctgctctgt cattgaggac gatgggcttc atcagccctt caccactgcc | 1080 |
| cacgagctgg gccacgtgtt caacatgccc catgacaatg tgaaagtctg tgaggaggtg | 1140 |

-continued

```
tttgggaagc tccgagccaa ccacatgatg tccccgaccc tcatccagat cgaccgtgcc    1200
aacccctggt cagcctgcag tgctgccatc atcaccgact tcctggacag cgggcacggt    1260
gactgcctcc tggaccaacc cagcaagccc atctccctgc ccgaggatct gccgggcgcc    1320
agctacaccc tgagccagca gtgcgagctg gcttttggcg tgggctccaa gccctgtcct    1380
tacatgcagt actgcaccaa gctgtggtgc accgggaagg ccaagggaca gatggtgtgc    1440
cagacccgcc acttcccctg ggccgatggc accagctgtg gcgagggcaa gctctgcctc    1500 aaagggcct gcgtggagag acacaacctc aacaagcaca gggtggatgg ttcctgggcc    1560
aaatgggatc cctatggccc ctgctcgcgc acatgtggtg gggcgtgca gctggccagg    1620 aggcagtgca ccaaccccac ccctgccaac gggggcaagt actgcgaggg agtgagggtg    1680
aaataccgat cctgcaatct ggagccctgc cccagctcag cctccggaaa gagcttccgg    1740
gaggagcagt gtgaggcttt caacggctac aaccacagca ccaaccggct cactctcgcc    1800
gtggcatggg tgcccaagta ctccggcgtg tctccccggg acaagtgcaa gctcatctgc    1860
cgagccaatg gcactggcta cttctatgtg ctggcaccca aggtggtgga cggcacgctg    1920
tgctctcctg actccacctc cgtctgtgtc caaggcaagt gcatcaaggc tggctgtgat    1980
gggaacctgg gctccaagaa gagattcgac aagtgtgggg tgtgtgggg agacaataag    2040 agctgcaaga aggtgactgg actcttcacc aagcccatgc atggctacaa tttcgtggtg    2100 gccatcccg caggcgcctc aagcatcgac atccgccagc gcggttacaa agggctgatc    2160
ggggatgaca actacctggc tctgaagaac agccaaggca agtacctgct caacgggcat    2220
ttcgtggtgt cggcggtgga gcgggacctg gtggtgaagg gcagtctgct gcggtacagc    2280
ggcacgggca gcggtgga gagcctgcag gcttcccggc ccatcctgga gccgctgacc    2340
gtggaggtcc tctccgtggg gaagatgaca ccgcccgggg tccgctactc cttctatctg    2400
cccaaagagc ctcgggagga caagtcctct catcccaagg accccgggg accctctgtc    2460 ttgcacaaca gcgtcctcag cctctccaac caggtggagc agccggacga caggcccct    2520 gcacgctggg tggctggcag ctggggcg tgctccgcga gctgcggcag tggcctgcag    2580
aagcgggcgg tggactgccg gggctccgcc gggcagcgca cggtccctgc ctgtgatgca    2640
gcccatcggc ccgtggagac acaagcctgc ggggagccct gccccacctg ggagctcagc    2700
gcctggtcac cctgctccaa gagctgcggc cggggatttc agaggcgctc actcaagtgt    2760
gtgggccacg gaggccggct gctggcccgg gaccagtgca acttgcaccg caagccccag    2820
gagctggact tctgcgtcct gaggccgtgc tgagtggggt catcgctttc tccccctcac    2880
tctccacccc actgatatgc cagcgttctg ccagctggag tagcgggcag aggacggtgg    2940 ccagggctc acgccacgat gtcacccaca tccgggaca aggaccatgg gctgggcga    3000 gaggttccct cctcctcct ggactgggca gagggaagcc caggaactcc cgcacagtct    3060
acctcaggcc ccgctcctcg ggccggttgc ggggagaggc tttgaggtgc agggcagaag    3120
gtgctgaggc ccagtttcca aggaacttgg aggatgggca ccttccaggc agaacttcag    3180
ggaccccggc cccagaacg gaggccacag gctgctggaa gagccatgtc ccagcagctt    3240
ggcaccctca ggtgggccca tgggctctga gccgtgtctg aacgaggcag gttttcacg    3300 gtgcttttag cccacttcc tttttgaact gacatggact aagcaataaa agctggctgg    3360
ggctgggcag aagccacggg gagagtgaga ttagggcccc tggagcctgg cactccacct    3420
tggaagacgt ggacgtgcac agggagtccc gaggtttctc atcctgcact cttggccctc    3480
```

```
ctataaagaa gcagcctctc cttcctctga tgtgcagggt gtaggactag tggtagggct      3540
gccacggaag tgtcctctga ggctctgcag gtagcgggga aagccagtag ggagtctgct      3600
gtcttcttca agatggagcc ggccattaca gaaagatgtt gacatttgct aggggctatg      3660
cagtctgtgg ctgatgcagg gagttttcag aaagttctgg agggttctgc tgtcactgga      3720
ctggggttgg tgctgagctc tgggcctggc tttgggagat gtcaccctgg gatagggagg      3780
aggaagctgc atttctaatg gcttcctcct ccagagaggc acgtatatgc aggctgacat      3840
ccgagggtct gtgtcgcctc agacagccct gacagtggcc acagtccgt acccattgtg       3900
agggctggg gcatgcctag gagggctagg tgctgaacat ctatgtgcct ataaactcgt       3960
cttcgttcca aacagctact gctgtctgcc ctgggcacgt cacgttgcat cctaggcctt      4020
agcttctcca ctgttttgcta cctcagatta tgccctctgg gaaccccagcc gtatccctcc   4080
cctaggacag tggtgacctg gtccttccac cacactcagt ctttggagag cgagctgtcc     4140
agccacagaa atgagggtgt ggtgcgtggc ttcctgctcc ccacagccca gcccctgtt      4200
ggggctccaa agccgaagac agggcctctt cagactcctt gggagtaggt ttcaggaggc     4260
accaagaatc aatgactgac ccaggggggcc tggcagccac tagtatgaac tgctggagac    4320
ctgtctgtct tatagacatg tcaggaaaat agaaacaggc attttctcta gctccaagtg    4380
gggagatatt ttggggtcac agcttctttg gctaagcagg gtgtttcttg aaggttcaga    4440
tgccccactg tgtacatggg atattctgct tctgagtgta ggtgatgaat ccaggtcctc    4500
agtggagaat tttctggagc taagatcaaa gcatgtgtct tcctgggaga aagagttcc     4560
gttcttttat gtgggtttcc ctaatagtca gaatccacaa accagccagc cagccagcca   4620
agcctctgcg atgatgttct catccggtct aacgctgggc tggaaacctt ggacagagtt   4680
catgcggggg cagaggggggt gccagtctct gaggcagggc tgcagtcacc cctgaagaac   4740
taagtgaaca ggaaccccctc tgtgccagtg accactgtgg ggctaaaggg acaaaaagga   4800
ccagggtacc aggcagaagc agatccttga tagctgacga cagcactgcg ccctgtgctt    4860
ggtgcactcc ctccttcagg aggagagggt ggcatggggt ctgtgcggga tggcagggg    4920
attgggtggg tgggaagaga ggtgccatcg gtagaggct ggcctccagt agaggagagc     4980
agcttttgcc atcagtcact ttacaaacca tttcaaggaa ggacaacctc tctggctcct    5040
gacacaagcc aggcctcggt gcttttatct gttgtggtgg ttttttcttct ttccctttt    5100
aaaagacgca tgaccaagac aacctaggga gtttgtcttg cttgcctttg actatttcct    5160
taatccaacc atgctctcga gggctgagca gagactagac tcaaggcaca ggtttctggt   5220
gatggagtaa agttacagcg gtatctcatg tctacacaag aagaggaacg ttctgaaagc   5280
tccaacaact tcttgagggg gatggaccaa tacagctttg ggctcaggat tcccctagcct  5340
cctctgccca tcgcgtgcac tgattggagg agtctggccc aaacactctc atatgaacct    5400
cgacatgctg gagtggggtc tggcaggagc tgatgacagt ttgagggact tgagtgtccc   5460
tagcctggca gttggctccc ggaagcacta gacactgaca ctcattggta gaccctcccct  5520
ccccgccgtt gtgtttggtt cttttgcact ccatgtactg cagaaggatg gaaggacctg    5580
ggtgctggct gggctgtgta tactgtgtat acaaggagc tggctgctga ggtgaccaca    5640
gccttctcct aataaagctg taagtatta aaacct                               5676
```

<210> SEQ ID NO 12
<211> LENGTH: 1391
<212> TYPE: DNA
<213> ORGANISM: homo sapiens

<400> SEQUENCE: 12

```
acacaccctg acccgcatcg ccctgggtct ctcgagcctg ctgcctgctc ccccgcccca    60
ccagccatgg tggtttctgg agcgccccca gccctgggtg ggggctgtct cggcaccttc   120
acctccctgc tgctgctggc gtcgacagcc atcctcaatg cggccaggat acctgttccc   180
ccagcctgtg ggaagcccca gcagctgaac cgggttgtgg gcggcgagga cagcactgac   240
agcgagtggc cctggatcgt gagcatccag aagaatggga cccaccactg cgcaggttct   300
ctgctcacca gccgctgggt gatcactgct gcccactgtt tcaaggacaa cctgaacaaa   360
ccatacctgt tctctgtgct gctgggggcc tggcagctgg ggaaccctgg ctctcggtcc   420
cagaaggtgg gtgttgcctg ggtggagccc caccctgtgt attcctggaa ggaaggtgcc   480
tgtgcagaca ttgccctggt gcgtctcgag cgctccatac agttctcaga gcgggtcctg   540
cccatctgcc tacctgatgc ctctatccac ctccctccaa acacccactg ctggatctca   600
ggctggggga gcatccaaga tggagttccc ttgccccacc ctcagaccct gcagaagctg   660
aaggttccta tcatcgactc ggaagtctgc agccatctgt actggcgggg agcaggacag   720
ggacccatca ctgaggacat gctgtgtgcc ggctacttgg aggggagcg ggatgcttgt   780
ctgggcgact ccggggggccc cctcatgtgc caggtggacg gcgcctggct gctggccggc   840
atcatcagct ggggcgaggg ctgtgccgag cgcaacaggc ccgggtcta catcagcctc   900
tctgcgcacc gctcctgggt ggagaagatc gtgcaagggg tgcagctccg cgggcgcgct   960
caggggggtg gggccctcag ggcaccgagc cagggctctg gggccgccgc gcgctcctag  1020
ggcgcagcgg gacgcggggc tcggatctga aaggcggcca gatccacatc tggatctgga  1080
tctgcggcgg cctcgggcgg tttccccgc cgtaaatagg ctcatctacc tctacctctg  1140
ggggcccgga cggctgctgc ggaaaggaaa ccccctcccc gacccgcccg acggcctcag  1200
gccccgcctc caaggcatca ggccccgccc aacggcctca tgtccccgcc ccacgactt   1260
ccggccccgc ccgggcccc agcgcttttg tgtatataaa tgttaatgat ttttataggt  1320
atttgtaacc ctgcccacat atcttattta ttcctccaat ttcaataaat tatttattct  1380
ccagtgaaaa a                                                      1391
```

<210> SEQ ID NO 13
<211> LENGTH: 4461
<212> TYPE: DNA
<213> ORGANISM: homo sapiens

<400> SEQUENCE: 13

```
agtccagaca accggcttcc agctggggct ggggaaaggg ggttggaggg gtgcgccccc    60
cccccacgcc cctagggggt gggggacgcg ggctcagagt tccagggacc caggaatgcc   120
ccccgccag ccccctcggc aggcggggg agggctcagc cgggagtttg gcaaactcct   180
ccccgcgttg agtcattcgc ctctgggagg tttaggaagc ggctccgggt cggtggcccc   240
aggacaggga agagcgggcg ctatggggag ccggacgcca gagtcccctc tccacgccgt   300
gcagctgcgc tggggccccc ggcgccgacc ccgctgctg ccgctgctgt tgctgctgct   360
gccgccgcca cccagggtcg ggggcttcaa cttagacgcg gaggccccag cagtactctc   420
ggggccccccg ggctccttct tcggattctc agtggagttt taccggccgg gaacagacgg   480
ggtcagtgtg ctggtgggag cacccaaggc taataccagc cagccaggag tgctgcaggg   540
tggtgctgtc tacctctgtc cttggggtgc cagccccaca cagtgcaccc ccattgaatt   600
```

```
tgacagcaaa ggctctcggc tcctggagtc ctcactgtcc agctcagagg gagaggagcc      660
tgtggagtac aagtccttgc agtggttcgg ggcaacagtt cgagcccatg gctcctccat      720
cttggcatgc gctccactgt acagctggcg cacagagaag gagccactga gcgaccccgt      780
gggcacctgc tacctctcca cagataactt cacccgaatt ctggagtatg caccctgccg      840
ctcagatttc agctgggcag caggacaggg ttactgccaa ggaggcttca gtgccgagtt      900
caccaagact ggccgtgtgg ttttaggtgg accaggaagc tatttctggc aaggccagat      960
cctgtctgcc actcaggagc agattgcaga atcttattac cccgagtacc tgatcaacct     1020
ggttcagggg cagctgcaga ctcgccaggc cagttccatc tatgatgaca gctacctagg     1080
atactctgtg gctgttggtg aattcagtgg tgatgacaca aaagactttg ttgctggtgt     1140
gcccaaaggg aacctcactt acggctatgt caccatcctt aatggctcag acattcgatc     1200
cctctacaac ttctcagggg aacagatggc ctcctacttt ggctatgcag tggccgccac     1260
agacgtcaat ggggacgggc tggatgactt gctggtgggg gcacccctgc tcatggatcg     1320 gaccccctgac gggcggcctc aggaggtggg cagggtctac gtctacctgc agcacccagc     1380
cggcatagag cccacgccca cccttaccct cactggccat gatgagtttg ccgatttggg     1440
cagctccttg accccctgg gggacctgga ccaggatggc tacaatgatg tggccatcgg     1500
ggctcccttt ggtggggaga cccagcaggg agtagtgttt gtatttcctg ggggcccagg     1560
agggctgggc tctaagcctt cccaggttct gcagcccctg tgggcagcca gccacacccc     1620
agacttcttt ggctctgccc ttcgaggagg ccgagacctg gatggcaatg gatatcctga     1680
tctgattgtg gggtcctttg gtgtggacaa ggctgtggta tacaggggcc gccccatcgt     1740
gtccgctagt gcctccctca ccatcttccc cgccatgttc aacccagagg agcggagctg     1800
cagcttagag gggaaccctg tggcctgcat caaccttagc ttctgcctca atgcttctgg     1860
aaaacacgtt gctgactcca ttggtttcac agtggaactt cagctggact ggcagaagca     1920
gaagggaggg gtacggcggg cactgttcct ggcctccagg caggcaaccc tgacccagac     1980
cctgctcatc cagaatgggg ctcgagagga ttgcagagag atgaagatct acctcaggaa     2040
cgagtcagaa tttcgagaca aactctcgcc gattcacatc gctctcaact tctccttgga     2100 ccccccaagcc ccagtggaca gccacggcct caggccagcc ctacattatc agagcaagag     2160
ccggatagag gacaaggctc agatcttgct ggactgtgga gaagacaaca tctgtgtgcc     2220
tgacctgcag ctggaagtgt ttggggagca gaaccatgtg tacctgggtg acaagaatgc     2280
cctgaacctc actttccatg cccagaatgt gggtgagggt ggcgcctatg aggctgagct     2340
tcgggtcacc gcccctccag aggctgagta ctcaggactc gtcagacacc cagggaactt     2400
ctccagcctg agctgtgact actttgccgt gaaccagagc cgcctgctgg tgtgtgacct     2460
gggcaacccc atgaaggcag gagccagtct gtggggtggc cttcggttta cagtccctca     2520
tctccgggac actaagaaaa ccatccagtt tgacttccag atcctcagca agaatctcaa     2580
caactcgcaa agcgacgtgg tttcctttcg gctctccgtg gaggctcagg cccaggtcac     2640
cctgaacggt gtctccaagc ctgaggcagt gctattccca gtaagcgact ggcatccccg     2700
agaccagcct cagaaggagg aggacctggg acctgctgtc accatgtctc atgagctcat     2760
caaccaaggc cccagctcca ttagccaggg tgtgctggaa ctcagctgtc cccaggctct     2820
ggaaggtcag cagctcctat atgtgaccag agttacggga ctcaactgca ccaccaatca     2880
ccccattaac ccaaagggcc tggagttgga tcccgagggt tccctgcacc accagcaaaa     2940
acgggaagct ccaagccgca gctctgcttc ctcgggacct cagatcctga aatgcccgga     3000
```

```
ggctgagtgt tcaggctgc gctgtgagct cgggcccctg caccaacaag agagccaaag    3060
tctgcagttg catttccgag tctgggccaa gactttcttg cagcgggagc accagccatt    3120
tagcctgcag tgtgaggctg tgtacaaagc cctgaagatg ccctaccgaa tcctgcctcg    3180
gcagctgccc caaaaagagc gtcaggtggc cacagctgtg caatggacca aggcagaagg    3240
cagctatggc gtcccactgt ggatcatcat cctagccatc ctgtttggcc tcctgctcct    3300
aggtctactc atctacatcc tctacaagct tggattcttc aaacgctccc tcccatatgg    3360
caccgccatg gaaaaagctc agctcaagcc tccagccacc tctgatgcct gagtcctccc    3420
aatttcagac tcccattcct gaagaaccag tccccccacc ctcattctac tgaaaaggag    3480
gggtctgggt acttcttgaa ggtgctgacg ccagggaga agctcctctc cccagcccag    3540
agacatactt gaagggccag agccaggggg gtgaggagct ggggatccct ccccccccatg   3600 cactgtgaag gacccttgtt tacacatacc ctcttcatgg atgggggaac tcagatccag    3660
ggacagaggc cccagcctcc ctgaagcctt tgcattttgg agagtttcct gaaacaactt    3720
ggaaagataa ctaggaaatc cattcacagt tctttgggcc agacatgcca aaggacttc    3780 ctgtccagct ccaacctgca aagatctgtc ctcagccttg ccagagatcc aaaagaagcc    3840
cccagctaag aacctggaac ttggggagtt aagacctggc agctctggac agccccaccc    3900
tggtgggcca caaagaaca ctaactatgc atggtgcccc aggaccagct caggacagat    3960
gccacacaag gatagatgct ggcccagggc ccagagccca gctccaaggg gaatcagaac    4020
tcaaatgggg ccagatccag cctggggtct ggagttgatc tggaacccag actcagacat    4080
tggcacctaa tccaggcaga tccaggacta tatttgggcc tgctccagac ctgatcctgg    4140
aggcccagtt caccctgatt taggagaagc caggaattc ccaggaccct gaaggggcca    4200
tgatggcaac agatctggaa cctcagcctg ccagacaca ggccctccct gttccccaga    4260
gaaaggggag cccactgtcc tgggcctgca gaattgggt tctgcctgcc agctgcactg    4320
atgctgcccc tcatctctct gcccaaccct tccctcacct tggcaccaga cacccaggac    4380
ttatttaaac tctgttgcaa gtgcaataaa tctgacccag tgcccccact gaccagaact    4440
agaaaaaaaa aaaaaaaaa a                                              4461
```

<210> SEQ ID NO 14
<211> LENGTH: 2073
<212> TYPE: DNA
<213> ORGANISM: homo sapiens

<400> SEQUENCE: 14

```
agatgccacg ccccatagct ccaccagtca ccgcggcaca gtggccctta agcgaggagc      60
ggcggcgccc gcagcaatca cagcagtgcc gacgtcgtgg gtgtttggtg tgaggctgcg     120
agccgccgcg agttctcacg gtcccgccgg cgccaccacc gcggtcactc accgccgccg     180
ccgccaccac tgccaccacg gtcgcctgcc acagtgtgtct gcaattgaac tccaaggtgc    240
agaatggttt ggaaagtagc tgtattcctc agtgtggccc tgggcattgg tgccgttcct    300
atagatgatc ctgaagatgg aggcaagcac tgggtggtga tcgtggcagg ttcaaatggc    360
tggtataatt ataggcacca ggcagacgcg tgccatgcct accagatcat tcaccgcaat    420
gggattcctg acgaacagat cgttgtgatg atgtacgatg acattgctta ctctgaagac    480
aatcccactc aggaattgt gatcaacagg cccaatggca cagatgtcta tcagggagtc    540
ccgaaggact acactggaga ggatgttacc ccacaaaatt tccttgctgt gttgagaggc    600
```

```
gatgcagaag cagtgaaggg cataggatcc ggcaaagtcc tgaagagtgg cccccaggat      660
cacgtgttca tttacttcac tgaccatgga tctactggaa tactggtttt tcccaatgaa      720
gatcttcatg taaaggacct gaatgagacc atccattaca tgtacaaaca caaaatgtac      780
cgaaagatgg tgttctacat tgaagcctgt gagtctgggt ccatgatgaa ccacctgccg      840
gataacatca atgtttatgc aactactgct gccaacccca gagagtcgtc ctacgcctgt      900
tactatgatg agaagaggtc cacgtacctg ggggactggt acagcgtcaa ctggatggaa      960
gattcggacg tggaagatct gactaaagag accctgcaca agcagtacca cctggtaaaa     1020
tcgcacacca acaccagcca cgtcatgcag tatggaaaca aaacaatctc accatgaaa      1080 gtgatgcagt ttcagggtat gaaacgcaaa gccagttctc ccgtccccct acctccagtc     1140
acacaccttg acctcacccc cagccctgat gtgcctctca ccatcatgaa aaggaaactg     1200
atgaacacca atgatctgga ggagtccagg cagctcacgg aggagatcca gcggcatctg     1260
gatgccaggc acctcattga agtcagtg cgtaagatcg tctccttgct ggcagcgtcc       1320
gaggctgagg tggagcagct cctgtccgag agagcccgc tcacggggca gctgctac        1380 ccagaggccc tgctgcactt ccggaccac tgcttcaact ggcactcccc cacgtacgag      1440
tatgcgttga cacatttgta cgtgctgtc aaccttgtg agaagccgta tccgcttcac       1500
aggataaaat tgtccatgga ccacgtgtgc cttggtcact actgaagagc tgcctcctgg     1560
aagcttttcc aagtgtgagc gccccaccga ctgtgtgctg atcagagact ggagaggtgg     1620
agtgagaagt ctccgctgct cgggccctcc tggggagccc ccgctccagg gctcgctcca    1680
ggaccttctt cacaagatga cttgctcgct gttacctgct tccccagtct tttctgaaaa     1740
actacaaatt agggtgggaa aagctctgta ttgagaaggg tcatatttgc tttctaggag     1800
gtttgttgtt ttgcctgtta gttttgagga gcaggaagct catggggggct tctgtagccc    1860 ctctcaaaag gagtctttat tctgagaatt tgaagctgaa acctcttta atcttcagaa      1920 tgattttatt gaagagggcc gcaagcccca aatggaaaac tgttttttaga aaatatgatg    1980 attttttgatt gcttttgtat ttaattctgc aggtgttcaa gtcttaaaaa ataaagattt     2040
ataacagaac ccaaataaaa aaaaaaaaa aaa                                    2073
```

<210> SEQ ID NO 15
<211> LENGTH: 3610
<212> TYPE: DNA
<213> ORGANISM: homo sapiens

<400> SEQUENCE: 15

```
gagaggctgt gggagaaggg agggaccaga ggagagagcg agagagggaa ccagacccca       60
gttcgccgac taagcagaag aaagatcaaa aaccggaaaa gaggagaaga gcaaacaggc      120
actttgagga acaatcccct ttaactccaa gccgacagcg gtctaggaat tcaagttcag      180
tgcctaccga agacaaaggc gccccgaggg agtggcggtg cgaccccagg gcgtgggccc      240
ggccgcggag cccacactgc ccggctgacc cggtggtctc ggaccatgtc tcccgcccca      300 agacccccc gttgtctcct gctccccctg ctcacgctcg gcaccgcgct cgcctccctc      360
ggctcggccc aaagcagcag cttcagcccc gaagcctggc tacagcaata tggctacctg     420
cctcccgggg acctacgtac ccacacacag cgctcacccc agtcactctc agcggccatc     480
gctgccatgc agaagtttta cggcttgcaa gtaacaggca agctgatgc agacaccatg     540 aaggccatga ggcgccccg atgtggtgtt ccagacaagt tggggctga gatcaaggcc      600 aatgttcgaa ggaagcgcta cgccatccag ggtctcaaat ggcaacataa tgaaatcact    660
```

```
ttctgcatcc agaattacac ccccaaggtg ggcgagtatg ccacatacga ggccattcgc      720
aaggcgttcc gcgtgtggga gagtgccaca ccactgcgct tccgcgaggt gccctatgcc      780
tacatccgtg agggccatga gaagcaggcc gacatcatga tcttctttgc cgagggcttc      840
catggcgaca gcacgccctt cgatggtgag ggcggcttcc tggcccatgc ctacttccca      900
ggccccaaca ttggaggaga cacccacttt gactctgccg agccttggac tgtcaggaat      960
gaggatctga tggaaatgga catcttcctg gtggctgtgc acgagctggg ccatgccctg     1020
gggctcgagc attccagtga cccctcggcc atcatggcac ccttttacca gtggatggac     1080
acggagaatt ttgtgctgcc cgatgatgac cgccggggca tccagcaact ttatgggggt     1140
gagtcagggt tccccaccaa gatgcccccc aacccagga ctacctcccg gccttctgtt      1200
cctgataaac ccaaaaaccc cacctatggg cccaacatct gtgacgggaa ctttgacacc     1260
gtggccatgc tccgagggga gatgtttgtc ttcaaggagc gctggttctg gcgggtgagg     1320
aataaccaag tgatggatgg atacccaatg cccattggcc agttctggcg gggcctgcct     1380
gcgtccatca acactgccta cgagaggaag gatggcaaat tcgtcttctt caaaggagac     1440
aagcattggg tgtttgatga ggcgtccctg gaacctggct accccaagca cattaaggag     1500
ctgggccgag ggctgcctac cgacaagatt gatgctgctc tcttctggat gcccaatgga     1560
aagacctact tcttccgtgg aaacaagtac taccgtttca cgaagagct cagggcagtg      1620
gatagcgagt accccaagaa catcaaagtc tgggaaggga tccctgagtc tcccagaggg     1680
tcattcatgg gcagcgatga agtcttcact tacttctaca aggggaacaa atactggaaa     1740
ttcaacaacc agaagctgaa ggtagaaccg ggctacccca gtcagccct gagggactgg      1800
atgggctgcc catcgggagg ccggccggat gaggggactg aggaggagac ggaggtgatc     1860
atcattgagg tggacgagga gggcggcggg gcggtgagcg cggctgccgt ggtgctgccc     1920
gtgctgctgc tgctcctggt gctggcggtg ggccttgcag tcttcttctt cagacgccat     1980
gggaccccca ggcgactgct ctactgccag cgttccctgc tggacaaggt ctgacgccca     2040
ccgccggccc gcccactcct accacaagga ctttgcctct gaaggccagt ggcagcaggt     2100
ggtggtgggt gggctgttcc catcgtcccg agccccctcc ccgcagcctc cttgcttctc     2160
tctgtcccct ggctggcctc cttcaccctg accgcctccc tcctcctgc cccggcattg      2220
catcttccct agataggtcc cctgagggct gagtgggagg gcggcccttt ccagcctctg     2280
cccctcaggg gaaccctgta gctttgtgtc tgtccagccc catctgaatg tgttggggc      2340
tctgcacttg aaggcaggac cctcagacct cgctggtaaa ggtcaaatgg ggtcatctgc     2400
tccttttcca tccccctgaca taccttaacc tctgaactct gacctcagga ggctctgggc     2460
actccagccc tgaaagcccc aggtgtaccc aattggcagc ctctcactac tctttctggc     2520
taaaaggaat ctaatcttgt tgagggtaga accctgaga cagtgtgagg gggtggggac      2580
tgccaagcca ccctaagacc ttgggaggaa aactcagaga gggtcttcgt tgctcagtca     2640
gtcaagttcc tcggagatct gcctctgcct cacctacccc agggaacttc caaggaagga     2700
gcctgagcca ctgggggacta agtgggcaga agaaaccctt ggcagccctg tgcctctcga     2760
atgttagcct tggatggggc tttcacagtt agaagagctg aaaccagggg tgcagctgtc     2820
aggtagggtg gggccggtgg gagaggcccg ggtcagagcc ctgggggtga gcctgaaggc     2880
cacagagaaa gaaccttgcc caaactcagg cagctgggc tgaggcccaa aggcagaaca      2940
gccagagggg gcaggagggg accaaaaagg aaaatgagga cgtgcagcag cattggaagg     3000
```

| | |
|---|---:|
| ctggggccgg gcaggccagg ccaagccaag caggggccca cagggtgggc tgtggagctc | 3060 |
| tcaggaaggg ccctgaggaa ggcacacttg ctcctgttgg tccctgtcct tgctgcccag | 3120 |
| gcagcgtgga ggggaagggt agggcagcca gagaaaggag cagagaaggc acacaaacga | 3180 |
| ggaatgaggg gcttcacgag aggccacagg gcctggctgg ccacgctgtc ccggcctgct | 3240 |
| caccatctca gtgaggggca ggagctgggg ctcgcttagg ctgggtccac gcttccctgg | 3300 |
| tgccagcacc cctcaagcct gtctcaccag tggcctgccc tctcgctccc ccacccagcc | 3360 |
| cacccattga agtctccttg ggccaccaaa ggtggtggcc atggtaccgg ggacttggga | 3420 |
| gagtgagacc cagtggaggg agcaagagga gagggatgtc ggggggggtgg ggcacggggt | 3480 |
| aggggaaatg gggtgaacgg tgctggcagt tcggctagat ttctgtcttg tttgttttttt | 3540 |
| tgttttgttt aatgtatatt tttattataa ttattatata tgaattccat tcaaaaaaaa | 3600 |
| aaaaaaaaaa | 3610 |

<210> SEQ ID NO 16
<211> LENGTH: 941
<212> TYPE: DNA
<213> ORGANISM: homo sapiens

<400> SEQUENCE: 16

| | |
|---|---:|
| ccaagagcta aaagagagca aggaggaaac aacagcagct ccaaccaggg cagccttcct | 60 |
| gagaagatgc aaccaatcct gcttctgctg gccttcctcc tgctgcccag gcagatgca | 120 |
| ggggagatca tcgggggaca tgaggccaag ccccactccc gcccctacat ggcttatctt | 180 |
| atgatctggg atcagaagtc tctgaagagg tgcggtggct tcctgatacg agacgacttc | 240 |
| gtgctgacag ctgctcactg ttggggaagc tccataaatg tcaccttggg ggcccacaat | 300 |
| atcaaagaac aggagccgac ccagcagttt atccctgtga aaagacccat cccccatcca | 360 |
| gcctataatc ctaagaactt ctccaacgac atcatgctac tgcagctgga gagaaaggcc | 420 |
| aagcggacca gagctgtgca gcccctcagg ctacctagca caaggcccca ggtgaagcca | 480 |
| gggcagacat gcagtgtggc cggctggggg cagacggccc ccctgggaaa acactcacac | 540 |
| acactacaag aggtgaagat gacagtgcag gaagatcgaa agtgcgaatc tgacttacgc | 600 |
| cattattacg acagtaccat tgagttgtgc gtgggggacc cagagattaa aaagacttcc | 660 |
| tttaaggggg actctggagg ccctcttgtg tgtaacaagg tggcccaggg cattgtctcc | 720 |
| tatggacgaa acaatggcat gcctccacga gcctgcacca aagtctcaag ctttgtacac | 780 |
| tggataaaga aaaccatgaa acgctactaa ctacaggaag caaactaagc cccgctgta | 840 |
| atgaaacacc ttctctggag ccaagtccag atttacactg ggagaggtgc cagcaactga | 900 |
| ataaataccct cttagctgag tggaaaaaaa aaaaaaaaa a | 941 |

<210> SEQ ID NO 17
<211> LENGTH: 2387
<212> TYPE: DNA
<213> ORGANISM: homo sapiens

<400> SEQUENCE: 17

| | |
|---|---:|
| agacacctct gccctcacca tgagcctctg gcagccctg gtcctggtgc tcctggtgct | 60 |
| gggctgctgc tttgctgccc ccagacagcg ccagtccacc cttgtgctct ccctggaga | 120 |
| cctgagaacc aatctcaccg acaggcagct ggcagaggaa tacctgtacc gctatggtta | 180 |
| cactcgggtg gcagagatgc gtggagagtc gaaatctctg ggcctgcgc tgctgcttct | 240 |
| ccagaagcaa ctgtccctgc ccgagaccgg tgagctggat agcgccacgc tgaaggccat | 300 |

```
gcgaacccca cggtgcgggg tcccagacct gggcagattc caaacctttg agggcgacct      360
caagtggcac caccacaaca tcacctattg gatccaaaac tactcggaag acttgccgcg      420
ggcggtgatt gacgacgcct ttgcccgcgc cttcgcactg tggagcgcgg tgacgccgct      480
caccttcact cgcgtgtaca gccgggacgc agacatcgtc atccagtttg tgtcgcgga      540
gcacggagac gggtatccct tcgacgggaa ggacgggctc ctggcacacg cctttcctcc      600
tggccccggc attcagggag acgcccattt cgacgatgac gagttgtggt ccctgggcaa      660
gggcgtcgtg gttccaactc ggtttggaaa cgcagatggc gcggcctgcc acttcccctt      720
catcttcgag ggccgctcct actctgcctg caccaccgac ggtcgctccg acggcttgcc      780
ctggtgcagt accacggcca actacgacac cgacgaccgg tttggcttct gccccagcga      840
gagactctac acccaggacg gcaatgctga tgggaaaccc tgccagtttc cattcatctt      900
ccaaggccaa tcctactccg cctgcaccac ggacggtcgc tccgacggct accgctggtg      960
cgccaccacc gccaactacg accgggacaa gctcttcggc ttctgcccga cccgagctga     1020
ctcgacggtg atgggggca actcggcggg ggagctgtgc gtcttcccct tcactttcct     1080
gggtaaggag tactcgacct gtaccagcga ggggccgcgga gatgggcgcc tctggtgcgc     1140
taccacctcg aactttgaca gcgacaagaa gtggggcttc tgcccggacc aaggatacag     1200
tttgttcctc gtggcggcgc atgagttcgg ccacgcgctg gcttagatc attcctcagt     1260
gccggaggcg ctcatgtacc ctatgtaccg cttcactgag gggcccccct tgcataagga     1320
cgacgtgaat ggcatccggc acctctatgg tcctcgccct gaacctgagc cacggcctcc     1380
aaccaccacc acaccgcagc ccacggctcc cccgacggtc tgccccaccg acccccccac     1440
tgtccacccc tcagagcgcc ccacagctgg ccccacaggt cccccctcag ctggccccac     1500
aggtcccccc actgctggcc cttctacggc cactactgtg cctttgagtc cggtggacga     1560
tgcctgcaac gtgaacatct tcgacgccat cgcggagatt gggaaccagc tgtatttgtt     1620
caaggatggg aagtactggc gattctctga gggcaggggg agccggccgc agggcccctt     1680
ccttatcgcc gacaagtggc ccgcgctgcc ccgcaagctg gactcggtct ttgaggagcg     1740
gctctccaag aagcttttct tcttctctgg gcgccaggtg tgggtgtaca caggcgcgtc     1800
ggtgctgggc ccgaggcgtc tggacaagct gggcctggga ccgacgtgg cccaggtgac     1860
cggggccctc cggagtggca gggggaagat gctgctgttc agcgggcggc gcctctggag     1920
gttcgacgtg aaggcgcaga tggtggatcc ccggagcgcc agcgaggtgg accggatgtt     1980
ccccggggtg cctttggaca cgcacgacgt cttccagtac cgagagaaag cctatttctg     2040
ccaggaccgc ttctactggc gcgtgagttc ccggagtgag ttgaaccagg tggaccaagt     2100
gggctacgtg acctatgaca tcctgcagtg ccctgaggac tagggctccc gtcctgcttt     2160
ggcagtgcca tgtaaatccc cactgggacc aaccctgggg aaggagccag tttgccggat     2220
acaaactggt attctgttct ggaggaaagg gaggagtgga ggtgggctgg gccctctctt     2280
ctcacctttg ttttttgttg gagtgtttct aataaacttg gattctctaa cctttaaaaa     2340
aaaaaaaaaa aaaaaaaaaa aaaaaaaaaa aaaaaaaaaa aaaaaaa                   2387
```

<210> SEQ ID NO 18
<211> LENGTH: 840
<212> TYPE: DNA
<213> ORGANISM: homo sapiens

<400> SEQUENCE: 18

```
actcgccacc tcctcttcca cccctgccag gcccagcagc caccacagcg cctgcttcct    60
cggccctgaa atcatgcccc taggtctcct gtggctgggc ctagccctgt tgggggctct   120
gcatgcccag gcccaggact ccacctcaga cctgatccca gccccacctc tgagcaaggt   180
ccctctgcag cagaacttcc aggacaacca attccagggg aagtggtatg tggtaggcct   240
ggcagggaat gcaattctca gagaagacaa agacccgcaa aagatgtatg ccaccatcta   300
tgagctgaaa aagacaagaa gctacaatgt cacctccgtc ctgtttagga aaagaagtg    360 tgactactgg atcaggactt tgttccaggt tgccagccc ggcgagttca cgctgggcaa    420
cattaagagt taccctggat taacgagtta cctcgtccga gtggtgagca ccaactacaa   480
ccagcatgct atggtgttct tcaagaaagt ttctcaaaac agggagtact tcaagatcac   540
cctctacggg agaaccaagg agctgacttc ggaactaaag gagaacttca tccgcttctc   600
caaatctctg ggcctccctg aaaaccacat cgtcttccct gtcccaatcg accagtgtat   660
cgacggctga gtgcacaggt gccgccagct gccgcaccag cccgaacacc attgagggag   720
ctgggagacc ctccccacag tgccacccat gcagctgctc cccaggccac cccgctgatg   780
gagccccacc ttgtctgcta aataaacatg tgccctcagg ccaaaaaaaa aaaaaaaaa    840
```

<210> SEQ ID NO 19
<211> LENGTH: 3147
<212> TYPE: DNA
<213> ORGANISM: homo sapiens
<400> SEQUENCE: 19

```
gacacatgat gctgtgaacg tcagggtgct cgccagggaa gggccctacc cagagggaca    60
gaaagaaagc caggaggggt agagtttgaa gagaagatca tgttctccct gaagacgctt   120
ccatttctgc tcttactcca tgtgcagatt tccaggcct ttcctgtatc ttctaaagag    180
aaaaatacaa aaactgttca gcagaataaa taagccttt ctacagtagt gaagaggata    240
aaaaagagga actgcactga tgcaacaaat acctcaagag aagtcaatta atgactacct   300
ggaaaagttc taccaattac caagcaacca gtatcagtct acaaggaaga atggcactaa   360
tgtgatcgtt gaaaagctta agaaatgca gcgattttt gggttgaatg tgacggggaa     420
gccaaatgag gaaactctgg acatgatgaa aaagcctcgc tgtggagtgc ctgacagtgg   480
tggttttatg ttaaccccag gaaacccaa gtgggaacgc actaacttga cctacaggat    540
tcgaaactat accccacagc tgtcagaggc tgaggtagaa agagctatca aggatgcctt   600
tgaactctgg agtgttgcat cacctctcat cttcaccagg atctcacagg agagggcaga   660
tatcaacatt gcttttttacc aaagagatca cggtgacaat tctccatttg atggacccaa   720
tggaatcctt gctcatgcct ttcagccagg ccaaggtatt ggaggagatg ctcattttga   780
tgccgaagaa acatggacca acacctccgc aaattacaac ttgttcttg ttgctgctca    840 tgaatttggc cattctttgg ggctcgctca ctcctctgac cctggtgcct tgatgtatcc   900
caactatgct ttcagggaaa ccagcaacta ctcactccct caagatgaca tcgatggcat   960
tcaggccatc tatggacttt caagcaaccc tatccaacct actggaccaa gcacacccaa  1020
accctgtgac cccagtttga catttgatgc tatcaccaca ctccgtggag aaatactttt  1080
ctttaaagac aggtacttct ggagaaggca tcctcagcta caaagagtcg aaatgaattt  1140 tattttctcta ttctggccat cccttccaac tggtatacag gctgcttatg aagattttga  1200
cagagacctc atttttcctat ttaaaggcaa ccaatactgg gctctgagtg gctatgatat  1260
tctgcaaggt tatcccaagg atatatcaaa ctatggcttc cccagcagcg tccaagcaat  1320
```

| | |
|---|---|
| tgacgcagct gttttctaca gaagtaaaac atacttcttt gtaaatgacc aattctggag | 1380 |
| atatgataac caaagacaat tcatggagcc aggttatccc aaaagcatat caggtgcctt | 1440 |
| tccaggaata gagagtaaag ttgatgcagt tttccagcaa gaacatttct tccatgtctt | 1500 |
| cagtggacca agatattacg catttgatct tattgctcag agagttacca gagttgcaag | 1560 |
| aggcaataaa tggcttaact gtagatatgg ctgaagcaaa atcaaatgtg gctgtatcca | 1620 |
| cttctcagaat gttgaaggga agttcagcaa gcattttcgt tacattgtgt cctgcttata | 1680 |
| cttttctcaa tattaagtca ttgtttccca tcactgtatc cattctacct gtcctccgtg | 1740 |
| aaaatatgtt tggaatattc cactatttgc agaggcttat tcagttctta cacattccat | 1800 |
| cttacattag tgattccatc aaagagaagg aaagtaagcc tttttgtcac ctcaatattt | 1860 |
| actatttcaa tacttacata tctgacttct aggatttatt gttatattac ttgcctatct | 1920 |
| gacttcatac atccctcagt ttcttaaaat gtcctatgta tatcttctac atgcaattta | 1980 |
| gaactagatt ttggttagaa gtaaggatta taaacaacct agacagtacc cttggccttt | 2040 |
| acagaaaata tggtgctgtt ttctacccctt ggaaagaaat gtagatgata tgtttcgtgg | 2100 |
| gttgaattgt gtcccccata aaagatatgt tgaagttcta accccaggta cccatgaatg | 2160 |
| tgagcttacc agggtctttg cagatgtaat tagttaagtt aaggtgagat cacactgaat | 2220 |
| tagggtgggc tctaaatcca ttatgactgt tgttcttata agaagaagag aggcatagtc | 2280 |
| acctagggga ggaggccgta tgaagacaga ggcagagatt ggagtgacgc atctccaagc | 2340 |
| caaggaattc caaggactgt aagccaccag tagaagcttt gaagaggcaa ggaaggattc | 2400 |
| cctccaatag ccttcaagtg tgaccctgct gacacctgca gaattcggac ttctatcctc | 2460 |
| caaaccgtg agggaataaa tttcctttgt tttaagccac caactttgca atactttgtt | 2520 |
| acagcaaccc tagacatgag gtactagaca cagtacatct acacatatga aaatgaatca | 2580 |
| acacagaatg cagaagtaga acccttgcta aggactactg ggcatcttcc caggacagca | 2640 |
| gccaaaagag aaccaccact tcctctcctg cctcctcctt gctctctcct agagtccaaa | 2700 |
| cccaaatggg ccagttggat ctgatgttcg tcagttcttt acttctattt cctggggtac | 2760 |
| tcaggagggc acacactata gataacttgg gttagctgca taaaattcaa tgtctcatta | 2820 |
| agttgcatta aactgagctt agatgtgtaa gtttgctaac ggatgggttt ttttgttaag | 2880 |
| aactatagga tttatgggac caagtctagc gagtccagat atcaaaatca ttataatgtt | 2940 |
| atatttgctg ttattagaat ataatatagc ttattataca ataaatatgt agactgtaaa | 3000 |
| atatatttct cactagtacc tcctattttc tttctctgtt gaagtttta aatcccacag | 3060 |
| ataattaaat tggcacccttt atgcttgttc aaaaattaaa ataatctatt aaataagttc | 3120 |
| aaattaaaga ttttacttc aaatgac | 3147 |

<210> SEQ ID NO 20
<211> LENGTH: 3276
<212> TYPE: DNA
<213> ORGANISM: homo sapiens

<400> SEQUENCE: 20

| | |
|---|---|
| cgagcatttt ttttttttttt tggaagtcct aggactgatc tccaggacca gcactcttct | 60 |
| cccagccctt agggtcctgc tcggccaagg ccttccctgc catgcgacct gtcagtgtct | 120 |
| ggcagtggag cccctggggg ctgctgctgt gcctgctgtg cagttcgtgc ttggggtctc | 180 |
| cgtccccttc cacgggccct gagaagaagg ccgggagcca ggggcttcgg ttccggctgg | 240 |

```
ctggcttccc caggaagccc tacgagggcc gcgtggagat acagcgagct ggtgaatggg      300
gcaccatctg cgatgatgac ttcacgctgc aggctgccca catcctctgc cgggagctgg      360
gcttcacaga ggccacaggc tggacccaca gtgccaaata tggccctgga acaggccgca      420
tctggctgga caacttgagc tgcagtggga ccgagcagag tgtgactgaa tgtgcctccc      480
ggggctgggg gaacagtgac tgtacgcacg atgaggatgc tggggtcatc tgcaaagacc      540
agcgcctccc tggcttctcg gactccaatg tcattgaggc ccgtgtccgt ctaaagggcg      600
gcgcccaccc tggagagggc cgggtagaag tcctgaaggc cagcacatgg ggcacagtct      660
gtgaccgcaa gtgggacctg catgcagcca gcgtggtgtg tcgggagctg ggcttcggga      720
gtgctcgaga agctctgagt ggcgctcgca tgggcaggg catgggtgct atccacctga      780
gtgaagttcg ctgctctgga caggagctct ccctctggaa gtgccccac aagaacatca      840
cagctgagga ttgttcacat agccaggatg ccggggtccg gtgcaaccta ccttacactg      900
gggcagagac caggatccga ctcagtgggg ccgcagcca acatgagggg cgagtcgagg      960
tgcaaatagg gggacctggg cccttcgct ggggcctcat ctgtggggat gactggggga     1020
ccctggaggc catggtggcc tgtaggcaac tgggtctggg ctacgccaac cacggcctgc     1080
aggagacctg gtactgggac tctgggaata taacagaggt ggtgatgagt ggagtgcgct     1140
gcacagggac tgagctgtcc ctggatcagt gtgcccatca tggcacccac atcacctgca     1200
agaggacagg gacccgcttc actgctggag tcatctgttc tgagactgca tcagatctgt     1260
tgctgcactc agcactggtg caggagaccg cctacatcga agaccggccc ctgcatatgt     1320
tgtactgtgc tgcggaagag aactgcctgg ccagctcagc ccgctcagcc aactggccct     1380
atggtcaccg gcgtctgctc cgattctcct cccagatcca aacctggga cgagctgact     1440
tcaggcccaa ggctgggcgc cactcctggg tgtggcacga gtgccatggg cattaccaca     1500
gcatggacat cttcactcac tatgatatcc tcaccccaaa tggcaccaag gtggctgagg     1560
gccacaaagc tagtttctgt ctcgaagaca ctgagtgtca ggaggatgtc tccaagcggt     1620
atgagtgtgc caactttgga gagcaaggca tcactgtggg ttgctgggat ctctaccggc     1680
atgacattga ctgtcagtgg attgacatca cggatgtgaa gccaggaaac tacattctcc     1740
aggttgtcat caacccaaac tttgaagtag cagagagtga ctttaccaac aatgcaatga     1800
aatgtaactg caaatatgat ggacatagaa tctgggtgca caactgccac attggtgatg     1860
ccttcagtga agaggccaac aggaggttttg aacgctaccc tggccagacc agcaaccaga     1920
ttatctaagt gccactgccc tctgcaaacc accactggcc cctaatggca ggggtctgag     1980
gctgccatta cctcaggagc ttaccaagaa acccatgtca gcaaccgcac tcatcagacc     2040
atgcactatg gatgtggaac tgtcaagcag aagttttcac cctccttcag aggccagctg     2100
tcagtatctg tagccaagca tgggaatctt tgctcccagg cccagcaccg agcagaacag     2160
accagagccc accacaccac aaagagcagc acctgactaa ctgcccacaa agatggcag      2220
cagctcattt tctttaatag gaggtcagga tggtcagctc cagtatctcc cctaagttta     2280
gggggataca gctttaccct agccttttg gtgggggaaa agatccagcc ctcccacctc     2340
attttttact ataatatgtt gctaggtata atttttatttt atataaaaag tgtttctgtg    2400
attcttcaga gcccaggagt cagtgctggt ggttggaggg acctgccccc actggttcat     2460
ttaaccctct gtctcggtgc cctcagaacc tcagccagaa aggcaaggag gaaatcagag     2520
caggagcctt atactcttgg tgatctattc attctgtgac ctcaggggtc acatataagg     2580
tcagtgtttc tcgtccccgc cggatctgca ctgccaactg ggattgggtt cgaacagctt     2640
```

| | |
|---|---:|
| cataaacatc ttcagcattt tgtaccatct gctccccaat ggccaaaatc acatcaccag | 2700 |
| gccgcagacc agcccTATAG agaaaaatgg acagagagaa aggaaggagt acaaagccta | 2760 |
| gttcaaggac acatgcacac cttgcccatc cccatatcac actgcagcct ctccctcacc | 2820 |
| ggtgtgcagg ggagcccagg atgactttat ggatgagtac accatgctga acatcgggaa | 2880 |
| agcttggttc tcgaagctgt agttcagcaa ggatgctgaa agtacacaga tcaccctatt | 2940 |
| agccaaaccc aggcattctc cccatcctga gttccacctc aagtctctca tcaacacatt | 3000 |
| gataaatata tggacaggac atgggctagg tactacaaaa tacaatggca actcactttc | 3060 |
| tgtcttctag caataaagtg caacatgtac ataaaagatg tacaccacat gagggcacca | 3120 |
| aatgacaaac agtgttaaat caatagcact aatgtcattc tagaatacta agagaagctt | 3180 |
| taaggggaaa gaacttaagt tgagcctaaa aggatggatc tgatattaac catataaaac | 3240 |
| aagaacagca taaataaaaa acatgggagt aggaaa | 3276 |

<210> SEQ ID NO 21
<211> LENGTH: 639
<212> TYPE: DNA
<213> ORGANISM: homo sapiens

<400> SEQUENCE: 21

| | |
|---|---:|
| gagagaagga gagcctgcag acagaggcct ccagcttggt ctgtctcccc acctctacca | 60 |
| gcatctgctg agctatgagc caaaccaggg atttacaggg aggaaaagct ttcggactgc | 120 |
| tgaaggccca gcaggaagag aggctggatg agatcaacaa gcaattccta gacgatccca | 180 |
| aatatagcag tgatgaggat ctgccctcca aactggaagg cttcaaagag aaatacatgg | 240 |
| agtttgacct taatggaaat ggcgatattg atatcatgtc cctgaaacga atgctggaga | 300 |
| aacttggagt ccccaagact cacctagagc taaagaaatt aattggagag gtgtccagtg | 360 |
| gctccgggga gacgttcagc tacccTGACT ttctcaggat gatgctgggc aagagatctg | 420 |
| ccatcctaaa aatgatcctg atgtatgagg aaaaagcgag agaaaggaa aagccaacag | 480 |
| gccccccagc caagaaagct atctctgagt tgccctgatt tgaagggaaa agggatgatg | 540 |
| ggattgaagg ggcttctaat gacccagata tggaaacaga agacaaaatt gtaagccaga | 600 |
| gtcaacaaat taaataaatt accccctcct ccagatcaa | 639 |

<210> SEQ ID NO 22
<211> LENGTH: 3810
<212> TYPE: DNA
<213> ORGANISM: homo sapiens

<400> SEQUENCE: 22

| | |
|---|---:|
| gcggcggccg ccttcgggga aggggtggg tccggggagg ggtttgccat cctcctctag | 60 |
| ttaaaagtaa gggggaaaag agtaaacgcg cgactccagc gcgcggctac ctacgcttgg | 120 |
| tgcttgcttt ctccagccat cggagaccag agccgcccc tctgctcgag aaagggctc | 180 |
| agcggcggcg gaagcggagg gggaccaccg tggagagcgc ggtcccagcc cggccactgc | 240 |
| ggatccctga aaccaaaaag ctcctgctgc ttctgtaccc cgcctgtccc tcccagctgc | 300 |
| gcagggcccc ttcgtgggat catcagcccg aagacaggga tggagaggcc tctgtgctcc | 360 |
| cacctctgca gctgcctggc tatgctggcc ctcctgtccc cctgagcct ggcacagtat | 420 |
| gacagctggc cccattaccc cgagtacttc cagcaaccgg ctcctgagta tcaccagccc | 480 |
| caggccccccg ccaacgtggc caagattcag ctgcgcctgg ctgggcagaa gaggaagcac | 540 |

| | |
|---|---|
| agcgagggcc gggtggaggt gtactatgat ggccagtggg gcaccgtgtg cgatgacgac | 600 |
| ttctccatcc acgctgccca cgtcgtctgc cgggagctgg gctacgtgga ggccaagtcc | 660 |
| tggactgcca gctcctccta cggcaaggga aagggccca tctggttaga caatctccac | 720 |
| tgtactggca acgaggcgac ccttgcagca tgcacctcca atggctgggg cgtcactgac | 780 |
| tgcaagcaca cggaggatgt cggtgtggtg tgcagcgaca aaaggattcc tgggttcaaa | 840 |
| tttgacaatt cgttgatcaa ccagatagag aacctgaata tccaggtgga ggacattcgg | 900 |
| attcgagcca tcctctcaac ctaccgcaag cgcacccag tgatggaggg ctacgtggag | 960 |
| gtgaaggagg caagacctg gaagcagatc tgtgacaagc actggacggc caagaattcc | 1020 |
| cgcgtggtct gcggcatgtt tggcttccct ggggagagga catacaatac caaagtgtac | 1080 |
| aaaatgtttg cctcacggag gaagcagcgc tactggccat tctccatgga ctgcaccggc | 1140 |
| acagaggccc acatctccag ctgcaagctg ggccccagg tgtcactgga ccccatgaag | 1200 |
| aatgtcacct gcgagaatgg gctaccggcc gtggtgagtt gtgtgcctgg gcaggtcttc | 1260 |
| agccctgacg gaccctcaag attccggaaa gcgtacaagc cagagcaacc cctggtgcga | 1320 |
| ctgagaggcg gtgcctacat cggggagggc cgcgtggagg tgctcaaaaa tggagaatgg | 1380 |
| gggaccgtct gcgacgacaa gtgggacctg gtgtcggcca gtgtggtctg cagagagctg | 1440 |
| ggctttggga gtgccaaaga ggcagtcact ggctcccgac tggggcaagg gatcggaccc | 1500 |
| atccacctca acgagatcca gtgcacaggc aatgagaagt ccattataga ctgcaagttc | 1560 |
| aatgccgagt ctcagggctg caaccacgag gaggatgctg gtgtgagatg caacacccct | 1620 |
| gccatgggct gcagaagaa gctgcgcctg aacggcggcc gcaatcccta cgagggccga | 1680 |
| gtggaggtgc tggtggagag aaacgggtcc cttgtgtggg ggatggtgtg tggccaaaac | 1740 |
| tggggcatcg tggaggccat ggtggtctgc cgccagctgg gctgggatt cgccagcaac | 1800 |
| gccttccagg agacctggta ttggcacgga gatgtcaaca gcaacaaagt ggtcatgagt | 1860 |
| ggagtgaagt gctcgggaac ggagctgtcc ctggcgcact gccgccacga cggggaggac | 1920 |
| gtggcctgcc cccagggcgg agtgcagtac ggggccggag ttgcctgctc agaaaccgcc | 1980 |
| cctgacctgg tcctcaatgc ggagatggtg cagcagacca cctacctgga ggaccggccc | 2040 |
| atgttcatgc tgcagtgtgc catggaggag aactgcctct cggcctcagc cgcgcagacc | 2100 |
| gaccccacca cgggctaccg ccggctcctg cgcttctcct cccagatcca caacaatggc | 2160 |
| cagtccgact tccggcccaa gaacggccgc cacgcgtgga tctggcacga ctgtcacagg | 2220 |
| cactaccaca gcatggaggt gttcacccac tatgacctgc tgaacctcaa tggcaccaag | 2280 |
| gtggcagagg ccacaaggc cagcttctgc ttggaggaca cagaatgtga aggagacatc | 2340 |
| cagaagaatt acgagtgtgc caacttcggc gatcagggca tcaccatggg ctgctgggac | 2400 |
| atgtaccgcc atgacatcga ctgccagtgg gttgacatca ctgacgtgcc ccctggagac | 2460 |
| tacctgttcc aggttgttat taaccccaac ttcgaggttg cagaatccga ttactccaac | 2520 |
| aacatcatga aatgcaggag ccgctatgac ggccaccgca tctggatgta caactgccac | 2580 |
| ataggtggtt ccttcagcga agagacggaa aaaagtttg agcacttcag cgggctctta | 2640 |
| aacaaccagc tgtccccgca gtaaagaagc ctgcgtggtc aactcctgtc ttcaggccac | 2700 |
| accacatctt ccatgggact tccccccaac aactgagtct gaacgaatgc acgtgccct | 2760 |
| cacccagccc ggccccacc ctgtccagac ccctacagct gtgtctaagc tcaggaggaa | 2820 |
| agggaccctc ccatcattca tggggggctg ctacctgacc cttggggcct gagaaggcct | 2880 |
| tgcgggggtg gggtttgtcc acagagctgc tggagcagca ccaagagcca gtcttgaccg | 2940 |

```
ggatgaggcc cacagacagg ttgtcatcag cttgtcccat tcaagccacc gagctcacca    3000
cagacacagt ggagccgcgc tcttctccag tgacacgtgg acaaatgcgg gctcatcagc    3060
ccccccagag agggtcaggc cgaacccat ttctcctcct cttaggtcat tttcagcaaa     3120
cttgaatatc tagacctctc ttccaatgaa accctccagt ctattatagt cacatagata    3180
atggtgccac gtgttttctg atttggtgag ctcagacttg gtgcttccct atccacagcc    3240
cccacccctt gttttcaag atactattat tatattttca cagactttg aagcacaaat     3300 ttattggcat ttaatattgg acatctgggc ccttggaagt acaaatctaa ggaaaaacca    3360
acccactgtg taagtgactc atcttcctgt tgttccaatt ctgtgggttt ttgattcaac    3420
ggtgctataa ccagggtcct gggtgacagg gcgctcactg agcaccatgt gtcatcacag    3480
acacttacac atacttgaaa cttggaataa aagaaagatt tatgaaacgt gtctgtgttt    3540
cctttgaccc acagcacctg ggccctgagc agcaggcttc ctatgttcag tggccagaag    3600
cagagcttca ggtacattcg tggttttctc cggtggacat gggtcctcag atcccctcca    3660
gcccagtgtg ccaccaggg cacctccttc aatagactcc aaaaggggca gctcctacca    3720
tctgggagaa gcaatctaag gagatcacaa aaagtaacgg aacaggagtc ataatctttc    3780
ttgaactcct gtggttttta ctgaaacttg                                     3810

<210> SEQ ID NO 23
<211> LENGTH: 5496
<212> TYPE: DNA
<213> ORGANISM: homo sapiens

<400> SEQUENCE: 23
ctgtggcttg ccccagagct gatccttgtc tttgtccact tctcagcgag gatggcactt      60
cagggagccc ttcccttact atcgcagaga gagcaggccc tccccagtca tgtccaaccc     120
agaactctgt tttgttttct tcatagcccct agcatcacag aaaatcaccc tgtgcattca    180
tggatgtcca cggggggcaag ggctttgtgt tgcttaaccc agcatcctga accgtgtttg    240
ttgaatgaat acagaacccc gtttgctctg ggagagcaca gaaaacagtc ttctatcata    300
tatcatagcc agctgcaaac agcagatggc ttcccatatc ccagagagta agaaccagag    360
agagagagaa agagagagag tttgggtctt tctcctctgt gcctgctctc tccagagaaa    420 ctggagggt agcagttagc attccccgc tggttccacc aagcacagtc aaggtctcta      480
ggacatggcc acccctcacc tgtggaagcg gtcctgctgg ggtgggtggg tgttagttgg    540
ttctggtttg ggtcagagac acccagtggc ccaggtgggc gtgggccag ggcgcagacg      600 agaaggggca cgagggctcc gctccgagga cccagcggca agcaccggtc ccgggcgcgc    660
cccagcccac ccactcgcgt gcccacgcg gcattattcc ctataaggat ctgaacgatc      720 cggggggcggc ccgccccgt tacccctttgc ccccggcccc gccccctttt tggagggccg    780
atgaggtaat gcggctctgc cattggtctg aggggggcggg cccaacagc cgaggcggg      840 gtccccgggg gcccagcgct atatcactcg gccgcccagg cagcggcgca gagcgggcag    900
caggcaggcg gcgggcgctc agacggcttc tcctcctcct cttgctcctc cagctcctgc    960
tccttcgccg ggaggccgcc cgccgagtcc tgcgccagcg ccgaggcagc ctcgctgcgc    1020
cccatcccgt cccgccgggc actcggaggg cagcgcgccg gaggccaagg ttgccccgca    1080
cggcccggcg ggcgagcgag ctcgggctgc agcagcccg ccggcggcgc gcacggcaac     1140
tttggagagg cgagcagcag cccggcagc ggcggcagca gcggcaatga cccttggct      1200
```

-continued

```
cgggctcatc gtgctcctgg gcagctggag cctgggggac tggggcgccg aggcgtgcac    1260
atgctcgccc agccaccccc aggacgcctt ctgcaactcc gacatcgtga tccgggccaa    1320
ggtggtgggg aagaagctgg taaaggaggg gcccttcggc acgctggtct acaccatcaa    1380
gcagatgaag atgtaccgag gcttcaccaa gatgccccat gtgcagtaca tccatacgga    1440
agcttccgag agtctctgtg gccttaagct ggaggtcaac aagtaccagt acctgctgac    1500
aggtcgcgtc tatgatggca agatgtacac ggggctgtgc aacttcgtgg agaggtggga    1560
ccagctcacc ctctcccagc gcaaggggct gaactatcgg tatcacctgg gttgtaactg    1620
caagatcaag tcctgctact acctgccttg ctttgtgact tccaagaacg agtgtctctg    1680
gaccgacatg ctctccaatt tcggttaccc tggctaccag tccaaacact acgcctgcat    1740
ccggcagaag ggcggctact gcagctggta ccgaggatgg gccccccgg ataaaagcat    1800 catcaatgcc acagacccct gagcgccaga ccctgcccca cctcacttcc ctcccttccc    1860
gctgagcttc ccttggacac taactcttcc cagatgatga caatgaaatt agtgcctgtt    1920
ttcttgcaaa tttagcactt ggaacattta agaaaggtc tatgctgtca tatggggttt     1980
attgggaact atcctcctgg ccccacccctg ccccttcttt ttggttttga catcattcat   2040
ttccacctgg gaatttctgg tgccatgcca gaaagaatga ggaacctgta ttcctcttct    2100
tcgtgataat ataatctcta tttttttagg aaaacaaaaa tgaaaaacta ctccatttga    2160
ggattgtaat tcccacccct cttgcttctt ccccacctca ccatctccca gaccctcttc    2220
cctttgccct tctcctccaa tacataaagg acacagacaa ggaacttgct gaaaggccaa    2280
ccatttcagg atcagtcaaa ggcagcaagc agatagactc aaggtgtgtg aaagatgtta    2340
tacaccagga gctgccactg catgtcccaa ccagactgtg tctgtctgtg tctgcatgta    2400
agagtgaggg agggaaggaa ggaactacaa gagagtcgga gatgatgcag cacacacaca    2460
attccccagc ccagtgatgc ttgtgttgac cagatgttcc tgagtctgga gcaagcaccc    2520
aggccagaat aacagagctt tcttagttgg tgaagactta acatctgcc tgaggtcagg     2580 aggcaatttg cctgccttgt acaaaagctc aggtgaaaga ctgagatgaa tgtctttcct    2640
ctccctgcct cccaccagac ttcctcctgg aaaacgcttt ggtagatttg gccaggagct    2700
ttcttttatg taaattggat aaatacacac accatacact atccacagat atagccaagt    2760
agatttgggt agaggatact atttccagaa tagtgtttag ctcacctagg gggatatgtt    2820
tgtatacaca tttgcatata cccacatggg gacataagct aatttttta caggacacag     2880 aattctgttc aatgctgtta aatatgccaa tagtttaatc tcttctattt tgttgtcgtt    2940
gcttgtttga agaaaatcat gacattccaa gttgacattt tttttcatt ttaattaaaa     3000 tttgaaattc tgaacaccgt cagcaccctc tcttccctat catgggtcat ctgacccctg    3060
tccgtctcct tgtccctgct tcatgtttgg gggccttct ttaactgcct tcctggctta     3120
gctcagatgg cagatgagag tgtagtcaag ggcctgggca caggagggag agctgcagag    3180
tgtcctgcct gccttggctg gagggacacc tctcctgggt gtggagacag cttggttccc    3240
tttccctagc tccctggtgg gtgaatgcca cctcctgaga tcctcacctc ttggaattaa    3300
aattgttggt cactggggaa agcctgagtt tgcaaccagt tgtagggttt ctgttgtgtt    3360
tttttttttt tttttgaaat aaaactataa tataaattct cctattaaat aaaattattt    3420
taagttttag tgtcaaaagt gagatgctga gagtaggtga taatgtatat tttacagagt    3480
gggggttggc aggatggtga cattgaacat gattgctctc tgtctctttt ttcagcttat    3540
gggtatttat cttctattag tatttgtatc ttcagttcat tccactttag gaaacagagc    3600
```

```
tgccaattga acagaagaa gaaaaaaaaa aaaagcagca gacaacacac tgtagagtct    3660
tgcacacaca caagtgccca ggcaaggtgc ttggcagaac cgcagagtgg gaagagagta    3720
ccggcatcgg gtttccttgg gatcaatttc attaccgtgt acctttccca ttgtggtcat    3780
gccatttggc agggggagaa tgggaggctt ggccttcttt gtgaggcagt gtgagcagaa    3840
gctgatgcca gcatgtcact ggttttgaag ggatgagccc agacttgatg ttttgggatt    3900
gtccttattt taacctcaag gtctcgcatg tggggcccc tgaccaacct acacaagttc     3960
cctcccacaa gtggacatca gtgtcttctc tgtgaggcat ctggccattc gcactccctg    4020
gtgtggtcag cctctctcac acaaggagga acttgggtga aggctgagtg tgaggcacct    4080
gaagtttccc tgcggagtcg ataaattagc agaaccacat ccccatctgt taggccttgg    4140
tgaggaggcc ctgggcaaag aagggtcttt cgcaaagcga tgtcagaggg cggttttgag    4200
cttttctataa gctatagctt tgtttatttc acccgttcac ttactgtata atttaaaatc    4260
atttatgtag ctgagacact tctgtatttc aatcatatca tgaacatttt attttgctaa    4320
atcttgtgtc atgtgtaggc tgtaatatgt gtacattgtg tttaagagaa aaatgaaacc    4380
cacatgccgc cattttcctg aatcaaattc tgcagtggaa tggagaggaa atacttccta    4440
ggcaagcagc tagactggtg aattgggga aatagaagga actagtaact gagactcctc     4500
cagcctcctc cctattggaa tcccaatggc tcctggagta ggaaaaaagt ttaaactaca    4560
ttcatgttct tgttctgtgt cactcggccc tgggtagtct accatttact tcaccccaag    4620
tcctgctgcc catccagttg ggaagccatg attttcctaa gaatccaggg ccatgggaga    4680
tacaattcca agttctcgct cctcctttg ggcatctctt ctgcctccca atcaaggaag     4740
ctccatgctc aggctctcag ctctcgggcc agtgctctgc tctgtccagg gtaggtaata    4800
ctgggagact cctgtctttt accctcccct cgttccagac ctgcctcatg gtggcaacat    4860
ggttcttgaa caattaaaga aacaaatgac tttttggaat agccctgtct agggcaaact    4920
gtggccccca ggagacacta cccttccatg ccccagacct ctgtcttgca tgtgacaatt    4980
gacaatctgg actaccccaa gatggcaccc aagtgtttgg cttctggcta cctaaggtta    5040
acatgtcact agagtatttt tatgagagac aaacattata aaaatctgat ggcaaaagca    5100
aaacaaaatg gaaagtaggg gaggtggatg tgacaacaac ttccaaattg gctctttga    5160
ggcgagagga aggggagaac ttggagaata gttttttgctt tgggggtaga ggcttcttag    5220
attctcccag catccgcctt tcccttttagc cagtctgctg tcctgaaacc cagaagtgat    5280
ggagagaaac caacaagaga tctcgaaccc tgtctagaag gaatgtattt gttgctaaat    5340
ttcgtagcac tgtttacagt tttcctccat gttatttatg aattttatat tccgtgaatg    5400
tatattgtct tgtaatgttg cataatgttc acttttata gtgtgtccctt tattctaaac    5460
agtaaagtgg ttttatttct atcacaaaaa aaaaaa                              5496

<210> SEQ ID NO 24
<211> LENGTH: 2371
<212> TYPE: DNA
<213> ORGANISM: homo sapiens

<400> SEQUENCE: 24
attcattcag agtgggaaag cgccagccga gcggccagcc agtgcggggc tggccatgta     60
aggcccacag gcggtcctgc ccgcccggtg ccctgcggag agcctcgtgc agccctgggc    120
accgcccctg ccctgccctg accccttggc cttgaaatgc tgtcatcgga ggagccgtcc    180
```

```
cgctcgggac aaggccagca tggacaaagc tagagctggg gcaagcaagg agccttcctg      240
tcctcgaggc cgtgggaaga gaagcacgcc caggggggcca ctcctgagag cctctctgtc     300
caccaggcct ctgcagaggg gtcaccatgg ctctggcccg aggcagccgg cagctggggg      360
ccctggtgtg gggcgcctgc ctgtgcgtgc tggtgcacgg gcagcaggcg cagcccgggc      420
agggctcgga ccccgcccgc tggcggcagc tgatccagtg ggagaacaac gggcaggtgt      480
acagcttgct caactcgggc tcagagtacg tgccggccgg acctcagcgc tccgagagta      540
gctcccgggt gctgctggcc ggcgcgcccc aggcccagca gcggcgcagc cacgggagcc      600
cccggcgtcg gcaggcgccg tccctgcccc tgcggggcg cgtgggctcg acaccgtgc       660 gcggccaggc gcggcaccca ttcggctttg ccaggtgcc cgacaactgg cgcgaggtgg      720
ccgtcgggga cagcacgggc atggcccggg cccgcacctc cgtctcccag caacggcacg      780
ggggctccgc ctcctcggtc tcggcttcgg ccttcgccag cacctaccgc cagcagccct      840 cctaccccgca gcagttcccc tacccgcagg cgcccttcgt cagccagtac gagaactacg     900
accccgcgtc gcggacctac gaccagggtt tcgtgtacta ccggcccgcg ggcggcggcg      960
tgggcgcggg ggcggcggcc gtggcctcgg cggggggtcat ctacccctac cagccccggg    1020
cgcgctacga ggagtacggc ggcggcgaag agctgcccga gtaccgcct cagggcttct      1080 acccggcccc cgagaggccc tacgtgccgc cgccgccgcc gcccccgac ggcctggacc      1140 gccgctactc gcacagtctg tacagcgagg gcacccccgg cttcgagcag gcctaccctg     1200
accccggtcc cgaggcggcg caggcccatg gcggagaccc acgctgggc tggtacccgc      1260 cctacgccaa cccgccgccc gaggcgtacg gccgccgcg gcgctggag ccgccctacc       1320 tgccggtgcg cagctccgac acgccccgc cgggtgggga gcggaacggc gcgcagcagg      1380
gccgcctcag cgtgggcagc gtgtaccggc ccaaccagaa cggccgcggt ctccctgact     1440
tggtcccaga ccccaactat gtgcaagcat ccacttatgt gcagagagcc cacctgtact     1500
ccctgcgctg tgctgcggag gagaagtgtc tggccagcac agcctatgcc cctgaggcca    1560
ccgactacga tgtgcgggtg ctactgcgct tccccccagcg cgtgaagaac cagggcacag     1620
cagacttcct ccccaaccgg ccacggcaca cctgggagtg gcagcagctgc caccagcatt    1680 accacagcat ggacgagttc agccactacg acctactgga tgcagccaca ggcaagaagg     1740
tggccgaggg ccacaaggcc agtttctgcc tggaggacag cacctgtgac ttcggcaacc     1800
tcaagcgcta tgcatgcacc tctcataccc agggcctgag cccaggctgc tatgacacct     1860
acaatgcgga catcgactgc cagtggatcg acataaccga cgtgcagcct gggaactaca     1920
tcctcaaggt gcacgtgaac ccaaagtata ttgttttgga gtctgacttc accaacaacg     1980
tggtgagatg caacattcac tacacaggtc gctacgtttc tgcaacaaac tgcaaaattg    2040
tccaatcctg atctccggga gggacagatg gccaatctct cccttccaa agcaggccct    2100 gctcccgggg cagcctcccg ccgagggggcc cagccccccaa cccacaggca cggaggggca    2160
tccctccctg ccggcctcag ggagcgaacg tggatgaaaa ccacagggat ccggacgcc     2220 agacccccatt ttatacttca cttttctcta cagtgttgtt ttgttgttgt tggttttat    2280 ttttatact ttggccatac cacagagcta gattgcccag gtctgggctg aataaacaa      2340 ggttttctta ctctgaaaaa aaaaaaaaa a                                     2371
```

<210> SEQ ID NO 25
<211> LENGTH: 3316
<212> TYPE: DNA
<213> ORGANISM: homo sapiens

<400> SEQUENCE: 25

```
gcggaaaaga gcctcgggcc aggagcgcag gaaccagacc gtgtcccgcg gggctgtcac    60
ctccgcctct gctccccgac ccggccatgc gcggcctcgg gctctggctg ctgggcgcga   120
tgatgctgcc tgcgattgcc cccagccggc cctgggccct catggagcag tatgaggtcg   180
tgttgccgtg gcgtctgcca ggccccgag tccgccgagc tctgccctcc cacttgggcc    240
tgcacccaga gagggtgagc tacgtccttg gggccacagg gcacaacttc accctccacc   300
tgcggaagaa cagggacctg ctgggctccg gctacacaga gacctatacg gctgccaatg   360
gctccgaggt gacggagcag cctcgcgggc aggaccactg cttctaccag gccacgtag    420
aggggtaccc ggactcagcc gccagcctca gcacctgtgc cggcctcagg ggtttcttcc   480
aggtggggtc agacctgcac ctgatcgagc ccctggatga aggtggcgag gcggacggc    540
acgccgtgta ccaggctgag cacctgctgc agacggccgg gacctgcggg gtcagcgacg   600
acagcctggg cagcctcctg gaccccgga cggcagccgt cttcaggcct cggcccgggg    660
actctctgcc atcccgagag acccgctacg tggagctgta tgtggtcgtg gacaatgcag   720
agttccagat gctggggagc gaagcagccg tgcgtcatcg ggtgctggag gtggtgaatc   780
acgtggacaa gctatatcag aaactcaact tccgtgtggt cctggtgggc ctggagattt   840
ggaatagtca ggacaggttc cacgtcagcc ccgaccccag tgtcacactg gagaacctcc   900
tgacctggca ggcacggcaa cggacacggc ggcacctgca tgacaacgta cagctcatca   960
cggggtgtcga cttcaccggg actaccgtgg ggtttgccag ggtgtccgcc atgtgctccc  1020
acagctcagg ggctgtgaac caggaccaca gcaagaaccc cgtgggcgtg gcctgtacca  1080
tggcccatga gatgggccac aacctgggca tggaccatga tgagaacgtc cagggctgcc  1140
gctgccagga acgcttcgag gccggccgct gcatcatggc gggcagcatt ggctccagtt  1200
tccccaggat gttcagtgac tgcagccagg cctacctgga gagcttttg gagcggccgc   1260
agtcggtgtg cctcgccaac gcccctgacc tcagccacct ggtgggcggc cccgtgtgtg  1320
ggaacctgtt tgtggagcgt ggggagcagt gcgactgcgg cccccccgag gactgccgga  1380
accgctgctg caactctacc acctgccagc tggctgaggg ggcccagtgt gcgcacggta  1440
cctgctgcca ggagtgcaag gtgaagccgg ctggtgagct gtgccgtccc aagaaggaca  1500
tgtgtgacct cgaggagttc tgtgacgcc ggcaccctga gtgcccggaa gacgccttcc   1560
aggagaacgg cacgccctgc tccgggggct actgctacaa cggggcctgt cccacactgg  1620
cccagcagtg ccaggccttc tgggggccag gtgggcaggc tgccgaggag tcctgcttct  1680
cctatgacat cctaccaggc tgcaaggcca gccggtacag ggctgacatg tgtggcgttc  1740
tgcagtgcaa gggtgggcag cagccctggg ggcgtgccat ctgcatcgtg gatgtgtgcc  1800
acgcgctcac cacagaggat ggcactgcgt atgaaccagt gcccgagggc acccggtgtg  1860
gaccagagaa ggtttgctgg aaaggacgtt gccaggactt acacgtttac agatccagca  1920
actgctctgc ccagtgccac aaccatgggg tgtgcaacca caagcaggag tgccactgcc  1980
acgcgggctg ggcccccgcc cactgcgcga agctgctgac tgaggtgcac gcagcgtccg  2040
ggagcctccc cgtcttcgtg gtggtggttc tggtgctcct ggcagttgtg ctggtcaccc  2100
tggcaggcat catcgtctac cgcaaagccc ggagccgcat cctgagcagg aacgtggctc  2160
ccaagaccac aatggggcgc tccaaccccc tgttccacca ggctgccagc cgcgtgccgg  2220
ccaagggcgg ggctccagcc ccatccaggg ccccccaaga gctggtcccc accacccacc  2280
```

```
cgggccagcc cgcccgacac ccggcctcct cggtggctct gaagaggccg cccctgctc      2340
ctccggtcac tgtgtccagc ccacccttcc cagttcctgt ctacacccgg caggcaccaa      2400
agcaggtcat caagccaacg ttcgcacccc cagtgccccc agtcaaaccc ggggctggtg      2460
cggccaaccc tggtccagct gagggtgctg ttggcccaaa ggttgccctg aagcccccca      2520
tccagaggaa gcaaggagcc ggagctccca cagcaccca gggggcacc tgcgcctgtg       2580
tggaaatttg gagaagttgc ggcagagaag ccatgcgttc cagcattcca cggtccagct      2640
agtgccgctc agccctagac cctgactttg caggctcagc tgctgttcta acctcaggaa      2700
tgcatctacc tgagaggctc ctgctgtcca cgccctcagc caattccttc tccccgcctt      2760
ggccacgtgt agccccagct gtctgcaggc accaggctgg gatgagctgt gtgcttgcgg      2820
gtgcgtgtgt gtgtacgtgt ctccaggtgg ccgctggtct cccgctgtgt tcaggaggcc      2880
acatatacag ccctcccag ccacacctgc ccctgctctg gggcctgctg agccggctgc       2940
cctgggcacc cggttccagg cagcacagac gtggggcatc cccagaaaga ctccatccca      3000
ggaccaggtt cccctgcgtg ctcttcgaga gggtgtcagt gagcagactg caccccaagc      3060
tcccgactcc aggtcccctg atcttggggc ctgtttccca tgggattcaa gagggacagc      3120
cccagctttg tgtgtgttta agcttaggaa tcgcctttat ggaaagggct atgtgggaga      3180
gtcagctatc ttgtctggtt ttcttgagac ctcagatgtg tgttcagcag gctgaaagc       3240
ttttattctt taataatgag aaatgtatat tttactaata aattattgac cgagttctgt      3300
aaaaaaaaaa aaaaaa                                                      3316

<210> SEQ ID NO 26
<211> LENGTH: 1984
<212> TYPE: DNA
<213> ORGANISM: homo sapiens

<400> SEQUENCE: 26
ctgatttaca ggaactcaca ccagcgatca atcttcctta atttgtaact gggcagtgtc        60
ccgggccagc caatagctaa gactgccccc cccgcacccc accctccctg accctggggg       120
actctctact cagtctgcac tggagctgcc tggtgaccag aagtttggag tccgctgacg       180
tcgccgccca gatggcctcc aggctgaccc tgctgaccct cctgctgctg ctgctggctg       240
gggatagagc ctcctcaaat ccaaatgcta ccagctccag ctcccaggat ccagagagtt       300
tgcaagacag aggcgaaggg aaggtcgcaa caacagttat ctccaagatg ctattcgttg       360
aacccatcct ggaggtttcc agcttgccga caaccaactc aacaaccaat tcagccacca       420
aaataacagc taataccact gatgaaccca ccacacaacc caccacagag cccaccaccc       480
aacccaccat ccaacccacc caaccaacta cccagctccc aacagattct cctacccagc       540
ccactactgg gtccttctgc ccaggacctg ttactctctg ctctgacttg gagagtcatt       600
caacagaggc cgtgttgggg gatgcttttg tagatttctc cctgaagctc taccacgcct       660
tctcagcaat gaagaaggtg gagaccaaca tggcctttcc ccattcagc atcgccagcc        720
tccttaccca ggtcctgctc ggggctgggg agaacaccaa acaaacctg gagagcatcc        780
tctcttaccc caaggacttc acctgtgtcc accaggccct gaagggcttc acgaccaaag       840
gtgtcacctc agtctctcag atcttccaca gcccagacct ggccataagg gacaccttg        900
tgaatgcctc tcggaccctg tacagcagca gccccagagt cctaagcaac acagtgacg        960
ccaacttgga gctcatcaac acctgggtgg ccaagaacac caacaacaag atcagccggc       1020
tgctagacag tctgccctcc gatacccgcc ttgtcctcct caatgctatc tacctgagtg      1080
```

```
ccaagtggaa gacaacattt gatcccaaga aaaccagaat ggaacccttt cacttcaaaa    1140
actcagttat aaaagtgccc atgatgaata gcaagaagta ccctgtggcc catttcattg    1200
accaaacttt gaaagccaag gtggggcagc tgcagctctc ccacaatctg agtttggtga    1260
tcctggtacc ccagaacctg aaacatcgtc ttgaagacat ggaacaggct ctcagccctt    1320
ctgttttcaa ggccatcatg gagaaactgg agatgtccaa gttccagccc actctcctaa    1380 cactacccecg catcaaagtg acgaccagcc aggatatgct ctcaatcatg gagaaattgg    1440
aattcttcga tttttcttat gaccttaacc tgtgtgggct gacagaggac ccagatcttc    1500
aggtttctgc gatgcagcac cagacagtgc tggaactgac agagactggg gtggaggcgg    1560
ctgcagcctc cgccatctct gtggcccgca ccctgctggt ctttgaagtg cagcagccct    1620
tcctcttcgt gctctgggac cagcagcaca agttccctgt cttcatgggg cgagtatatg    1680
accccagggc ctgagacctg caggatcagg ttagggcgag cgctacctct ccagcctcag    1740
ctctcagttg cagccctgct gctgcctgcc tggacttggc ccctgccacc tcctgcctca    1800
ggtgtccgct atccaccaaa agggctccct gagggtctgg gcaagggacc tgcttctatt    1860
agcccttctc catggccctg ccatgctctc caaaccactt tttgcagctt tctctagttc    1920
aagttcacca gactctataa ataaaacctg acagaccatg actttcaaaa aaaaaaaaaa    1980
aaaa                                                                  1984

<210> SEQ ID NO 27
<211> LENGTH: 2592
<212> TYPE: DNA
<213> ORGANISM: homo sapiens

<400> SEQUENCE: 27
catccgtgcg tctgtggaag gctgcgtttc cggcctgaga aaccgtcatg tttctgggga      60
gtcacctcag ctggcagtta ccaccgtgtt agaaagcagc tcaggaccgg gccacctcca     120
tcactggcgt caccatgggg gctgtgctgg gtgtcttctc cctcgccagc tgggttccat     180
gcctctgcag cggtgcctca tgtttgctgt gtagttgctg tcctaacagt aagaattcca     240
cggtgactcg cctcatttat gctttcattc tcctcctgag cactgtcgta tcctatatca     300
tgcagagaaa agagatggaa acttacttga agaagattcc tggattttgt gaaggggggat     360 ttaaaatcca tgaggctgat ataaatgcag ataaagattt gatgtgctg gttggttata     420 aagctgtgta tcggatcagc tttgccatgg ccatcttttt cttttgtcttt tctctgctca     480 tgttcaaagt aaaaacaagt aaagatctcc gagcggcagt acacaatggg ttttggttct     540
tcaaaattgc tgcccttatt ggaatcatgg ttggctcttt ctacatccct gggggctatt     600
tcagctcagt ctggtttgtt gttggcatga taggggccgc cctcttcatc ctcattcagc     660
tggtgctgct ggtagatttt gctcattctt ggaatgaatc atgggtaaat cgaatggaag     720
aaggaaaccc aaggttgtgg tatgctgctt tactgtcttt cacaagcgcc ttttatatcc     780
tgtcaatcat ctgtgtcggg ctgctctata catattacac caaaccagat ggctgcacag     840
aaaacaagtt cttcatcagt attaacctga tcctttgcgt tgtggcttct attatatcga     900
tccacccaaa aattcaggaa caccagcctc gctccggcct cttgcagtcc tccctcatca     960
ccctctacac tatgtaccct acctggtcag ccatgtccaa tgaacctgat cgttcctgca    1020
atcccaacct gatgagcttt attacacgca taactgcacc aaacctggct cctggaaatt    1080
caactgctgt ggtccctacc cctactccac catcaaagag tgggtcttta ctggattcag    1140
```

```
ataatttat  tggactgttt  gtctttgttc  tctgcctctt  gtattctagc  atccgcactt  1200
ccactaatag  ccaagtagac  aagctgaccc  tgtcagggag  tgacagcgtc  atccttggtg  1260
atacaactac  cagtggtgcc  agtgatgaag  aagatggaca  gcctcggcgg  gctgtggaca  1320
acgagaaaga  gggagtgcag  tatagctact  ccttattcca  cctcatgctc  tgcttggctt  1380
ccttgtacat  catgatgacc  ctgaccagct  ggtacagccc  tgatgcaaag  tttcagagca  1440
tgaccagcaa  gtggccagct  gtgtgggtca  agatcagctc  cagctgggtc  tgcctcctgc  1500
tttacgtctg  gacccttgtg  gctccacttg  tcctcaccag  tcgggacttc  agctgaacct  1560
ctgagtgcca  aggacaccac  tggaactcac  aaaggtctcc  ttcaccgaaa  acccatatac  1620
cttttaagtt  tgtttcaact  aaaatattaa  gtgaatgctt  tgcaagtttg  actgtatgca  1680
ggtttatatc  agaaggtgag  attgaataat  gcttgatgca  gaatcgaaac  ttctcattta  1740
tctgtatatt  atgtttactt  ctaaggatat  agcacaaagg  gaacatttt  tgtttaaagt  1800 gaactacagc  tgtgctgtga  agagagttct  ttataaagcc  tgtaggttct  tttaactttg  1860
gtttaaaatg  taagatagga  aaatgttgga  tatttgaggc  catgcttaat  atatttatat  1920
tgcagtatcc  tttaaaagca  aaaaaaaaaa  aatgcattta  tattacagtt  ttcctctatg  1980
aaagtcctta  cttatatgat  acaagcactg  tgttttgtgc  ttaaactctt  cagcggggta  2040
gcatcaaagt  tcttggggaa  ggatcgtata  tgtgggtccc  ttccctagaa  gaatggttgc  2100
tgatatggct  actgcttcta  catcttgagt  ttttaattt  acttttta  cactgtagca  2160 ttgagactgc  ttgattcaag  tctggtgctt  tgccagatgt  attaatttcc  ataaatgctt  2220
tgtgagtttg  gttaaaatga  agattcactt  gggaaaacac  tgcagcttta  gtctgtgtta  2280
ctatcttgtt  atgagtatgt  aaagtaaaa  tgcatgtgaa  tttatcatat  ttgcactatg  2340
aaggtatttg  gttaaaatac  aaagactttt  aagattttaa  ggccctttct  tccaacagct  2400
tttatagtta  gcagccattc  tttattttct  ggatagccag  gttttatcac  gcttctagtc  2460
aggatgctcc  tattccttct  aaaaattacg  gtctgactag  tgagcaaagt  cttgaattta  2520
ttcaaaagtc  ctaaatacct  tctctaggta  agacacttgg  tagatgagag  acggaaggca  2580
ttgtcaagaa  cc                                                         2592
```

<210> SEQ ID NO 28
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 28
agcactgggt gtttgacg                                                    18

<210> SEQ ID NO 29
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 29
gtcttcccat tgggcatc                                                    18

<210> SEQ ID NO 30
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 30
cagacgtggg tcgattcc                                                    18

<210> SEQ ID NO 31
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 31
tcatcgatca tgtctcgc                                                    18

<210> SEQ ID NO 32
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 32
gcagcgcttc ttcagctt                                                    18

<210> SEQ ID NO 33
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 33
gtgtgtgtcc acttggga                                                    18

<210> SEQ ID NO 34
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 34
acgatgatga ccggaagt                                                    18

<210> SEQ ID NO 35
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 35
gtgtagatcg gggccatc                                                    18

<210> SEQ ID NO 36
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 36
gcagtgattt ccccgcca                                                    18

<210> SEQ ID NO 37
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 37
gggggccatc atggtatc                                                 18

<210> SEQ ID NO 38
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 38
aaggaggcag cagagaac                                                 18

<210> SEQ ID NO 39
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 39
gcactgtcat gcaatggg                                                 18

<210> SEQ ID NO 40
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 40
gcctaccaga tcatccac                                                 18

<210> SEQ ID NO 41
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 41
acatctgtgc cgttaggt                                                 18

<210> SEQ ID NO 42
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 42
acaacactct tgacgctg                                                 18

<210> SEQ ID NO 43
<211> LENGTH: 18
<212> TYPE: DNA
<213> ORGANISM: Artificial sequence
<220> FEATURE:
<223> OTHER INFORMATION: Single strand DNA oligonucleotide -continued

<400> SEQUENCE: 43
cgagagtggg gcttgact                                                      18

<210> SEQ ID NO 44
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 44
acaaccagtt cgccatgg                                                      18

<210> SEQ ID NO 45
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 45
aagcggggtg aaacgttcc                                                     19

<210> SEQ ID NO 46
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 46
gaccratcct gtcactgac                                                     19

<210> SEQ ID NO 47
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 47
tgcagtcctc gctcactggg cacg                                               24

<210> SEQ ID NO 48
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 48
ggtgagtaac gcgtaggtaa                                                    20

<210> SEQ ID NO 49
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 49
acgatccgaa aaccttcttc                                                    20

<210> SEQ ID NO 50

```
<210> SEQ ID NO 50
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 50
tctaggagtc ccagtcagcc                                               20

<210> SEQ ID NO 51
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 51
caacaaggac tgccaagcac                                               20

<210> SEQ ID NO 52
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 52
gcccttgagc taggactgga                                               20

<210> SEQ ID NO 53
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 53
tacggccaaa tccgttcaca                                               20

<210> SEQ ID NO 54
<211> LENGTH: 117
<212> TYPE: PRT
<213> ORGANISM: Artificial Sequence
<220> FEATURE:
<223> OTHER INFORMATION: LEM-2/15.8  antibody  VL amino acid sequence

<400> SEQUENCE: 54

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Ile Phe Ser Asn Tyr
            20                  25                  30

Ala Met Ser Trp Val Arg Gln Thr Pro Glu Lys Arg Leu Glu Trp Val
        35                  40                  45

Ala Thr Ile Ser Gly Gly Gly Arg Asn Ile Tyr Ser Leu Asp Ser Val
    50                  55                  60

Lys Gly Arg Phe Thr Phe Phe Arg Asp Asn Ala Arg Asn Thr Leu Tyr
65                  70                  75                  80

Leu Gln Met Ser Ser Leu Arg Ser Glu Asp Thr Ala Met Tyr Phe Cys
                85                  90                  95

Ser Arg Glu Asn Tyr Gly Ser Ser Phe Thr Tyr Trp Gly Gln Gly Thr
            100                 105                 110

Leu Val Thr Val Ser
        115
```

```
<210> SEQ ID NO 55
<211> LENGTH: 116
<212> TYPE: PRT
<213> ORGANISM: Artificial Sequence
<220> FEATURE:
<223> OTHER INFORMATION: LEM-2/15.8  antibody  VH amino acid sequence

<400> SEQUENCE: 55

Leu Val Ile Asp Val Leu Met Thr Gln Thr Pro Leu Ser Leu Pro Val
1               5                   10                  15

Gly Leu Gly Asp Gln Ala Ser Ile Ser Cys Arg Ser Ser Gln Ser Ile
            20                  25                  30

Val His Ser Asn Gly Asn Thr Tyr Leu Glu Trp Tyr Leu Gln Lys Pro
        35                  40                  45

Gly Gln Ser Pro Lys Leu Leu Ile Tyr Lys Val Ser Asn Arg Phe Ser
    50                  55                  60

Gly Val Pro Asp Arg Phe Ser Gly Ser Gly Ser Gly Thr Asp Phe Thr
65                  70                  75                  80

Leu Lys Ile Ser Arg Val Glu Ala Glu Asp Leu Gly Val Tyr Tyr Cys
                85                  90                  95

Phe Gln Gly Ser His Ala Pro Tyr Thr Phe Gly Gly Gly Thr Lys Leu
            100                 105                 110

Glu Ile Lys Arg
            115
```

METHODS OF PREVENTING SECONDARY INFECTIONS

RELATED APPLICATIONS

This application is a National Phase of PCT Patent Application No. PCT/IL2016/050156 having International filing date of Feb. 9, 2016, which claims the benefit of priority under 35 USC § 119(e) of U.S. Provisional Patent Application No. 62/113,551 filed on Feb. 9, 2015. The contents of the above applications are all incorporated by reference as if fully set forth herein in their entirety.

SEQUENCE LISTING STATEMENT

The ASCII file, entitled 70529SequenceListing.txt, created on Aug. 6, 2017, comprising 121,355 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to a method of preventing secondary infections in subjects infected with a pathogen using agents that downregulate extracellular matrix remodeling.

Viral pandemics, such as influenza have caused millions of deaths worldwide. An extreme example is the 1918 pandemic which spread to six continents and infected ~500 million people reaching death toll of 50 million. Investigation of clinical cases and autopsy samples indicated that more than 95% of case fatalities were complicated by secondary bacterial infections, most commonly *Streptococcus pneumoniae* (*S. pneumoniae*). Immune cells recruited to the site of infection are critical for influenza clearance. However, growing evidence shows that infiltrating immune cells can also generate excessive inflammatory responses resulting in collateral tissue damage and disruption of the blood-air-barrier.

Tissue tolerance to pathogens is an important evolutionary trade-off, balancing the host immune response to pathogens while maintaining tissue function. However, tolerance capacity differs between various organs; lungs have a relatively low tissue tolerance capacity, and are more vulnerable to tissue damage. Accordingly, it has been argued that during respiratory viral infections uncontrolled host-derived immune responses, rather than viral titers, may be the leading cause of death. These responses are primarily associated with inflammatory monocytes, granulocytes, macrophages and dendritic cells. Accordingly, influenza-infected lungs are diffusely hemorrhagic, potentially linking the host response with tissue destruction. Tissue breaching may prime secondary bacterial invasion coupled with tissue disruption and, in extreme cases, may result in death. The interaction between influenza and secondary bacterial infections has long been studied, yet the molecular mechanisms by which influenza infection primes the tissue to secondary infections are not fully understood.

One of the host's tolerance components is the integrity of respiratory epithelial barriers anchored to the extracellular matrix (ECM). The ECM scaffold is produced by the cells in the tissue and is composed of two layers: I) the interstitial matrix, a three-dimensional gel of polysaccharides and fibrous proteins, and II) the basement membrane, a mesh-like sheet formed at the base of epithelial tissues. ECM turnover is regulated by multiple proteolytic enzymes including matrix metalloproteinases (MMPs) that are responsible for the irreversible cleavage of a plethora of ECM molecules under normal and pathological conditions. Dysregulated proteolytic activity is often associated with inflammation, cancer, and infectious diseases. Accordingly, studies in pathological conditions have shown that dysregulated proteolysis of ECM molecules and related protein fibers have significant effects on tissue function. Specifically, MMPs were shown to play critical roles in lung organogenesis and many MMPs are involved in the acute and chronic phases of lung inflammatory diseases (Greenlee et al., 2007, Physiological reviews 87, 69-98). Several substrates of MMPs have been identified during lung development, including ECM scaffold proteins, cell adhesion molecules, growth factors, cytokines, and chemokines (Greenlee et al., 2007, Physiological reviews 87, 69-98).

Membrane type-I matrix metalloproteinase (MT1-MMP/MMP-14), a membrane tethered collagenase, is a key regulator in development and homeostasis of the lung as well as mediating wound healing, airway remodeling, and cell trafficking. Accordingly, it is expressed by multiple cell populations in the respiratory tract, including fibroblasts, endothelial cells and macrophages (Greenlee et al., 2007, Physiological reviews 87, 69-98). The functions of macrophage-derived proteases during inflammation are typically associated with tissue invasion or degradative events. In macrophages MT1-MMP serves not only as a protease acting on the ECM, but also regulates macrophage immune response. Recruited monocytes and macrophages up-regulate a broad spectrum of ECM remodelers including various MMPs. Depending on the conditions, macrophages express a spectrum of MMPs and their inhibitors: these have been associated with both physiological and pathological lung remodeling events. MMP-9 (gelatinase B) was shown to be beneficial for recovery from influenza infection by promoting migration of neutrophils to the infection site (Bradley et al., 2012, PLoS pathogens 8, e1002641). Despite these important findings, a systematic analysis of ECM proteolytic pathways during respiratory infections, including the trade-off between ECM integrity and immune protection, has never been completed.

Background art includes Cheung et al., Cardiovasc Pathol. 2006 March-April; 15(2):63-74, Elkington et al., 2005 British Society for Immunology, Clinical and Experimental Immunology, 142:12-20; Devy et al., Biochemistry Research International, Volume 2011, Article ID 191670, doi:10.1155/2011/191670; Renckens et al., J Immunol 2006; 176:3735-3741; Vanlaere et al., Clinical Microbiology Reviews, April 2009, Vol 22, p. 224-239 and Udi et al., 2015, Structure 23, 1-12, Jan. 6, 2015.

SUMMARY OF THE INVENTION

According to an aspect of some embodiments of the present invention there is provided a method of treating or preventing a disease associated with a secondary infection in a subject infected with a pathogen comprising administering to the subject a therapeutically effective amount of an anti-pathogenic agent directed towards the pathogen and a therapeutically effective amount of an agent which downregulates at least one extracellular matrix-associated polypeptide, thereby treating or preventing the disease associated with a secondary infection in the subject.

According to an aspect of some embodiments of the present invention there is provided a method of treating a subject infected with a pathogen comprising administering to the subject a therapeutically effective amount of an anti-pathogenic agent directed towards the pathogen and a therapeutically effective amount of an agent which down-regulates at least one extracellular matrix-associated polypeptide, thereby treating the subject.

According to an aspect of some embodiments of the present invention there is provided an article of manufacture comprising an anti-pathogenic agent and an agent which down-regulates at least one extracellular matrix-associated polypeptide.

According to an aspect of some embodiments of the present invention there is provided a pharmaceutical composition comprising an anti-pathogenic agent as a first active agent, an agent which down-regulates at least one extracellular matrix-associated polypeptide as a second active agent and a pharmaceutically acceptable carrier.

According to an aspect of some embodiments of the present invention there is provided a method of treating influenza in a subject in need thereof comprising administering to the subject a therapeutically effective amount of an agent which down-regulates an extracellular matrix-associated polypeptide, thereby treating the influenza.

According to some embodiments of the invention, the extracellular matrix-associated polypeptide is set forth in Table 1.

According to some embodiments of the invention, the secondary infection is a bacterial infection, a viral infection or a fungal infection.

According to some embodiments of the invention, the secondary infection is a blood infection.

According to some embodiments of the invention, the disease is sepsis.

According to some embodiments of the invention, the administering comprises co-administering.

According to some embodiments of the invention, the pathogen is selected from the group consisting of a virus, a bacteria and a fungus.

According to some embodiments of the invention, the at least one polypeptide is a matrix metalloproteinase (MMP).

According to some embodiments of the invention, the matrix metalloproteinase is selected from the group consisting of membrane type 1-matrix metalloproteinase 1 (MT1-MMP1), MMP-9, MMP-8 and MMP-3.

According to some embodiments of the invention, the at least one polypeptide is membrane type 1-matrix metalloproteinase 1 (MT1-MMP1).

According to some embodiments of the invention, the infection is a respiratory infection.

According to some embodiments of the invention, the pathogen is a virus.

According to some embodiments of the invention, the virus is a respiratory virus.

According to some embodiments of the invention, the respiratory virus is influenza.

According to some embodiments of the invention, the anti-pathogenic agent is a neuraminidase inhibitor (NAI).

According to some embodiments of the invention, the neuraminidase inhibitor is selected from the group consisting of Laninamivir, Oseltamivir, Peramivir and Zanamivir.

According to some embodiments of the invention, the neuraminidase inhibitor is Oseltamivir.

According to some embodiments of the invention, the secondary infection is a bacterial infection.

According to some embodiments of the invention, the bacterial infection is *S. pneumoniae*.

According to some embodiments of the invention, the agent which down-regulates the at least one polypeptide is an antibody.

According to some embodiments of the invention, the agent which down-regulates the at least one polypeptide is a polynucleotide agent.

According to some embodiments of the invention, the extracellular matrix-associated polypeptide is set forth in Table 1.

According to some embodiments of the invention, the at least one polypeptide is a matrix metalloproteinase (MMP).

According to some embodiments of the invention, the matrix metalloproteinase is selected from the group consisting of membrane type 1-matrix metalloproteinase 1 (MT1-MMP1), MMP-9, MMP-8 and MMP-3.

According to some embodiments of the invention, the at least one polypeptide is membrane type 1-matrix metalloproteinase 1 (MT1-MMP1).

According to some embodiments of the invention, the anti-pathogenic agent is an antiviral agent.

According to some embodiments of the invention, the anti-viral agent is a neuraminidase inhibitor (NAI).

According to some embodiments of the invention, the neuraminidase inhibitor is selected from the group consisting of Laninamivir, Oseltamivir, Peramivir and Zanamivir.

According to some embodiments of the invention, the neuraminidase inhibitor is Oseltamivir.

According to some embodiments of the invention, the extracellular matrix-associated polypeptide is set forth in Table 1.

According to some embodiments of the invention, the extracellular matrix associated polypeptide is MT1-MMP1.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-D. Global analysis of extra cellular matrix gene circuits during influenza viral infection (A) K-means clustering (k=20) of 3530 differentially expressed genes (Experimental Procedures) in lungs following influenza infections at 10 time points (n=4 for each time point). Dynamic range is scaled between −2 to 2 fold changes and color coded. 13.5% (479) of the elevated genes are annotated as involved in ECM remodeling. Functional annotation was done using (cbl-gorilladotcsdottechniondotacdotil) clusters are annotated accordingly and colored. (B) Shown are a subset of gene ontologies (GO) enriched (p<10-4) in infected lungs. (C) Submatrix of gene expression dynamics following influenza infection of ECM remodeling genes. (D) Bar graph showing fold changes relative to TO using qPCR measurement of MT1-MMP expression following influenza infection. Each sample was run in triplicates from 4 mice (2 biological repeats). Error bars represent standard deviation (SD) of the average number. The target genes were normalized to the endogenous reference gene GAPDH and relative to a non-infected control sample using ΔΔ CT normalization method.

Figure 2A:
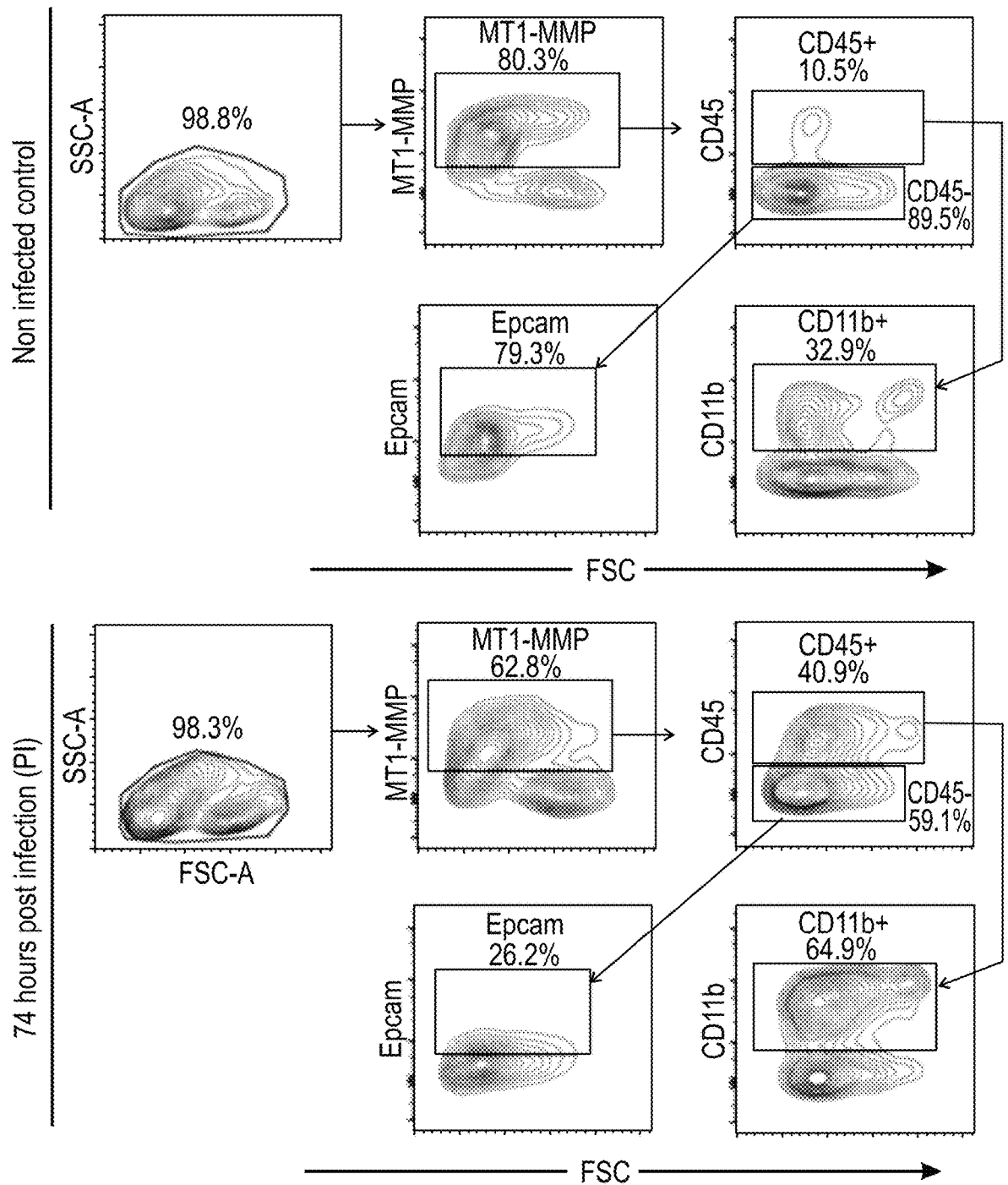
Figure 2B:
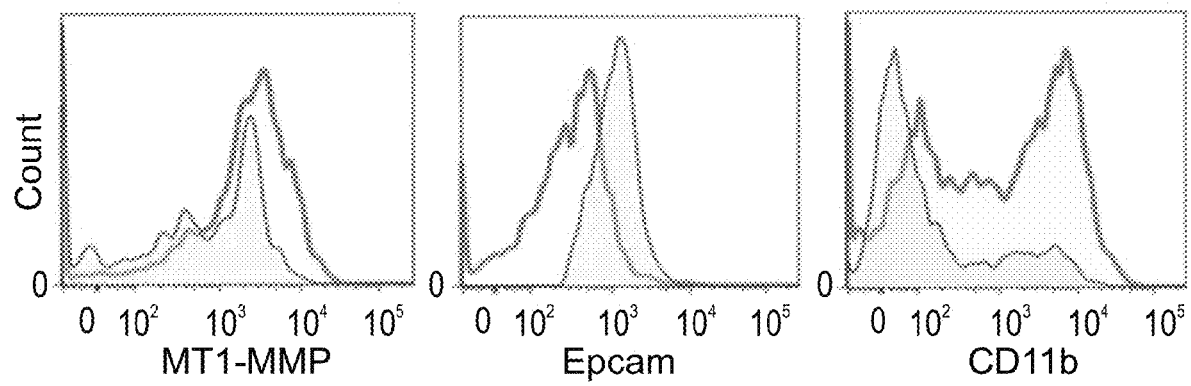
Figure 2C:
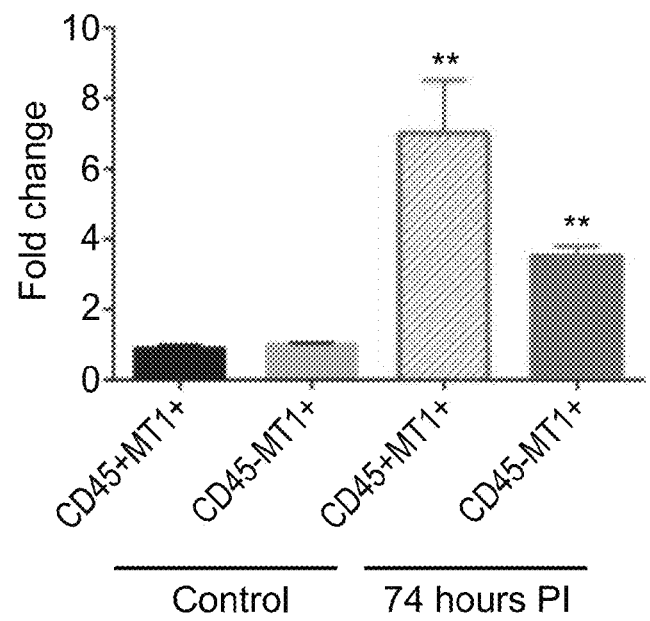

FIGS. 2A-C. MT1-MMP expression is mostly induced in myeloid cells following influenza infection. (A) FACS analysis from lung of influenza infected mice 74 hours post viral infection (Experimental procedures; n=25) compared to non-infected controls (n=25). Gated are MT1-MMP expressing cells stained using anti-MT1-MMP antibody as well as CD45, CD11b and Epcam (Experimental procedures). (B) Histogram plots showing MT1-MMP, Epcam and CD11b mean fluorescence intensity before (grey) and 74 hours post influenza viral infection (red). (C) Bar graph showing qPCR measurement of MT1-MMP expression in sorted cell populations. Error bars represent SD of the average number. T-test **p<0.001.

FIGS. 3A-I. Influenza infection induces changes in ECM morphology (A) Global mass spectrometry analysis of cell free ECM scaffolds (see experimental procedures). Quantitative protein abundance is presented by relative measurement (with reference to control uninfected tissue) using gray scale color code ranging from −1 to 1 white to black. Proteins depleted from the ECM post infection are annotated and colored white. Heatmap showing significant changes in protein quantification (p<0.01, t-test) in de-cellularized infected lung tissue as compared to non-infected control. Samples were analyzed in duplicates for 2 time points post infection (74, 122 hours post infection) with lethal dose of influenza infection using Mascot software (B) Representative scanning electron microscope imaging of infected versus control lungs. Arrows and arrow-heads point to orientation changes in collagen fibrils with D-banding patterns as quantified in sub figure (C) Directionality of fibers on the boundaries of alveoli are analyzed using Fiji package (Experimental procedures). (D-H) Representative immuno-staining images of ECM components during infection taken from (n=20) animals and screened in multiple tissue sections and slides imaged under the same exposure conditions. (E-I) Quantification of immunostaining using imageJ package (Experimental procedures), Error bars represent SD of the average number.

FIGS. 4A-K. Blocking MT1-MMP activity protects lung ECM components. (A) Cartoon showing experimental setup for influenza infection with various treatments. Mice were infected with sub-lethal dose of PR8 influenza strain (Experimental Procedures) (B-E) AirSEM imaging of alveolar and bronchial compartments 74 hours post infection using fixed tissue sections from whole lung, cut 300 μm thick and stained for AirSEM (Experimental Procedures). Alveolar wall thickness and bronchial cell numbers were measured at different areas in multiple sections. Scale of main image—50 μm, inset scale—20 μm. Bar graph quantifies wall thickness and cell numbers in alveoli and bronchi, respectively. Error bars represent SD of the average number; field of view (FOV). (F-G) Representative second harmonic generation (SHG) images originating from an unstained 50 μm thick lung tissue sections. The detected SHG signal representing collagen is shown in red after reproduction of the z-stack using Imaris software package version 7.7.1. Bar graph is showing collagen volumes analyzed and quantified using Imaris package and tested for significance using t-test. Error bars represent SD of the average number (H-I) Lung immuno-staining for laminin. Bar graph shows laminin intensity analyzed using ImageJ package. (J-K) Collagen type I in situ zymography in lung tissue using fluorogenic substrate to detect collagenolytic activity in lung section with high sensitivity. Green signal and arrows point to active collagenase localization among bronchial epithelial lining cells or infiltrating immune cells. Scale—50 μm; Error bars represent SD of the average number; field of view (FOV).

FIGS. 5A-H. Combining anti-viral treatment with ECM protection supports survival and prevents systemic bacterial sepsis. (A, D) Cartoon showing experimental setup for influenza and S. pneumoniae co-infections in preventative and therapeutic modes. Mice were infected with sub-lethal doses of influenza followed by infection with Strep. pneumoniae (Experimental procedures). Treatment groups included: Tamiflu, anti-MT1-MMP Fab, or the combinations of both. Administration was done using preventive mode, one day before infection (A-C) or as therapeutic mode one-day post infection (D-E). Vehicle-treated mice served as controls (Data are combined from three independent experiments with 7-10 mice in each group). (B, E) Survival curves (Kaplan-Meier) of co-infected mice receiving different treatments a day before (−1) or a day after (+1) the infections. Data is collected from 3 independent experiments of 5 mice in each group. *P<0.01; **p<0.001 using Log-rank (Mantel-Cox) test. (C, F) Relative weight loss of co-infected mice at several time points post viral infection. Error bars represent SD from the mean. (G-H) S. pneumonia bacterial loads from spleen lysates of infected mice 6 days post viral infection (Experimental procedures).

FIGS. 6A-D. Gene and protein expression levels of ECM modulators during the course of influenza infection. (A) Bar graph showing qPCR measurements of ECM representative genes during different time points post infection in whole lung tissue (fold change relative to expression levels in TO) infection with lethal dose of influenza infection (experimental procedures). Each sample was run in triplicates from 4 mice (2 biological repeats). Error bars represent standard deviation (SD) (B) Western blot analysis of several representative proteases during different time points of influenza infection using a reducing SDS-PAGE gel. (n=10). (C) Quantification of western blot results using ImageJ software. Average relative density of the protein of interest is relative to GAPDH internal control (D) Mean values of body weight (blue; left y axis) and viral titers (red; right y axis) during the course of influenza infection. Error bars represent standard deviations of body weight, calculated on 2-4 animals in each time point from 3 independent experiments. Viral burdens of whole lung homogenates in the lungs of mice using qPCR for genome copies of Matrix protein 2 (M2) followed by conversion into viral particle numbers using a calibration curve.

FIGS. 7A-D. Immune cells express active MT1-MMP during infection. (A) Immunostaining and bar graph quantification of MT1-MMP and F4/80 marker co-localization in infected lungs (74 hours PI) versus healthy controls. Arrows point to MT1-MMP stained cells. Representative images from multiple sections. (B) Bar graph quantifying panel A. Error bar represent SD, *P≤0.01, t-test. (C) Collagen type I in situ zymography combined with CD45 staining. Arrows point to cells expressing either marker at both control and infected sections (74 hours PI). Scale bar-50 µm (D) Bar graph quantifying panel C. Error bar represent SD, *P≤0.01, t-test.

Figure 8:
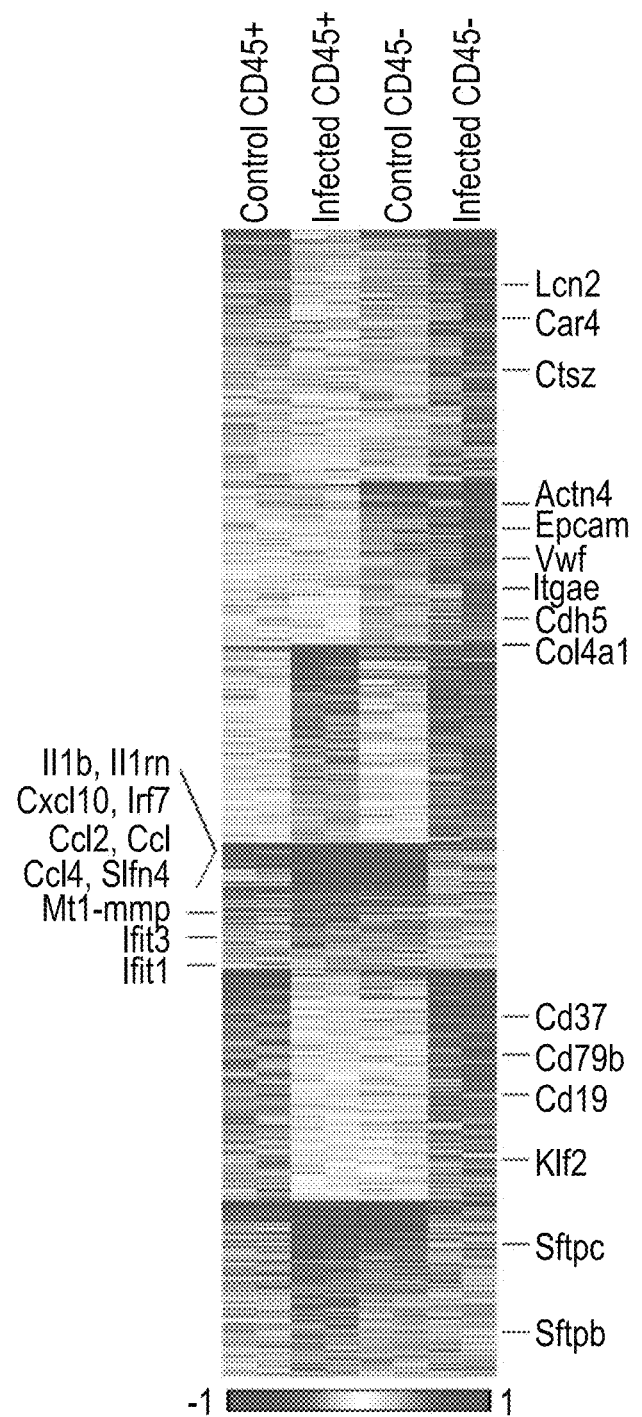

FIG. 8. Global expression analysis of MT1-MMP expressing cells. (A) K-means clustering (k=6) of 2169 differentially expressed genes in $CD45^{pos}$ and $CD45^{neg}$ populations of cells sorted 74 hours post infection (n≥5 mice included in each group-infected and non-infected control). Mice were infected with lethal dose of $4 \times 10^3$ PFU of PR8 influenza (experimental procedures).

FIGS. 9A-D. Lung destructive phenotypes demonstrated using AirSEM imaging of whole lung or de-cellularized tissue. (A) Imaging of whole lung tissue. Arrows point to boundaries of alveolar openings with cells (non-infected control) or depleted of cells (infected) (B) Imaging of ECM scaffolds (after de-cellularization) of infected lungs compared to healthy controls. Arrows point to alveolar duct boundaries containing thick organized collagen bundles (non-infected control) or distorted fibrils (infected). (C) Lung cell counts in control and infected lungs scanning multiple lung sections, n=5. (D) Directionality imaging analysis was done by Fiji package. Graphs were plotted using GraphPad Prism 6. The relative frequency of fiber spatial orientation was measured using the "Directionality" plugin analysis tool in Fiji package version 6.1.1.

FIGS. 10A-C. Calibration of single viral infection. (A) Weight loss of mice subjected to single viral infection at different dosages. Data set was analyzed from 5 mice at each time point. Error bar represent SD and analyzed using t-test. (B) Survival of mice exposed to single viral infection at different dosages. Error bar represent SD and analyzed using t-test **P≤0.001. (C) Viral burdens of whole lung homogenates in the lungs 4 days post infection using standard PFU assay. Samples were run with 2 biological repeats 3 animals at each time point. X-axis represents the viral amounts used for the infection.

FIGS. 11A-F. MT1-MMP inhibition does not interfere with immune cell recruitment or cytokine induction. (A) FACS analysis of whole lung tissue subjected to influenza infection 74 hours post infection and treated either with anti-MT1-MMP inhibitor antibody or non-relevant GST control Ab. Mice were infected at sub-lethal influenza dose (experimental procedures). Data is gated on MT1-MMP expressing cells stained with MT1-MMP antibody as well as CD45, Ly6G, Ly6C, CD11b, NK46, TCRβ (Experimental procedures). Experiments were done twice using 3 mice per group. (B) Representative sections of lung tissue stained for macrophages using F4/80 marker taken at 74 hours post infection. Scale bars=50 µm. FOV indicates the entire field of view at magnification of ×20. (C) Quantification of figure B using multiple tissue sections from at least 3 mice per group. Error bar represent SD, ***P≤0.0001, t-test. (D) Infiltrating immune cells in BALF from mice subjected to single viral infection and taken at 24, 48, 72, 122 hours PI. Mice were infected with sub-lethal dose of influenza. Samples were run with 2 biological repeats. Tested significant over non-infected mice using t-test *P≤0.01. (E-F) TNF-α and IL-1β levels in BALF of mice subjected to single viral infection and taken at 24, 48, 72, 96, 122 hours PI. Samples were run with 2 biological repeats. Error bar represent SD and analyzed using t-test *P≤0.01.

FIGS. 12A-F. Viral loads in the lung following Anti-MT1-MMP Ab treatment 74 Hours PI (A) Representative lung tissue sections stained for influenza virus using Tamiflu, control Ab and anti-MT1-MMP Ab. Mice were infected sub-lethal dose of influenza (experimental procedures). (B-C) Bar graph quantification of influenza virus 24 and 48 hours PI. Error bar represent SD, **P≤0.001, t-test. FOV indicates the entire field of view at magnification of ×20. Number of infected cells was normalized to DAPI using ImageJ. (D) PFU values of whole lung tissue 4 days and 7 days post viral infection (experimental procedures). Samples were run in triplicates of 2 biological repeats. Error bar represent SD. LEM-1; Tami-1; Tami+LEM-1 designate the different treatments, single or combined agents, given one day before the infection (Day-1). LEM+1; Tami+1; Tami+LEM+1 designate the different treatments, single or combined agents, given one day after the infection (Day+1). LEM refers to anti-MT1-MMP Ab (LEM2/15), GST refers to non-relevant Ab. (E) Viral burdens in the lungs 24, 48 and 96 hours post infection. Whole lung homogenates were used for PFU assay, testing 2 animals at each time point and running 2 biological replicates. Error bar represent SD, *P≤0.01 using 2-way ANOVA. (F) CFU values in the lungs of co-infected mice 2 days post bacterial infection. Error bars represent SD from the mean. Data are combined from two independent experiments with five mice in each group.

FIGS. 13A-D. ECM destruction is not perturbed by low viral titers. (A) AirSEM images of lungs 74 hours post infection from either Tamiflu-treated, vehicle-treated or control mice. (B) Alveolar wall thickness measured using ImageJ (Experimental procedures), each mark represents a mean of measurements from a section-based region for an individual animal. (C) Bar graph represents viral counts in vehicle-treated and Tamiflu-treated mice lungs using qPCR. Each column represents the mean of 3 mice. Bars indicate mean and SD from the average. X-axis represents hours post viral infection. (D) MT1-MMP expression levels in mice lungs infected with 90 PFU of PR8 influenza strain undergoing different treatments. Error bar represent SD and analyzed using t-test **P≤0.001.

Figure 14A:
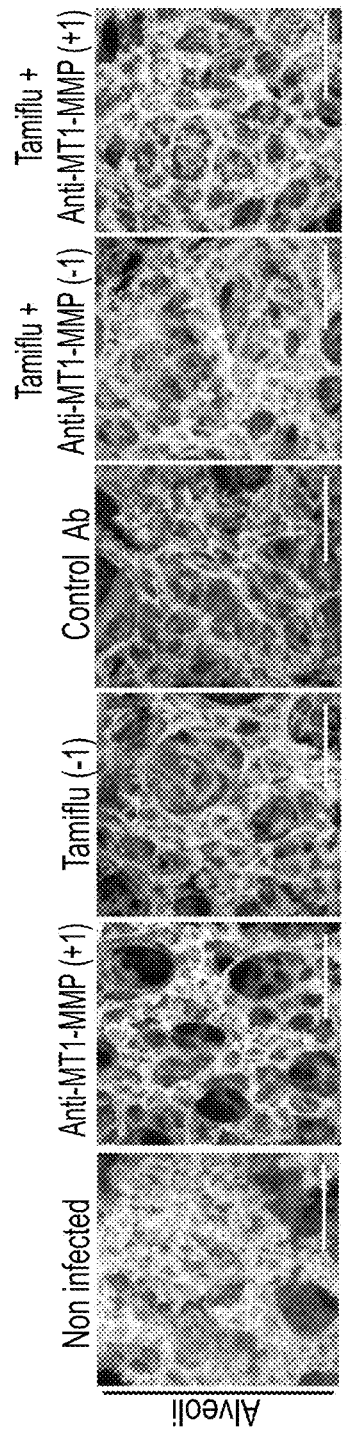
Figure 14B:
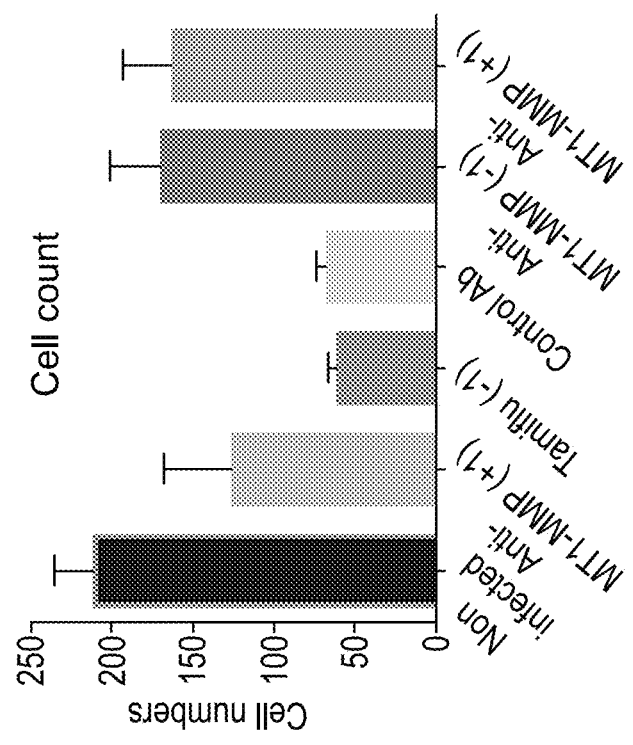

FIGS. 14A-B. Combined anti-viral and tissue protection therapy maintains lung structural features. (A) AirSEM imaging of lung sections representing changes in lung bronchi and alveoli during infection under several treatment modalities. Scale bar −20 µm. (B) Bar graph quantifying cell numbers in the different treatments taken from multiple sections.

Figure 15:
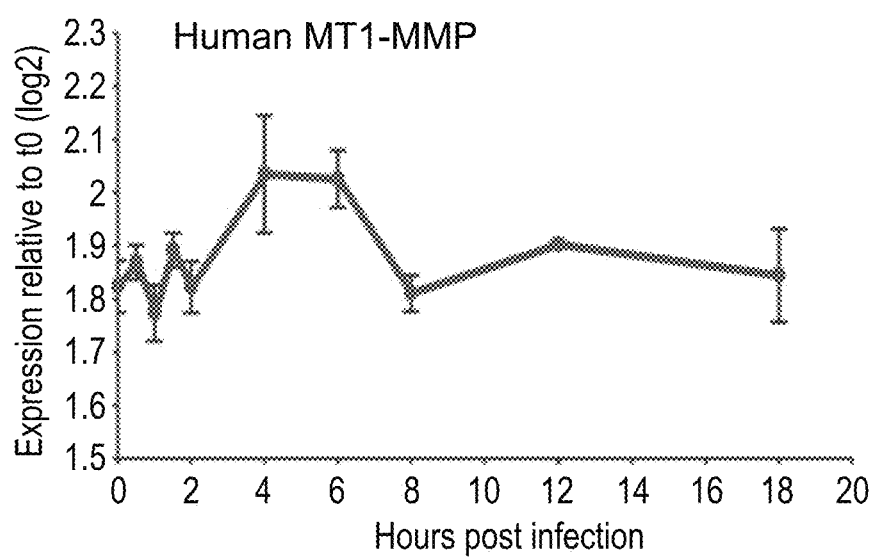

FIG. 15. MT1-MMP expression in human respiratory epithelial cells upon influenza infection. Log 2 relative expression levels of MT1-MMP correlating with the infection course (hours post infection) of human bronchial epithelial cells infected with H1N1 strain A/PR/8/34 (PR8). Error bars represent SD. Data analyzed from (Shapira S D, 2009).

DESCRIPTION OF SPECIFIC EMBODIMENTS OF THE INVENTION

The present invention, in some embodiments thereof, relates to a method of preventing secondary infections in subjects infected with a pathogen using agents that downregulate extracellular matrix remodeling.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Infectious disease treatments have conventionally focused on pathogen elimination, either by administering antimicrobial drugs or by stimulating host immune responses using vaccination. The present inventors performed global genomics and proteomics analyses of an influenza mouse model and revealed an unexpected plethora of extracellular matrix (ECM)-related genes and proteins responsible for dysregulated ECM remodeling events during the course of infection (FIGS. 1A-D and 6A-D). MT1-MMP was the main collagenase leading to destruction of ECM scaffolds of alveoli and bronchi of infected mouse lungs. Electron microscopy of intact lungs, global mass spectrometry, two-photon and immune staining, and tissue zymography, revealed a multifaceted destruction of basement membrane components (FIGS. 3A-I and 9A-D). This unprecedented damage to lungs contributed to loss of blood-air barrier and resulted in systemic spread of secondary bacterial infection through leakage from lungs to internal organs causing sepsis and mortality. These devastating phenotypes and resulting deadly outcome were reversed by blocking the activity of MT1-MMP (FIGS. 4A-K), thus offering a new mode of therapeutic intervention through tissue support. As shown in FIGS. 5A-H, combining anti-viral treatment with ECM protection supports survival and prevents systemic bacterial sepsis.

The present inventors suggest this novel treatment opportunity for infection, designed to support tissue morphology and homeostasis while mitigating inappropriate host responses and collateral tissue damage.

Thus, according to a first aspect of the present invention there is provided a method of treating a subject infected with a pathogen comprising administering to the subject a therapeutically effective amount of an anti-pathogenic agent directed towards the pathogen and a therapeutically effective amount of an agent which down-regulates at least one extracellular matrix-associated polypeptide, herein below, thereby treating the subject.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the term "subject" refers to a mammalian subject—for example a human subject.

The subjects who are treated have pathogens which cause an infection.

As used herein, the term "pathogen" refers to a microbe or microorganism such as a virus, bacterium, prion or fungus that causes a disease (e.g. a respiratory disease).

According to a particular embodiment, the pathogen is a human pathogen.

Exemplary pathogenic viruses may belong to the following families: Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, Togaviridae. Particular pathogenic viruses contemplated by the present invention are those that cause smallpox, influenza, mumps, measles, chickenpox, ebola, or rubella.

According to a particular embodiment, the virus is one which brings about a respiratory infection (e.g. an upper respiratory tract infection and/or a lower respiratory tract infection).

Thus, according to a particular embodiment, the pathogenic virus is an influenza virus (e.g. influenza virus A—(e.g. H1N1, H2N2, H3N2, H5N1, H7N7, H1N2, H9N2, H7N2, H7N3, H10N7 and H7N9), influenza virus B or influenza virus C).

In another embodiment, the pathogenic virus is a parainfluenza virus (hPIV) including the human parainfluenza virus type 1 (hPIV-1) (causes croup); the human parainfluenza virus type 2 (hPIV-2) (causes croup and other upper and lower respiratory tract illnesses), the human parainfluenza virus type 3 (hPIV-3) (associated with bronchiolitis and pneumonia) and the human parainfluenza virus type 4 (hPIV-4).

In yet another embodiment, the pathogenic virus is a respiratory syncytial virus (RSV).

Exemplary pathogenic bacteria include *Mycobacterium tuberculosis* which causes *tuberculosis, Streptococcus* and *Pseudomonas* which cause pneumonia, and *Shigella, Campylobacter* and *Salmonella* which cause foodborne illnesses. Other exemplary pathogenic bacteria contemplated by the present invention are those that cause infections such as tetanus, typhoid fever, diphtheria, syphilis and Hansen's disease.

According to one embodiment, the pathogen causes an acute infection in the subject.

According to another embodiment, the pathogen causes a chronic infection in the subject.

The term "anti-pathogenic agent" refers to an antimicrobial agent and includes, but is not limited to antiviral agents, antibacterial agents, antiviral agents, anti-prion agents.

I. Antiviral Agents

Antiviral agents which can be used for combination therapy according to aspects of the present invention include CRX4 and CCR5 receptor inhibitors such as amantadine and rimantadine and pleconaril. Further antiviral agents that can be used in the combination therapy of this aspect of the present invention include agents which interfere with viral processes that synthesize virus components after a virus invades a cell. Representative agents include nucleotide and nucleoside analogues that look like the building blocks of RNA or DNA, but deactivate the enzymes that synthesize the RNA or DNA once the analogue is incorporated. Acyclovir is a nucleoside analogue, and is effective against herpes virus infections. Zidovudine (AZT), 3TC, FTC, and other nucleoside reverse transcriptase inhibitors (NRTI), as well as non-nucleoside reverse transcriptase inhibitors (NNRTI), can also be used. Integrase inhibitors can also be used. Other antiviral agents include antisense oligonucleotides and ribozymes (directed against viral RNA or DNA at selected sites).

Some viruses, such as HIV, include protease enzymes, which cleave viral protein chains apart so they can be assembled into their final configuration. Protease inhibitors are another type of antiviral agent that can be used in the combination therapy described herein.

The final stage in the life cycle of a virus is the release of completed viruses from the host cell. Some active agents, such as zanamivir (Relenza) and oseltamivir (Tamiflu) treat influenza by preventing the release of viral particles by blocking a molecule named neuraminidase that is found on the surface of flu viruses.

Still other antiviral agents function by stimulating the patient's immune system. Interferons, including pegylated interferons, are representative compounds of this class. Interferon alpha is used, for example, to treat hepatitis B and C. Various antibodies, including monoclonal antibodies, can also be used to target viruses.

Anti-Bacterial Agents:

The antibacterial agent which can be used for combination therapy according to aspects of the present invention may be bactericidal or bacteriostatic.

In one embodiment, the antibacterial agent is an antibiotic.

As used herein, the term "antibiotic agent" refers to a group of chemical substances, isolated from natural sources or derived from antibiotic agents isolated from natural sources, having a capacity to inhibit growth of, or to destroy bacteria. Examples of antibiotic agents include, but are not limited to; Amikacin; Amoxicillin; Ampicillin; Azithromycin; Azlocillin; Aztreonam; Aztreonam; Carbenicillin; Cefaclor; Cefepime; Cefetamet; Cefinetazole; Cefixime; Cefonicid; Cefoperazone; Cefotaxime; Cefotetan; Cefoxitin; Cefpodoxime; Cefprozil; Cefsulodin; Ceftazidime; Ceftizoxime; Ceftriaxone; Cefuroxime; Cephalexin; Cephalothin; Cethromycin; Chloramphenicol; Cinoxacin; Ciprofloxacin; Clarithromycin; Clindamycin; Cloxacillin; Co-amoxiclavuanate; Dalbavancin; Daptomycin; Dicloxacillin; Doxycycline; Enoxacin; Erythromycin estolate; Erythromycin ethyl succinate; Erythromycin glucoheptonate; Erythromycin lactobionate; Erythromycin stearate; Erythromycin; Fidaxomicin; Fleroxacin; Gentamicin; Imipenem; Kanamycin; Lomefloxacin; Loracarbef; Methicillin; Metronidazole; Mezlocillin; Minocycline; Mupirocin; Nafcillin; Nalidixic acid; Netilmicin; Nitrofurantoin; Norfloxacin; Ofloxacin; Oxacillin; Penicillin G; Piperacillin; Retapamulin; Rifaxamin, Rifampin; Roxithromycin; Streptomycin; Sulfamethoxazole; Teicoplanin; Tetracycline; Ticarcillin; Tigecycline; Tobramycin; Trimethoprim; Vancomycin; combinations of Piperacillin and Tazobactam; and their various salts, acids, bases, and other derivatives. Antibacterial antibiotic agents include, but are not limited to, aminoglycosides, carbacephems, carbapenems, cephalosporins, cephamycins, fluoroquinolones, glycopeptides, lincosamides, macrolides, monobactams, penicillins, quinolones, sulfonamides, and tetracyclines.

Antibacterial agents also include antibacterial peptides. Examples include but are not limited to abaecin; andropin; apidaecins; bombinin; brevinins; buforin II; CAP18; cecropins; ceratotoxin; defensins; dermaseptin; dermcidin; drosomycin; esculentins; indolicidin; LL37; magainin; maximum H5; melittin; moricin; prophenin; protegrin; and or tachyplesins.

Anti-Fungal Agents:

The term "anti-fungal agent" refers to an agent or chemical that interferes with fungal infection through blocking spore germination, adhesion to substrates, or interfering with any metabolic process or step that is required for growth and development of the fungus or its spores.

Anti-Protozoal Agent:

The term "anti-protozoal" as used herein refers to any chemical or agent that interferes with the parasitic or other life cycle features of a broad range of eukaryotic microbes and invertebrate worms. The agent or chemical might block protein synthesis, essential lipid production, respiratory processes or other metabolic events or growth control steps.

As mentioned herein above, the present invention contemplates administering both an agent directed against the pathogen (as detailed herein above) and an agent which down-regulates at least one extracellular matrix-associated polypeptide.

The term one extracellular matrix-associated polypeptide refers to a polypeptide that reduces the formation or enhances the degradation of the extracellular matrix or is comprised in the extracellular matrix.

According to a particular embodiment, the extracellular matrix-associated polypeptide is a fibrous protein such as collagen, elastin, fibronectin, and laminin.

According to another embodiment, the extracellular matrix-associated polypeptide is a protease such as a matrix metalloproteinase, an enzyme belonging to the class A Disintegrin And Metalloproteinase with Thrombospondin Motifs (ADAMTS) including ADAMTS1-17 and those belonging to the lysyl oxidase family such as Lysyl oxidase homolog 2 (LOXL).

In one embodiment, the extracellular matrix-associated polypeptide is set forth in Table 2B of the Examples section herein below.

Preferably, the extracellular matrix-associated polypeptide is set forth in Table 1, herein below. Exemplary cDNA sequences of each of the genes are provided therein.

TABLE 1

| Symbol | Gene (Human) | SEQ ID | Gene (mouse) |
|---|---|---|---|
| TIMP1 | NM_003254.2 | 1 | NM_001044384 |
| ADAMTS4 | NM_005099.4 | 2 | NM_172845 |
| TNC | NM_002160.3 | 3 | NM_011607 |
| VCAN | NM_001126336.2 | 4 | NM_001134475 |
| THBS1 | NM_003246.3 | 5 | NM_011580 |
| PLAU | NM_001145031.1 | 6 | NM_008873 |
| HAS1 | NM_001297436.1 | 7 | NM_008215 |
| SERPINA3 | NM_001085.4 | 8 | NM_001033335 (3F), NM_009253 (3M), NM_009251 (3G) NM_009252 (3N) |
| SERPINE1 | NM_000602 | 9 | NM_008871 |
| MMP3 | NM_002422.3 | 10 | NM_010809 |
| ADAMTS15 | NM_139055.2 | 11 | NM_001024139 |
| PRSS22 | NM_022119.3 | 12 | NM_133731 |
| ITGA5 | NM_002205.2 | 13 | NM_010577 |
| LGMN | NM_005606.6 | 14 | NM_011175 |
| MMP14 | NM_004995.3 | 15 | NM_008608 |
| GZMB | NM_004131.4 | 16 | NM_013542 |
| MMP9 | NM_004994.2 | 17 | NM_013599 |
| LCN2 | NM_005564.3 | 18 | NM_008491 |
| MMP8 | NM_001304441.1 | 19 | NM_008611 |
| LOXL3 | NM_001289164.1 | 20 | NM_013586 |
| AIF1 | NM_001623.3 | 21 | NM_019467 |
| LOXL2 | NM_002318.2 | 22 | NM_033325 |
| TIMP3 | NM_000362.4 | 23 | NM_011595 |
| LOXL1 | NM_005576.3 | 24 | NM_010729 |
| ADAM8 | NM_001109.4 | 25 | NM_007403 |
| SERPING1 | NM_000062.2 | 26 | NM_009776 |
| SERINC3 | NM_006811.2 | 27 | NM_012032 |

Downregulation of ECM-associated polypeptides can be effected on the genomic and/or the transcript level using a variety of molecules which interfere with transcription and/or translation [e.g., RNA silencing agents (e.g., antisense, siRNA, shRNA, micro-RNA), Ribozyme and DNAzyme], or on the protein level using e.g., antagonists, enzymes that cleave the polypeptide and the like.

Following is a list of agents capable of downregulating expression level and/or activity of ECM-associated polypeptides.

One example, of an agent capable of ECM-associated polypeptides is an antibody or antibody fragment capable of specifically binding thereto and down-regulating activity thereof.

Preferably, the antibody binds with a Ki of less than 1000 nm, more preferably less than 100 nm and even more preferably less than 10 nm to its target polypeptide.

Preferably, the antibody specifically binds at least one epitope of the polypeptide. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

According to one embodiment, the epitopic determinant is on the surface of the polypeptide.

According to another embodiment, when the polypeptide is a matrix metalloproteinase (MMP) such as MT1-MMP1, MMP-9, MMP-8 and MMP-3 the antibody binds to (and may optionally be generated by immunizing with) a hapten compound, [2-(2-minoethylcarbomoyl)-ethoxymethyl]-tris-[2-(N-(3-imidazol-1-yl-propyl))-ethoxymethyl]methane. This hapten molecule closely mimics the local structure and conformation of the reactive zinc site inMMPs (see WO 2008/102359, the contents of which are incorporated herein by reference).

In one embodiment, the antibody is capable of specifically binding to the active form of the antibody and not to the proenzyme form.

Preferably, the antibody is specific to the particular matrix metalloproteinase (MMP) and binds with at least 5 times higher affinity to that particular MMP than a non relevant MMP.

According to a specific embodiment, the polypeptide is MT1-MMP1, also known as MMP-14.

Examples of antibodies that bind and down-regulate MMP-14 include those produced by the LEM-2/15 hybridoma cells as detailed in Udi et al., Structure 23, 1-12, Jan. 6, 2015, the contents of which are incorporated herein by reference.

According to another embodiment, the antibody targets a surface epitope of MMP-14. Thus, for example the antibody may bind to the VB loop of MMP-14 (for example residues 160-173 and/or residues 218-233 of MMP-14). In another embodiment, the antibody is one which causes a conformational swiveling motion of the V-B loop of MMP-14.

An exemplary amino acid sequence of the $V_H$ of a MMP-14 downregulating antibody is presented in SEQ ID NO: 54. An exemplary amino acid sequence of the $V_L$ of a MMP-14 downregulating antibody is presented in SEQ ID NO: 55.

In yet another embodiment, the antibody is such that it down-regulates the collagenase activity of MMP-14, but does not affect the activation of pro-MMP-2.

Additional antibodies which down-regulate MMP-14 are disclosed in U.S. Pat. No. 8,501,181 and Devy et al., Biochemistry Research International, Volume 2011, Article ID 191670, 11 pages, doi:10.1155/2011/191670.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to some embodiments of the invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Down-regulation of ECM-associated polypeptides can be also achieved by RNA silencing. As used herein, the phrase "RNA silencing" refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or "silencing" of the expression of a corresponding protein-coding gene. RNA silencing has been observed in many types of organisms, including plants, animals, and fungi.

As used herein, the term "RNA silencing agent" refers to an RNA which is capable of specifically inhibiting or "silencing" the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

According to an embodiment of the invention, the RNA silencing agent is specific to the target RNA (e.g., MMP-14) and does not cross inhibit or silence a gene or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplate use of dsRNA to down-regulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl Acad. Sci. USA. 2002; 99:1443-1448; Tran N., et al., FEBS Lett. 2004; 573:127-134].

In particular, the invention according to some embodiments thereof contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13(5): 381-392. doi:10.1089/154545703322617069.

The invention according to some embodiments thereof also contemplates introduction of long dsRNA specifically designed not to induce the interferon and PKR pathways for down-regulating gene expression. For example, Shinagwa and Ishii [*Genes & Dev.* 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly(A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21mers with a central 19 bp duplex region and symmetric 2-base 3'-overhangs on the termini, although it has been recently described that chemically synthesized RNA duplexes of 25-30 base length can have as much as a 100-fold increase in potency compared with 21mers at the same location. The observed increased potency obtained using longer RNAs in triggering RNAi is theorized to result from providing Dicer with a substrate (27mer) instead of a product (21mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned above the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. It will be recognized by one of skill in the art that the resulting single chain oligonucleotide forms a stem-loop or hairpin structure comprising a double-stranded region capable of interacting with the RNAi machinery.

It will be appreciated that the RNA silencing agent of some embodiments of the invention need not be limited to those molecules containing only RNA, but further encompasses chemically-modified nucleotides and non-nucleotides.

In some embodiments, the RNA silencing agent provided herein can be functionally associated with a cell-penetrating peptide." As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of some embodiments of the invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of some embodiments of the invention preferably include, but are not limited to, penetratin, transportan, plsl, TAT(48-60), pVEC, MTS, and MAP.

mRNAs to be targeted using RNA silencing agents include, but are not limited to, those whose expression is correlated with an undesired phenotypic trait. Exemplary mRNAs that may be targeted are those that encode truncated proteins i.e. comprise deletions. Accordingly the RNA silencing agent of some embodiments of the invention may be targeted to a bridging region on either side of the deletion. Introduction of such RNA silencing agents into a cell would cause a down-regulation of the mutated protein while leaving the non-mutated protein unaffected.

According to another embodiment the RNA silencing agent may be a miRNA or miRNA mimic.

The term "microRNA", "miRNA", and "miR" are synonymous and refer to a collection of non-coding single-stranded RNA molecules of about 19-28 nucleotides in length, which regulate gene expression. miRNAs are found in a wide range of organisms (viruses.fwdarw.humans) and have been shown to play a role in development, homeostasis, and disease etiology.

The term "microRNA mimic" refers to synthetic non-coding RNAs that are capable of entering the RNAi pathway and regulating gene expression. miRNA mimics imitate the function of endogenous microRNAs (miRNAs) and can be designed as mature, double stranded molecules or mimic precursors (e.g., or pre-miRNAs). miRNA mimics can be comprised of modified or unmodified RNA, DNA, RNA-DNA hybrids, or alternative nucleic acid chemistries (e.g., LNAs or 2'-0,4'-C-ethylene-bridged nucleic acids (ENA)). For mature, double stranded miRNA mimics, the length of the duplex region can vary between 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA.

Another agent capable of downregulating ECM-associated polypeptides is a DNAzyme molecule capable of specifically cleaving an mRNA transcript or DNA sequence of the polypeptide.

Downregulation ECM-associated polypeptides can also be effected by using an antisense polynucleotide capable of specifically hybridizing with an mRNA transcript encoding same.

Another agent capable of downregulating ECM-associated polypeptides is a ribozyme molecule capable of specifically cleaving an mRNA transcript encoding same.

Another agent capable of downregulating ECM-associated polypeptides would be any molecule which binds to and/or cleaves the polypeptide. Such molecules can be antagonists, or inhibitory peptide.

For example, Zarrabi et al (J Biol Chem. 2011 Sep. 23; 286(38): 33167-33177) discloses peptides that inhibit MMP-14.

It will be appreciated that a non-functional analogue of at least a catalytic or binding portion of any of the disclosed polypeptides can be also used as an agent which down-regulates ECM-associated polypeptides.

Another agent which can be used along with some embodiments of the invention to down-regulate the ECM-associated polypeptides is a molecule which prevents activation or substrate binding thereto.

Additional exemplary inhibitors of matrix metalloproteinases include the hydroxamate inhibitors, small peptide analogs of fibrillar collagens, which specifically interact in a bidentate manner via the hydroxyl and carbonyl oxygens of the hydroxamic group with the zinc ion in the catalytic site [Grams et al., (1995), Biochem. 34: 14012-14020; Bode et al., (1994), EMBO J., 13: 1263-1269].

Hydroxamate-based MMP inhibitors are usually composed of either a carbon back-bone (WO 95/29892, WO 97/24117, WO 97/49679 and EP 0780386), a peptidyl back-bone (WO 90/05719, WO 93/20047, WO 95/09841 and WO 96/06074) or a peptidomimetic back-bone [Schwartz et al., Progr. Med. Chem., 29: 271-334(1992); Rasmussen et al., Pharmacol. Ther., 75: 69-75 (1997); Denis et al., Invest. New Drugs, 15: 175-185 (1997)]. Alternatively, they contain a sulfonamido sulfonyl group which is bonded on one side to a phenyl ring and a sulfonamido nitrogen which is bonded to an hydroxamate group via a chain of one to four carbon atoms (EP 0757984 A1).

Other peptide-based MMP inhibitors are thiol amides which exhibit collagenase inhibition activity (U.S. Pat. No. 4,595,700), N-carboxyalkyl derivatives containing a biphenylethylglycine which inhibit MMP-3, MMP-2 and collagenase (Durette, et al., WO-9529689), lactam derivatives which inhibit MMPs, TNF-alpha and aggrecanase (see U.S. Pat. No. 6,495,699) and Tricyclic sulfonamide compounds (see U.S. Pat. No. 6,492,422).

Other MMP inhibitors are the chemically modified non-microbial tetracyclines (CMTs) that were shown to block expression of several MMPs in vitro. (Axisa et al., 2002, Stroke 33: 2858-2864).

Recently, a mechanism-based MMP inhibitor, SB-3CT, was designed according to the X-ray crystallographic information of the MMP active site (Brown et al., 2000). X-ray absorption studies revealed that binding of this molecule to the catalytic zinc reconstructs the conformational environment around the active site metal ion back to that of the pro-enzyme [Kleifeld et al., 2001, J Biol. Chem. 276: 17125-31].

In the context of a combination therapy, combination therapy compounds may be administered by the same route of administration (e.g. intrapulmonary, oral, enteral, etc.) that the described compounds are administered. In the alternative, the agents for use in combination therapy with the herein described agents may be administered by a different route of administration.

The agent which down-regulates ECM-associated polypeptides can be administered immediately prior to (or after) the anti-pathogenic agent, on the same day as, one day before (or after), one week before (or after), one month before (or after), or two months before (or after) the anti-pathogenic agent, and the like.

The agents which down-regulate ECM-associated polypeptides and the anti-pathogenic agent can be administered concomitantly, that is, where the administering for each of these agents can occur at time intervals that partially or fully overlap each other. The agents described herein can be administered during time intervals that do not overlap each other. For example, the first agent can be administered within the time frame of t=0 to 1 hours, while the second agent can be administered within the time frame of t=1 to 2 hours. Also, the first agent can be administered within the time frame of t=0 to 1 hours, while the second agent can be administered somewhere within the time frame of t=2-3 hours, t=3-4 hours, t=4-5 hours, t=5-6 hours, t=6-7 hours, t=7-8 hours, t=8-9 hours, t=9-10 hours, and the like. Moreover, the second agent can be administered somewhere in the time frame of t=minus 2-3 hours, t=minus 3-4 hours, t=minus 4-5 hours, t=5-6 minus hours, t=minus 6-7 hours, t=minus 7-8 hours, t=minus 8-9 hours, t=minus 9-10 hours.

The agents of the present invention are typically provided in combined amounts to treat the infection and/or to reduce symptoms or disease associated with a secondary infection. This amount will evidently depend upon the particular agent selected for use, the nature and number of the other treatment modality, the condition(s) to be treated, prevented and/or palliated, the species, age, sex, weight, health and prognosis of the subject, the mode of administration, effectiveness of targeting, residence time, mode of clearance, type and severity of side effects of the agents and upon many other factors which will be evident to those of skill in the art.

The present inventors have shown that administration of an antibody which binds to and down-regulates MMP-14 prevents complications of a secondary infection. More specifically, the present inventors showed that administration of an MMP-14 antibody together with an antiviral agent reduced the symptoms in animals infected with the influenza virus (as the primary infection) and *S. pneumoniae* (as the secondary infection).

Thus, the present inventors propose that administration of agents which specifically down-regulate ECM-associated polypeptides and an antipathogenic agent may prevent (or reduce the symptoms of) a secondary infection.

Thus, according to another aspect of the present invention there is provided a method of treating or preventing a disease associated with a secondary infection in a subject infected with a pathogen comprising administering to the subject a therapeutically effective amount of an anti-pathogenic agent directed towards the pathogen and a therapeutically effective amount of an agent which down-regulates an ECM-associated polypeptide, thereby treating or preventing the disease associated with the secondary infection in the subject.

As used herein, the phrase "secondary infection" refers to an infection that occurs during or after treatment of another pre-existing infection. It may result from the treatment itself or from changes in the immune system.

The term "preventing" refers to inhibiting or arresting the development of the secondary infection and/or causing the prevention, reduction, remission, or regression of symptoms of the secondary infection.

According to a particular embodiment, the combination therapy proposed by the present invention reduces the complications or treats a disease (e.g. sepsis) associated with the secondary infection.

The secondary infection may be a bacterial infection, a viral infection or a fungal infection.

The primary and the secondary infections are typically infections of the same organ (e.g. lungs and/or respiratory tract).

In one embodiment, the primary infection is viral infection (e.g. influenza) and the secondary infection is a bacterial infection (e.g. *S. pneumoniae*).

In another embodiment, the primary infection is a bacterial infection and the secondary infection is a viral infection.

In yet another embodiment, the primary infection is viral infection and the secondary infection is a fungal infection.

In yet another embodiment, the primary infection is a bacterial infection and the secondary infection is a fungal infection.

According to yet another aspect of the present invention there is provided a method of treating influenza in a subject in need thereof comprising administering to the subject a therapeutically effective amount of an agent which down-regulates at least one ECM-associated polypeptide, thereby treating the influenza.

ECM-associated polypeptides have been described herein above. According to a particular embodiment, the ECM-associated polypeptide is set forth in Table 1—for example MT1-MMP1.

According to a particular embodiment, treatment of influenza is effected by administering an antibody which down-regulates an amount of MT1-MMP1, such as those described herein above.

In order to prevent the collapse of the ECM, preferably, the agent is provided no more than 5 days after the start of symptoms of the influenza virus, no more than 4 days after the start of symptoms of the influenza virus, no more than 3 days after the start of symptoms of the influenza virus, no more than 2 days after the start of symptoms of the influenza virus, and even no more than 1 day after the start of symptoms of the influenza virus.

In any of the method and uses described herein, the agents can be used per se or in a pharmaceutical composition which further comprises a pharmaceutically (or cosmetically) acceptable carrier.

In one embodiment, the agents are co-formulated in the same pharmaceutical composition.

In another embodiment, the agents are formulated in separate pharmaceutical compositions. The separate pharmaceutical compositions may be comprised in a single article of manufacture, e.g. a kit.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to any of the agents described herein. It will be appreciated that the pharmaceutical compositions may comprise additional active agents known to be useful in treating a particular disease.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

According to a particular embodiment, the route of administration is via topical delivery.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum Arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (e.g. the compounds described herein) effective to prevent, alleviate or ameliorate symptoms of a disorder (e.g., fibrotic or inflammatory disease) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated from animal models to achieve a desired concentration or titer. Such information can be used to more accurately determine useful doses in humans.

Toxicity and therapeutic efficacy of the active ingredients described herein can be determined by standard pharmaceutical procedures in experimental animals. The data obtained from these animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide cell numbers sufficient to induce normoglycemia (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

It is expected that during the life of a patent maturing from this application many relevant antiviral/antibacterial agents will be developed and the scope of the term antiviral/antibacterial is intended to include all such new technologies a priori.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as Materials and Methods Influenza Virus and *Streptococcus pneumoniae* Bacterial Agent:

Mouse-adapted PR8 virus, influenza A/Puerto Rico/8/34 (A/PR/8/34, H1N1) was persistently grown in hen egg amnion and influenza effective titers were quantified as previously described (Achdout et al., 2003). *Streptococcus pneumoniae* (*S. pneumoniae*) D39 type 2 encapsulated strain was grown in Todd-Hewitt broth (Difco Laboratories) For isolation and infection of mice, bacteria were grown overnight on tryptic soy agar (Hylab Laboratories) supplemented with 3% (vol/vol) sheep erythrocyte at 37° C. and were then harvested by centrifugation at 4000 g for 20 min to pellet the bacteria and dilute it to the desired concentration.

Infection Procedures:

Female C57BL/6J mice (4-5 weeks of age) were anesthetized with ketamine-xylazine and were intra-nasally inoculated with 50 µl of diluted virus. The same stock was used for all the experiments containing influenza A/Puerto Rico/8/34 (A/PR/8/34, H1N1) strain, $9 \times 10^7$ PFU/ml, HA 1:1,024. To study pathogenesis of Influenza infection, C57BL/6 mice were intra-nasally infected with $4 \times 10^3$ PFU of influenza PR8 virus equivalent to lethal dose. Mice were sacrificed on 3, 7, 11, 26, 32, 49, 74, 98, 122, 148 hours post infection and the lungs were harvested and homogenized for RNA isolation. To study the effectivity of anti-MT1-MMP inhibitor, both in the single viral infection model and in the double infection model combining *S. pneumoniae*, a sub-lethal dose of 800 PFU was used, which was diluted accordingly and administered along the same route. *S. pneumoniae* was grown on tryptic soy agar (Hylab Laboratories) supplemented with 3% (vol/vol) sheep erythrocytes. The bacterium was diluted in sterile PBS and administered intra-nasally 4 days post viral infection at a dose of 30 CFU, in a volume of 504 The mice were anesthetized and held in an upright position while inoculated. Mice were weighted and monitored at least daily for illness and mortality. All animal procedures were performed according to IACUC guidelines and were approved by the committee of the Weizmann Institute of Science.

Treatment of Animals:

Mice were treated in the single infection experiments as well as in the co-infection experiments with 3 mg/kg of LEM 2/15 Fab fragment at a total volume of 100 µl per injection, given intra-peritoneally every day. GST-Fab, designated in text as control Fab, served as non-relevant control and was given the same dose as the LEM 2/15 treated group. PBS used as a vehicle control.

LEM 2/15 (Anti-MT1-MMP Ab) Purification:

Hybridoma cells of LEM-2/15 were grown in DCCM (serum-free medium designed for hybridoma cell growth and monoclonal antibody production, purchased from Biological Industries). Cells were precipitated by centrifugation at 193 g, and the supernatant was collected. The supernatant was dialyzed against 20 mM phosphate buffer (pH 8). A 1 ml HiTrap protein A high-performance column was equilibrated with 100 mM phosphate buffer (pH 8), and the supernatant was loaded at 1 ml/min. The antibody was eluted with 100 mM citrate buffer (pH 6) and dialyzed against 50 mM Tris-HCl (pH 7.5) and 150 mM NaCl.

Antibody Digestion with Papain:

Papain was activated in 0.5 M Tris-HCl (pH 8), 10 mM EDTA, and 5 mM dithiothreitol for 15 min at 370 C. Active papain was added to a solution of intact LEM-2/15 at a ratio of 1:1,000, and the digestion process was carried out for 3 h at 370 C. The digestion reaction was terminated with the addition of 20 mM iodoacetamide in the dark at room temperature for 30 min. The Fab fragment was isolated from the Fc by a protein A column, and the Fab fragment was collected from the flow through and dialyzed against 50 mM Tris-HCl (pH 7.5) and 150 mM NaCl. The purity of the Fab fragment was estimated by 12% SDS-PAGE gel. Pure Fab fragment was filtered to assure sterility and kept at −80° C. conditions until use.

Glutathione S-Transferases (GST)-Fab Fragment:

Fab fragment from the whole GST antibody were produced as described in the upper section (Antibody Digestion with Papain).

Quantification of Viral and Bacterial Loads:

Viral titers in the lungs were determined by titration of organ homogenate on MDCK cells and plaque forming units (PFUs) were quantified as described in (Okuda et al., 2001). Strep. pneumoniae levels were determined by plating titrated amounts of organ homogenate on tryptic soy agar plates supplemented with 3% sheep erythrocytes (Hylab Laboratories). Organs were homogenized using the GentleMACS 1ml of appropriate buffer for PFUs or 10 ml of sterile water for Strep. pneumoniae for CFUs. Viral burdens were also quantified using qPCR, as described before for the detection of virus in patients (Hindiyeh et al., 2005). *S. pneumoniae* identification was done using qPCR as previously described (Ogunniyi et al., 2002). Serial dilutions of Influenza A (A/PR/8/34) virus titrated on Madin-Darby Canine Kidney (MDCK) cells were used as standards to determine the quantity of the influenza virus by quantitative real-time PCR (qRT-PCR) and convert the qPCR results into viral load numbers.

RNA Isolation:

Lungs were removed and immediately transferred into RNA Latter solution (Invitrogen). For RNA isolation, the lung was cut into small pieces in the presence of QIAzol, homogenized using SPEX CertiPrep homogenizer, and total RNA was extracted with a miRNeasy Mini Kit (Qiagen). RNA integrity was determined (Tapestation, Agilent Technologies) and concentration measured with a Qubit Fluorometric Quantitation device (LifeTechnologies).

Preparation of RNA Sequencing Libraries:

For RNA-seq a derivation of MARS-seq technique was used as described in (Jaitin et al., 2014). In brief, total RNA was fragmented into fragments having an average size of 300 nucleotides by chemical heat (95° C.) treatment for 4:30 min (NEBNext Magnesium RNA Fragmentation Module). The 3' polyadenylated fragments were enriched by selection on poly dT beads (Dynabeads Invitrogen). Strand-specific cDNA was synthesized using a poly T-VN oligo (18 T) and Affinity Script RT enzyme (Agilent). Double-strand DNA was obtained using Second strand synthesis kit (NEB). DNA ends were repaired using T4 polynucleotide kinase and T4 polymerase (NEB-Next). After the addition of an adenine base residue to the 5' end using Klenow enzyme (NEB-Next), a barcode Illumina compatible adaptor (IDT) was ligated to each fragment. The washed DNA fragment was amplified by PCR (12 cycles) using specific primers (IDT) to the ligated adaptors. The quality of each library was analyzed by TapeStation (Agilent).

Pre-Processing of RNA Seq Data:

RNA-seq was performed as described in Lavin et al., 2014. In brief, all reads, both from whole lung (FIGS. 1A-D) and cell populations (FIG. 8) were aligned to the mouse reference genome (NCBI 37, MM9) using the TopHat aligner. Normalized expression table was created using ESAT garberlabdotumassmeddotedu/software/esat/based on the negative binomial distribution and a local regression model. Data manipulation-Discard genes from table that have values>0 only once; Calculate 75 percentile of data result is 33 (set noise to 32); Find max of raw and discard if max<32; log 2 values as x+32; Average replicates; keep rows where max−min>0.8 (notice not 2 fold but 1.75); K-Means in matlab for 20 clusters; manually ordered the clusters for visual purpose picture was done in GeneE.

qPCR:

Total RNA was reverse transcribed to cDNA using high capacity cDNA reverse transcription kit (Applied Biosystems). RT-PCR was performed with LightCycler480 SYBR green I master mix (Roche) in triplicate, using GAPDH and f3-actin for normalization. Primer list is provided in Table 2A, herein below.

TABLE 2A

| Gene | Direction | sequence | SEQ ID |
|---|---|---|---|
| MT1-MMP | Forward | 5-AGCACTGGGTGTTTGACG-3 | 28 |
| MT1-MMP | Reverse | 5-GTCTTCCCATTGGGCATC-3 | 29 |
| MMP-9 | Forward | 5-CAGACGTGGGTCGATTCC-3 | 30 |
| MMP-9 | Reverse | 5-TCATCGATCATGTCTCGC-3 | 31 |
| MMP-8 | Forward | 5-GCAGCGCTTCTTCAGCTT-3 | 32 |
| MMP-8 | Reverse | 5-GTGTGTGTCCACTTGGGA-3 | 33 |
| MMP-2 | Forward | 5-ACGATGATGACCGGAAGT-3 | 34 |
| MMP-2 | Reverse | 5-GTGTAGATCGGGGCCATC-3 | 35 |
| TIMP1-var2 | Forward | 5-GCAGTGATTTCCCCGCCA-3 | 36 |
| TIMP1-var2 | Reverse | 5-GGGGGCCATCATGGTATC-3 | 37 |
| MMP-3 | Forward | 5-AAGGAGGCAGCAGAGAAC-3 | 38 |
| MMP-3 | Reverse | 5-GCACTGTCATGCAATGGG-3 | 39 |
| LGMN | Forward | 5-GCCTACCAGATCATCCAC-3 | 40 |
| LGMN | Reverse | 5-ACATCTGTGCCGTTAGGT-3 | 41 |
| GZMB | Forward | 5-ACAACACTCTTGACGCTG-3 | 42 |
| GZMB | Reverse | 5-CGAGAGTGGGGCTTGACT-3 | 43 |
| LCN2 | Forward | 5-ACAACCAGTTCGCCATGG-3 | 44 |
| LCN2 | Reverse | 5-AAGCGGGGTGAAACGTTCC-3 | 45 |
| PR8 MATRIX A INF A-CDC | Forward | 5-GACCRATCCTGTCACTGAC-3 | 46 |
| PR8 MATRIX A INF A-CDC | Reverse | 5-TGCAGTCCTCGCTCACTGGGCACG-3 | 47 |
| 16S rRNA | Forward | 5-GGTGAGTAACGCGTAGGTAA-3 | 48 |
| 16S Rrna | Reverse | 5-ACGATCCGAAAACCTTCTTC-3 | 49 |
| TIMP-2 | Forward | TCTAGGAGTCCCAGTCAGCC | 50 |
| TIMP-2 | Reverse | CAACAAGGACTGCCAAGCAC | 51 |
| GAPDH | Forward | GCCCTTGAGCTAGGACTGGA | 52 |
| GAPDH | Reverse | TACGGCCAAATCCGTTCACA | 53 |

In Gel Proteolysis and Mass Spectrometry Analysis:

Lung samples were de-cellularized using 0.5% EDTA supplemented with 2% triton, shaking for 24 hours. Samples were then dehydrated using a Speedvac and weighted. Samples were then subjected to in-solution digestion using activated MMP-13, 500 nM in TNC buffer in (50 mM Tris-HCl, 150 mM NaCl, 5 mM MgCl2, 5 mM CaCl2, pH 7.4) a volume of 120 µl, for 24 hours shaking at 30° C. The volume and concentration of activated MMP-13 were adjusted according to the weight of each sample, and each sample was run in duplicates. Protein extract was loaded on SDS-PAGE for a short run. The proteins in the gel were reduced with 2.8 mM DTT (60° C. for 30 min), modified with 8.8 mM iodoacetamide in 100 mM ammonium bicarbonate (in the dark, room temperature for 30 min) and digested in 10% acetonitrile and 10 mM ammonium bicarbonate with modified tryp sin (Promega) at a 1:10 enzyme-to-substrate ratio, overnight at 37° C. An additional second trypsinization was done for 4 hours. The resulting tryptic peptides were resolved by reverse-phase chromatography on 0.075×200-mm fused silica capillaries (J&W) packed with Reprosil reversed phase material (Dr Maisch GmbH, Germany). The peptides were eluted with linear 95 minutes gradients of 7 to 40% and 8 minutes at 95% acetonitrile with 0.1% formic acid in water at flow rates of 0.25 µl/min. Mass spectrometry was performed by an ion-trap mass spectrometer (Orbitrap XP, Thermo) in a positive mode using repetitively full MS scan followed by collision induces dissociation (CID) of the 7 most dominant ion selected from the first MS scan.

The mass spectrometry data was analyzed using the MaxQuant 1.3.0.5 software searching against the mouse section of the Uniprot database with mass tolerance of 20 ppm for the precursor masses. Peptide- and protein-level false discovery rates (FDRs) were filtered to 1% using the target-decoy strategy. Protein table were filtered to eliminate the identifications from the reverse database, and common contaminants and single peptide identifications. The data was quantified by label free analysis using the same software, based on extracted ion currents (XICs) of peptides enabling quantitation from each LC/MS run for each peptide identified in any of experiments. To search for ECM related proteins, annotations were determined using the GORILLA Bioinformatics Resources.

Western Blot:

Lung samples were homogenized using gentleMACS (Miltenyi Biotec) according to manufacturer instructions using 500 µl rippa buffer containing protease inhibitor cocktail (Roche). Protein levels were then measured using BCA kit (Pierce Biotechnology) and run in duplicates on SDS-PAGE gel using a mini-electrophoresis apparatus (Bio-Rad Laboratories, Inc.). The resolved polypeptides were transferred onto a nitrocellulose membrane in Tris-glycine buffer containing 25% methanol. The membranes were blocked with 5% dried milk, and then incubated with goat anti-MMP-8 (SantaCruz), rabbit anti-MMP-9 (Abcam) or rabbit anti-MT1MMP (Abcam) antibodies. Rabbit anti-GAPDH (SantaCruz) was included in each procedure to avoid inter-assay variations. Nitrocellulose membranes were incubated with goat anti-rabbit HRP conjugated antibody (Abcam), or bovine anti-goat HRP (Sigma). Membranes were developed using EZ-ECL chemiluminescence detection kit (Biological industries). A molecular mass protein standard (PageRuler Prestained Protein ladder, Fermentas) was included in each assay.

Lung Preparation for Imaging:

Lungs were inflated by using PBS for in situ zymography or 4% PFA for other imaging purposes. This was done by exposing the trachea, inserting a cannula 22G, 0.8×25 mm, (Cathy IV cannula, HMD Healthcare LTD) and injecting 5 ml fluid. The cannula was ligated to the trachea to avoid spillage. Mouse lungs were harvested at different time points post infection, embedded in OCT and frozen in −80° C. until analyzed.

Two-Photon Microscopy and Second Harmonics Generation:

Before imaging, lungs were cut 300 µm and immediately visualized using a two-photon microscope in the in-vivo imaging unit in the Weizmann institute (2PM:Zeiss LSM 510 META NLO; equipped with a broadband Mai Tai-HP-femtosecond single box tunable Ti-sapphire oscillator, with automated broadband wavelength tuning 700-1,020 nm from Spectraphysics, for two-photon excitation). For collagen second harmonic imaging a wavelength of 800 nm was used (detection at 400 nm).

AirSEM and SEM Imaging of Intact Lung Tissues and Lung ECM Scaffolds:

Fixed lungs were sectioned into 300 µm sections. Sections were washed three times in a large volume of PBS to remove OCT remnants, followed by three DDW washes. For tissue imaging, the slices were gently placed on a SuperFrost Plus glass slides and stained as previously described. Briefly, sections were washed with DDW and stained with 0.1% ruthenium red (EM grade, Sigma-Aldrich) in a 0.1 M sodium cacodylate buffer pH 7.4 (analytical standard, Sigma-Aldrich) for 15 min. The sections were then thoroughly washed with DDW and stained with a 2% uranyl acetate solution for 10 min. The samples were then washed with DDW and allowed to dry in the air at room temperature for 5-7 min before airSEM™. ECM scaffolds were first de-cellularized using 0.5% EDTA supplemented with 2% triton for 24 hours. Staining was done as previously described. For conventional scanning electron microscopy (SEM) samples were further dehydrated through an ethanol series increasing in concentration to 100% ethanol, were dried in a critical point dryer and coated by Au/Palladium according to standard sample preparation procedure for SEM imaging with an Ultra 55 Feg Zeiss SEM operating at 2 kV.

Immunohistochemistry:

Immunohistochemistry was performed using standard techniques on 10 µm cryo-sections. Sections were fixed with 4% PFA, blocked with 3% BSA, incubated overnight with primary rabbit anti-laminin (Sigma), or rabbit anti-lumican (abcam), or rabbit anti-collagen IV or rat antibody for F4/80 and CD45 cell surface protein (abcam). LEM2/15 was conjugated to Alexa Fluor 555 Protein by Labeling Kit (Molecular Probes), according to manufacturer's instructions. Sections were then washed with PBS, incubated with a goat anti-rabbit HRP conjugated (Jackson). Fluorescein or Cy3 conjugated anti-HRP kit was used (Perkin Ehlmer) respectively, followed by DAPI staining (Sigma) and mounting with immune-mount (Thermo Scientific). Samples were imaged using Nikon 80i eclipse microscope.

Collagen Type I in Situ Zymography:

Non-fixed lungs samples were cut into 10 µm sections, gently washed to remove OCT. After washing a 1 mg/ml DQ collagen type I (Molecular Probes) was diluted to 40 mg/ml with developing buffer (50 mM Tris (pH 7.5), 100 mM NaCl, 5 mM CaCl2). Samples were incubated for 4 hours at 37° C. the reaction was stopped with 4% paraformaldehyde and followed by the desired immune-staining, mounted with immune-mount (Thermo Scientific) and imaged using Nikon 80i eclipse microscope.

Relative Frequency of Fiber Orientation Analysis:

Imaging analysis was done by Fiji package, Directionality analysis. Graphs were plotted using GraphPad Prism 6. The relative frequency of fiber spatial orientation was measured using the "Directionality" plugin analysis tool in Fiji package version 6.1.1.

Flow Cytometry:

Lungs from infected and control uninfected C57BL/6J mice were immersed in cold PBS, cut into small pieces in 5 ml DMEM containing 10% bovine fetal serum (FACS buffer). Cell suspensions were grinded using 1-ml syringe cup on a 70-lm cell strainers (BD Falcon). Cells were washed with ice-cold PBS. Remaining red blood cells were lysed using ammonium chloride solution (Sigma). Cells were harvested and immersed 1 ml FACS buffer [PBS+2% FCS, 1 mM EDTA]. Lung cells were stained with antibodies against multiple surface antigens: PE-conjugated LEM 2/15 (anti-mouse MT1-MMP ab), PerCP/cy5.5-conjugated anti-mouse CD45 (clone—F11) or Pacific blue-anti-mouse CD45, APC-Cy7-conjugated EPCAM, APC-conjugated anti-CD11b, PerCP/cy5.5-anti-mouse Ly6C, FITC-anti-mouse Ly6G (clone 1A8), FITC-anti-mouse NKp46, FITC-anti-mouse-TCR-0. Flow cytometry was performed using FACSAriaIII Flow Cytometer (BD biosciences), and data was analyzed using FlowjoV 10.0.8 software. Sorted cells from non-infected control and infected mice treated with PBS were further subjected to RNA extraction, as previously mentioned in RNA extraction section, and were sequenced using RNA-Seq profiling and qPCR.

Example 1

Extra Cellular Matrix Genes are Induced During Influenza Infection

Figure 1A:
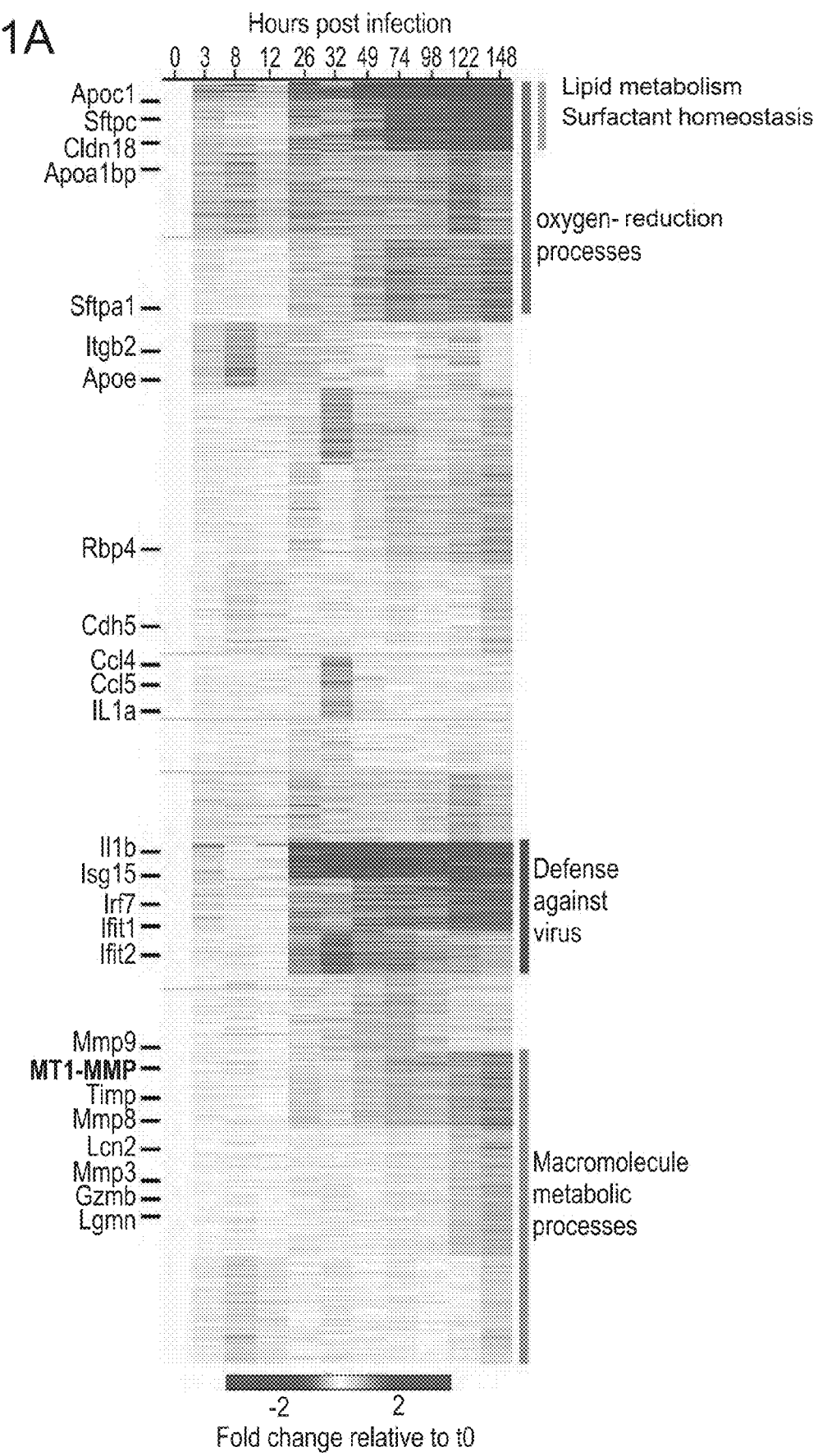

In order to systematically describe the effect of influenza inflection on host ECM circuits, genome-wide RNA-seq was used to measure the temporal transcriptional response of whole lung tissue during a seven-day course of influenza (Altboum et al., 2014). Gene expression was measured at ten time points following infection. C57BL/6 mice were infected by intranasal inoculation of mouse-adapted PR8 influenza A H1N1 virus using either lethal or sub-lethal dosages. PR8 infection is widely used as a influenza infection model (Morens et al., 2008; Tate et al., 2011; Taubenberger and Morens, 2006; Watanabe et al., 2013) consisting of rigorous alveolar spread, acute pulmonary hemorrhage and intensive host responses. Along with the disease progression, the symptoms and loss of body weight are initiated 24-48 hours post infection with an increase in viral load in the lungs (FIG. 6D). As expected, influenza infection resulted in induction of genes that are involved in inflammation chemotaxis (CXCL1, CXCL10, IIIb, IIIr), defense against viral infection (ISG15, IFNB1, IRF7, IFIT1 and IFIT3) and various chemokines (CCL2, CCL3, CCL4, CXCL2) as well as down-regulation of genes related to lung homeostasis (secretoglobins and relevant transcription factors (e.g. NKx2.1)) (FIG. 1A). Furthermore, many genes which were down-regulated following infection belong to oxygen-reduction processes, surfactant homeostasis (SFTPA1, SFTPC), cell-cell adhesion molecules such as integrins, cadherin, claudin (CLDN18, ITGB2, CDH5) and lipid metabolism (APOE, APOC1, APOA1BP). Additional genes that were statistically significantly up-regulated are set forth in Table 2B herein below.

TABLE 2B

| Symbols | Genes (mouse) |
|---|---|
| 1190002H23RIK | NM_025427 |
| 1500012F01RIK | NM_001081005 |
| 2010001M09RIK | NM_027222 |
| AA467197 | NM_001004174 |
| Acta1 | NM_009606 |
| Actb | NM_007393 |
| Adam15 | NM_001037722 |
| Adam8 | NM_007403 |
| Adamts15 | NM_001024139 |
| Adamts4 | NM_172845 |
| Aif1 | NM_019467 |
| Alpl | NM_007431 |
| Angptl4 | NM_020581 |
| Apod | NM_007470 |
| Apol6 | NM_028010 |
| Apol9a | NM_001162883 |
| Apol9b | NM_173743 |
| Arrb2 | NM_145429 |
| Atf3 | NM_007498 |
| AW112010 | NM_001177351 |
| B2m | NM_009735 |
| B4galt1 | NM_022305 |
| Bak1 | NM_007523 |
| Batf2 | NM_028967 |
| Bcl3 | NM_033601 |
| Bdkrb1 | NM_007539 |
| Bgn | NM_007542 |
| Bst2 | NM_198095 |
| C1qa | NM_007572 |
| C1qb | NM_009777 |
| C1qc | NM_007574 |
| C1qtnf6 | NM_028331 |
| C3ar1 | NM_009779 |
| Casp4 | NM_007609 |
| Ccl2 | NM_011333 |
| Ccl20 | NM_001159738 |
| Ccl4 | NM_013652 |
| Ccl5 | NM_013653 |
| Ccl7 | NM_013654 |
| Cd274 | NM_021893 |
| Cd300lf | NM_001169153 |
| Cd3d | NM_013487 |
| Cd72 | NM_001110322 |
| Cd8a | NM_009857 |
| Cd8b1 | NM_009858 |
| Cdca3 | NM_013538 |
| Cdkn1a | NM_007669 |
| Cebpd | NM_007679 |
| Cfb | NM_001142706 |
| Cidea | NM_007702 |
| Ckap4 | NM_175451 |
| Ckm | NM_007710 |
| Cldn4 | NM_009903 |
| Cmklr1 | NM_008153 |
| Cmpk2 | NM_020557 |
| Col1a1 | NM_007742 |
| Col1a2 | NM_007743 |
| Col3a1 | NM_009930 |
| Cox7a1 | NM_009944 |
| Cpxm1 | NM_019696 |
| Csrnp1 | NM_153287 |
| Ctgf | NM_010217 |
| Ctps | NM_016748 |
| Ctss | NM_021281 |
| Ctsz | NM_022325 |
| Cxcl1 | NM_008176 |
| Cxcl10 | NM_021274 |
| Cxcl12 | NM_021704 |
| Cxcl13 | NM_018866 |
| Cxcl16 | NM_023158 |
| Cxcl2 | NM_009140 |
| Cxcl5 | NM_009141 |
| Cxcl9 | NM_008599 |
| Cyp4f18 | NM_024444 |
| Cyr61 | NM_010516 |
| Daxx | NM_001199733 |
| Dbp | NM_016974 |
| Ddit4 | NM_029083 |

TABLE 2B-continued

| Symbols | Genes (mouse) |
| --- | --- |
| Ddx58 | NM_172689 |
| Dhx58 | NM_030150 |
| Dntt | NM_009345 |
| Dtx3l | NM_001013371 |
| Ecm1 | NM_007899 |
| Edem1 | NM_138677 |
| Eif2ak2 | NM_011163 |
| Eln | NM_007925 |
| Epha2 | NM_010139 |
| Enstil | NM_029495 |
| F3 | NM_010171 |
| Fam26f | NM_175449 |
| Fbn1 | NM_007993 |
| Fcer1g | NM_010185 |
| Fcgr1 | NM_010186 |
| Fcgr4 | NM_144559 |
| Fgfr1 | NM_001079908 |
| Fkbp5 | NM_010220 |
| Flnb | NM_134080 |
| Fn1 | NM_010233 |
| Fscn1 | NM_007984 |
| Fst | NM_008046 |
| Fxyd5 | NM_001111073 |
| Gadd45g | NM_011817 |
| Gbp10 | NM_001039646 |
| Gbp2 | NM_010260 |
| Gbp3 | NM_018734 |
| Gbp4 | NM_008620 |
| Gbp5 | NM_153564 |
| Gbp6 | NM_194336 |
| Gbp9 | NM_172777 |
| Glycam1 | NM_008134 |
| Gm12250 | NM_001135115 |
| Gm13889 | NM_001145034 |
| Gm14446 | NM_001101605 |
| Gm4841 | NM_001034859 |
| Gm4951 | NM_001033767 |
| Gpd1 | NM_010271 |
| Gpx3 | NM_008161 |
| Grn | NM_008175 |
| Gvin1 | NM_001039160 |
| Gzmb | NM_013542 |
| H2-Q7 | NM_010394 |
| H2-Q9 | NM_001201460 |
| H2-T10 | NM_010395 |
| H2-T22 | NM_010397 |
| H2-T23 | NM_010398 |
| H2-T9 | NM_010399 |
| Has1 | NM_008215 |
| Hcls1 | NM_008225 |
| Helz2 | NM_183162 |
| Hmga1 | NM_001166537 |
| Hmga1-rs1 | NM_001166477 |
| Hspa8 | NM_031165 |
| I830012O16Rik | NM_001005858 |
| Ier5 | NM_010500 |
| Ifi203 | NM_001045481 |
| Ifi204 | NM_008329 |
| Ifi205 | NM_172648 |
| Ifi2712a | NM_029803 |
| Ifi35 | NM_027320 |
| Ifi44 | NM_133871 |
| Ifi47 | NM_008330 |
| Ifih1 | NM_027835 |
| Ifit1 | NM_008331 |
| Ifit2 | NM_008332 |
| Ifit3 | NM_010501 |
| Ifitm3 | NM_025378 |
| Igtp | NM_018738 |
| Iigp1 | NM_001146275 |
| Il10ra | NM_008348 |
| Il18bp | NM_010531 |
| Il1b | NM_008361 |
| Il1rn | NM_001039701 |
| Il21r | NM_021887 |
| Irf1 | NM_001159396 |
| Irf5 | NM_012057 |
| Irf7 | NM_016850 |
| Irf8 | NM_008320 |
| Irg1 | NM_008392 |
| Irgm1 | NM_008326 |
| Irgm2 | NM_019440 |
| Isg15 | NM_015783 |
| Isg20 | NM_020583 |
| Itga5 | NM_010577 |
| Junb | NM_008416 |
| Kcnn4 | NM_001163510 |
| Krt13 | NM_010662 |
| Krt4 | NM_008475 |
| Laptm5 | NM_010686 |
| Lars2 | NM_153168 |
| Lck | NM_001162433 |
| Lcn2 | NM_008491 |
| Lgals3bp | NM_011150 |
| Lgals9 | NM_001159301 |
| Lgmn | NM_011175 |
| Lilrb4 | NM_013532 |
| Lox | NM_010728 |
| Loxl1 | NM_010729 |
| Loxl2 | NM_033325 |
| Loxl3 | NM_013586 |
| Ly6a | NM_010738 |
| Ly6c1 | NM_010741 |
| Ly6c2 | NM_001099217 |
| Ly6i | NM_020498 |
| Lyve1 | NM_053247 |
| Mmp14 | NM_008608 |
| Mmp3 | NM_010809 |
| Mmp8 | NM_008611 |
| Mnda | NM_001033450 |
| Mndal | NM_001170853 |
| Mpeg1 | NM_010821 |
| Ms4a4b | NM_021718 |
| Ms4a4c | NM_029499 |
| Ms4a6b | NM_027209 |
| Ms4a6c | NM_028595 |
| Ms4a6d | NM_026835 |
| Mt1 | NM_013602 |
| Mt2 | NM_008630 |
| Mx1 | NM_010846 |
| Mx2 | NR_003508 |
| Mxd1 | NM_010751 |
| Myh1 | NM_030679 |
| Myh8 | NM_177369 |
| Mylpf | NM_016754 |
| Nampt | NM_021524 |
| Nfkbia | NM_010907 |
| Nlrc5 | NM_001033207 |
| Nppa | NM_008725 |
| Nt5c3 | NM_026004 |
| Oas1a | NM_145211 |
| Oas1g | NM_011852 |
| Oas2 | NM_145227 |
| Oasl1 | NM_145209 |
| Oasl2 | NM_011854 |
| Ogfr | NM_031373 |
| Parp12 | NM_172893 |
| Parp14 | NM_001039530 |
| Parp9 | NM_030253 |
| Per1 | NM_001159367 |
| Pfkfb3 | NM_001177757 |
| Phf11b | NM_001164327 |
| Phf11d | NM_199015 |
| Pirb | NM_011095 |
| Pla2g7 | NM_013737 |
| Plac8 | NM_139198 |
| Plat | NM_008872 |
| Plau | NM_008873 |
| Pld4 | NM_178911 |
| Pnp | NM_013632 |
| Pnp2 | NM_001123371 |
| Pou2af1 | NM_011136 |
| Ppa1 | NM_026438 |
| Prmt1 | NM_019830 |
| Prss22 | NM_133731 |
| Psmb10 | NM_013640 |

TABLE 2B-continued

| Symbols | Genes (mouse) |
|---|---|
| Psmb8 | NM_010724 |
| Psme2 | NM_011190 |
| Pstpip1 | NM_011193 |
| Ptafr | NM_001081211 |
| Ptk7 | NM_175168 |
| Ptx3 | NM_008987 |
| Pycard | NM_023258 |
| Pyhin1 | NM_175026 |
| Qsox1 | NM_001024945 |
| Relb | NM_009046 |
| Retnla | NM_020509 |
| Rhox8 | NM_001004193 |
| Rpsa | NM_011029 |
| Rsad2 | NM_021384 |
| Rtp4 | NM_023386 |
| S100a14 | NM_001163526 |
| S100a4 | NM_011311 |
| S100a6 | NM_011313 |
| S100a8 | NM_013650 |
| S100a9 | NM_009114 |
| Saa1 | NM_009117 |
| Saa3 | NM_011315 |
| Samd9l | NM_010156 |
| Samhd1 | NM_001139520 |
| Sbno2 | NM_183426 |
| Sdc3 | NM_011520 |
| Sell | NM_001164059 |
| Sema7a | NM_011352 |
| Serinc3 | NM_012032 |
| Serpina3f | NM_001033335 |
| Serpina3g | NM_009251 |
| Serpina3m | NM_009253 |
| Serpina3n | NM_009252 |
| Serpine1 | NM_008871 |
| Serping1 | NM_009776 |
| Sfn | NM_018754 |
| Sh3pxd2b | NM_177364 |
| Slc15a3 | NM_023044 |
| Slc25a37 | NM_026331 |
| Slc7a5 | NM_011404 |
| Slfn1 | NM_011407 |
| Slfn2 | NM_011408 |
| Slfn4 | NM_011410 |
| Slfn5 | NM_183201 |
| Slfn8 | NM_001167743 |
| Slfn9 | NM_172796 |
| Snx32 | NM_001024560 |
| Socs1 | NM_009896 |
| Socs3 | NM_007707 |
| Sparcl1 | NM_010097 |
| Sphk1 | NM_011451 |
| Spp1 | NM_009263 |
| Sprr1a | NM_009264 |
| Stat1 | NM_009283 |
| Stat2 | NM_019963 |
| Tap1 | NM_013683 |
| Tap2 | NM_011530 |
| Tapbp | NM_001025313 |
| Tcf7 | NM_009331 |
| Tgfbi | NM_009369 |
| Tgm2 | NM_009373 |
| Tgtp1 | NM_011579 |
| Tgtp2 | NM_001145164 |
| Thbs1 | NM_011580 |
| Themis2 | NM_001033308 |
| Thrsp | NM_009381 |
| Thy1 | NM_009382 |
| Timp1 | NM_001044384 |
| Tinagl1 | NM_001168333 |
| Tnc | NM_011607 |
| Tnfaip2 | NM_009396 |
| Tnfrsf12a | NM_013749 |
| Tnni2 | NM_009405 |
| Tor3a | NM_023141 |
| Tpm2 | NM_009416 |
| Trafd1 | NM_172275 |
| Trex1 | NM_011637 |
| Trib1 | NM_144549 |
| Trim25 | NM_009546 |
| Trim30a | NM_009099 |
| Tuba1c | NM_009448 |
| Tubb5 | NM_011655 |
| Tubb6 | NM_026473 |
| Ubc | NM_019639 |
| Ucp1 | NM_009463 |
| Usp18 | NM_011909 |
| Vcan | NM_001134475 |
| Wars | NM_001164488 |
| Xaf1 | NM_001037713 |
| Xdh | NM_011723 |
| Zbp1 | NM_021394 |
| Znfx1 | NM_001033196 |

Figure 6A:
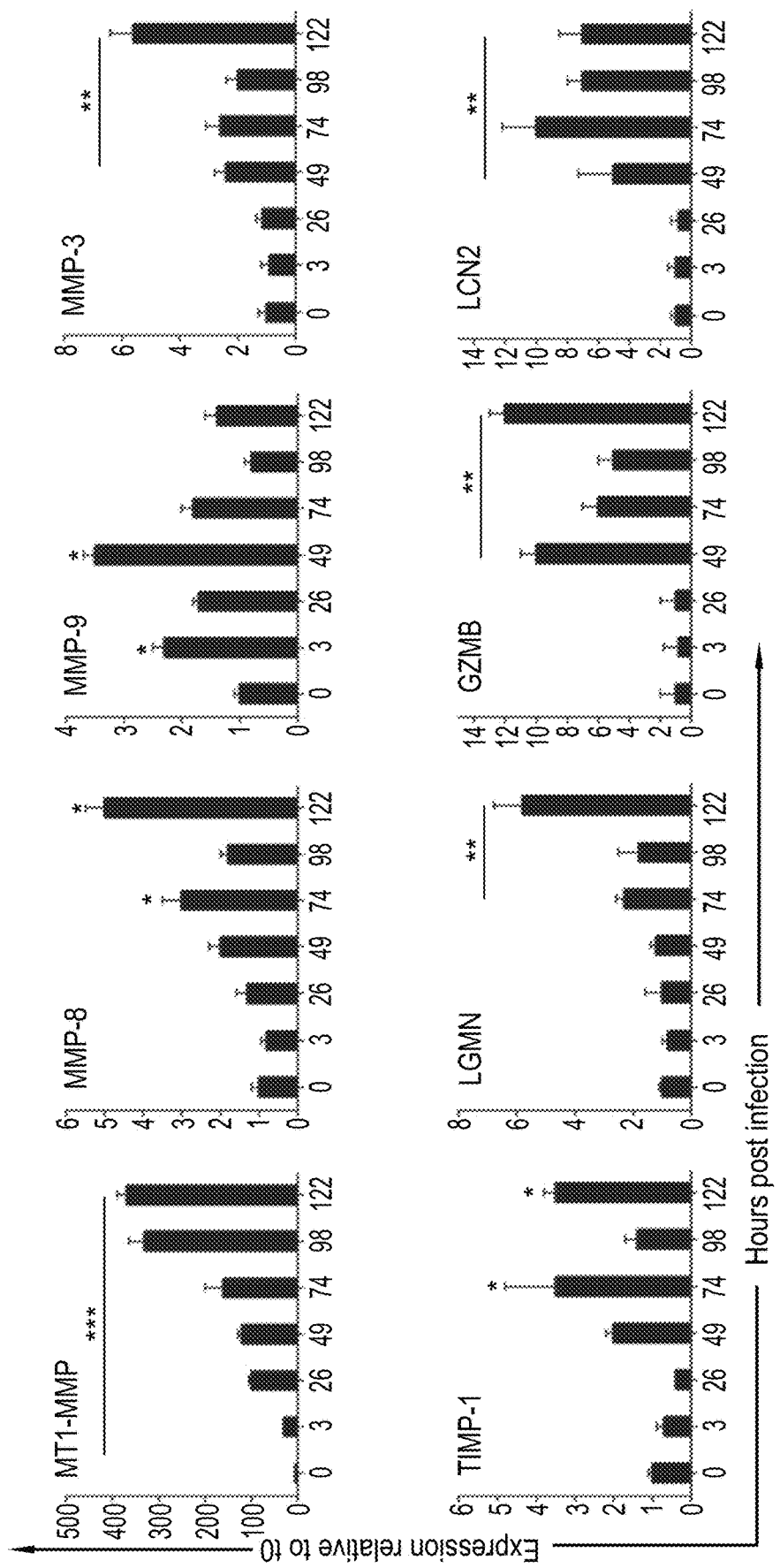

Of special notice was a large group of genes involved in ECM remodeling including macromolecule metabolism and protease synthesis (FIG. 1A). Remarkably, this group of genes was highly over-represented throughout infection, exhibiting a wide panel of pathways involved in multiple ECM remodeling events (FIG. 1A-C). An enrichment of functional categories relating to extra cellular modulators involved in proteolysis, collagen remodeling and catabolism, fibrinolysis, wound healing, homeostasis and cell migration ($p \leq 10^{-4}$) was uncovered, peaking 74 hours post infection (FIG. 1B). All together, 479 out of 3530 differentially expressed genes (13.6%) are related to ECM remodeling. These included serine proteases, lysyl oxidases, cathepsins, disintegrins (ADAMs), metalloproteinases (MMPs) and their natural inhibitors (TIMPs), which serve as ECM modifiers that determine the turnover of different ECM components. Within this group of genes, robust induction of MT1-MMP at both the RNA (400 fold change; FIG. 1D) and protein levels 48 hours post infection (FIG. 6A-B) was found. Using quantitative real time PCR, the temporal changes in MT1-MMP expression was corroborated as well as other representative genes belonging to the MMP family (MMP-3, 8 and 9) and modulating the ECM (FIG. 6A, B, C).

Example 2

MT1-MMP Expression is Induced in Myeloid Cells Post Influenza Infection

Figure 7A:
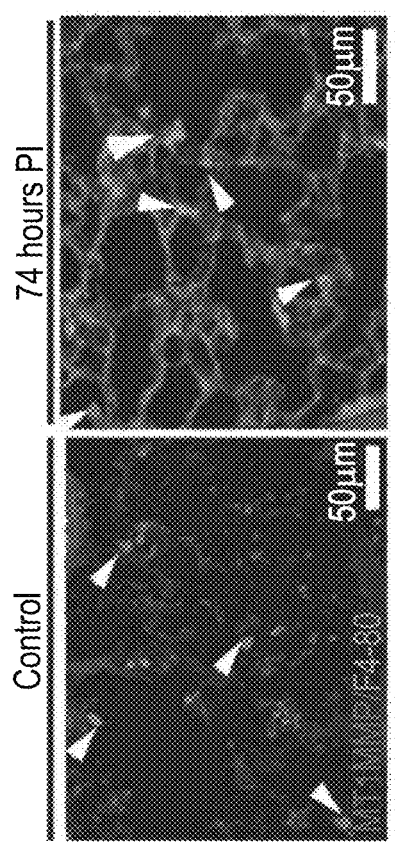
Figure 7B:
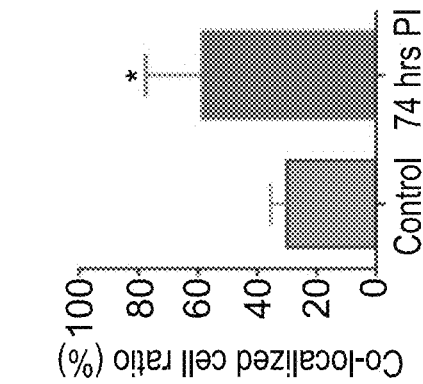
Figure 7C:
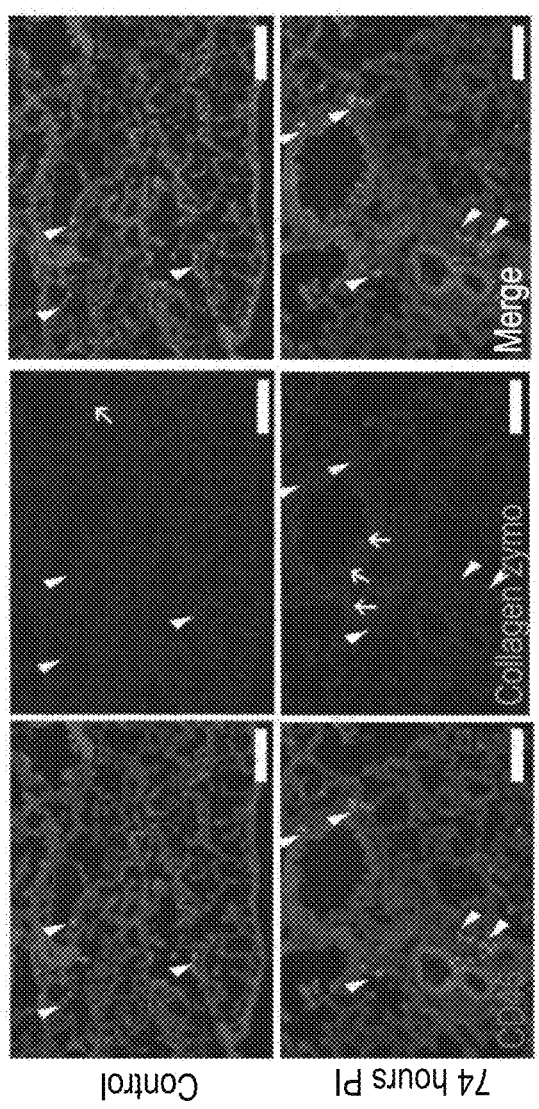
Figure 7D:
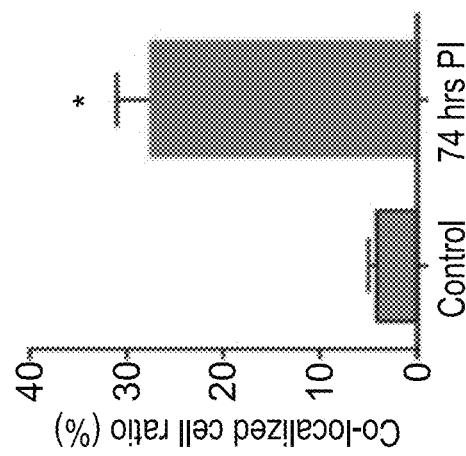

In order to identify the cell population acting as the source of MT1-MMP during infection course by flow cytometry was performed. Of the population of cells expressing MT1-MMP in the non-infected lung, the overwhelming majority was non-hematopoietic cell population (CD45$^-$, 89.5%), while only 10.5% were of hematopoietic origin (CD45$^+$) (FIG. 2A). Post infection, the CD45$^+$ MT1-MMP expressing population increased four-fold (40.9%). Specifically, the CD11b$^+$, MT1-MMP$^+$ portion of the immune cells increased from 32.9% to 64.9%, while the non-hematopoietic (CD45$^-$) MT1-MMP-expressing cells decreased by two-fold (FIG. 2A). Histogram plots (FIG. 2B) further show that the overall increase in MT1-MMP expression post infection (FIG. 2B) can be associated with increased expression of MT1-MMP in CD11b+ cells (FIG. 2B), rather than lung epithelial cells, in which MT1-MMP was reduced post infection (FIG. 2B). MT1-MMP expression in CD45$^+$ versus CD45$^-$ sorted populations before and during infection was further validated at the RNA level using qPCR (FIG. 2C). Immunostaining for MT1-MMP as well as F4/80 markers in influenza-infected lungs confirm our observation that MT1-MMP expressing cells largely co-localize with F4/80 positive cells at 74 hours post infection. Since macrophages are both CD11b⁺ and F4/80+ immune cells, these findings suggest that macrophages are a significant source of MT1-MMP following infection (FIG. 7A arrow heads, 7B). In order to monitor the collagenase activity of influenza-infected lungs, in situ zymography was used. It was found that following infection, collagenolytic activity is mostly associated with CD45⁺ cells, as well as CD45⁻ cells lining the bronchi of infected lungs (FIG. 7C arrows, D).

In order to further characterize the MT1-MMP-expressing populations before and after (74 hours) infection, RNA-seq analysis was performed on sorted MT1-MMP-expressing CD45⁺ and CD45⁻ subpopulations. In total, 2169 genes were found to be differentially expressed in cells post-infection as compared to un-infected cells in both CD45⁺ and CD45⁻ populations (FIG. 8). Consistent with the analysis from whole lung RNA-seq, an increase in activation of inflammatory signaling pathways and cytokine production in both immune (CD45⁺) and stromal (CD45⁻) cells expressing MT1-MMP following infection was observed (FIG. 8). The immune cells, in particular, exhibited significant up-regulation of cytokines (CCL2, CCL3, CCL4, CXCL2, IL1b) and anti-viral response genes (e.g. SLFN4, IFIT1 and IFIT2), while the stromal cells exhibited down-regulation of genes associated with lung homeostatic functions such as surfactant production (e.g. SFTPB, SFTPC). The immune population showed increase in expression of monocyte/macrophage/DC markers (e.g. CD11b) and decrease of multiple B cell markers (e.g. CD19, CD37, CD79). Thus, MT1-MMP expression post-infection is associated with activated immune cells from the myeloid compartment (FIG. 8).

Example 3

Influenza Infection Induces Destruction of ECM Morphology and Composition

MT1-MMP plays a major role in cancer-associated invasion processes through degradation of fibrillar collagen, laminin and other ECM components. To evaluate the functional role of MT1-MMP in influenza infection, mass spectrometry analysis (FIG. 3A) as well as scanning electron microscopy (SEM) imaging of lung tissues devoid of its cellular compartment (de-cellularized) before and after infection was performed (FIGS. 9A-B). SEM analysis of influenza-infected lungs showed massive distortion of ECM morphology (FIG. 3B-C) as well as rearrangement of collagen fibers, specifically in the alveolar walls. At 74 hours post-infection, collagen bundles on the boundaries of alveolar sacs displayed unraveled fiber ends and dispersed orientation angles (FIG. 3B). This was further confirmed by measuring the orientation of the fibrils composing the alveolar walls (FIG. 3C). In addition, the alveolar space and septa were distorted in the infected lungs (FIG. 3B). To validate these results and further analyze the integrity of the whole tissue—including the cells and ECM in their native environment—during infection, a novel form of electron microscopy imaging, AirSEM (Solomonov et al., 2014) was used. AirSEM enables visualization of native hydrated tissues in ambient conditions, thus avoiding potential artifacts associated with sample preparation for SEM. Imaging of virally-infected lung tissues exhibited tissue destruction characterized by both alveolar and bronchial cell depletion as well as distortion of alveolar sacs and ducts followed by alveolar wall thinning (FIG. 9A-B). Finally, AirSEM imaging of fresh lung ECM scaffolds (de-cellularized tissues) showed similar alveolar collagen degradation and distortion patterns as observed in conventional SEM analysis (FIG. 9A-B).

Example 4

Figure 3A:
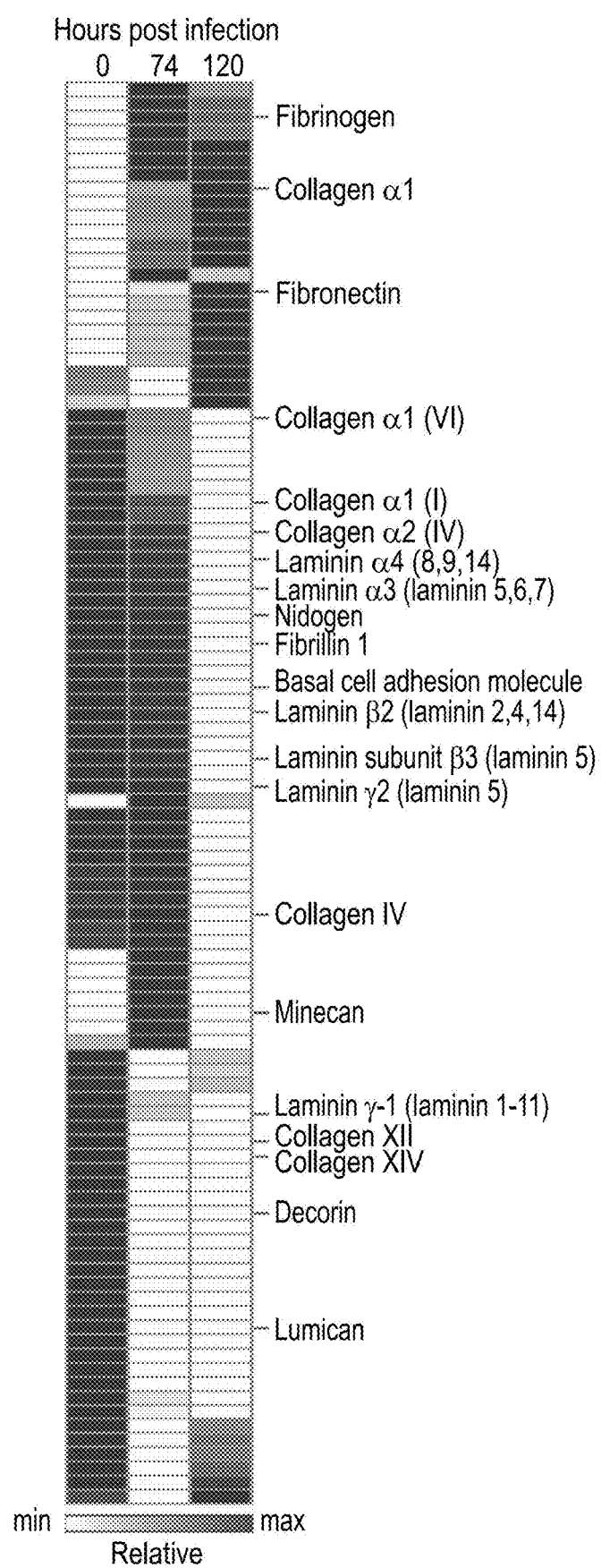
Figure 3B:
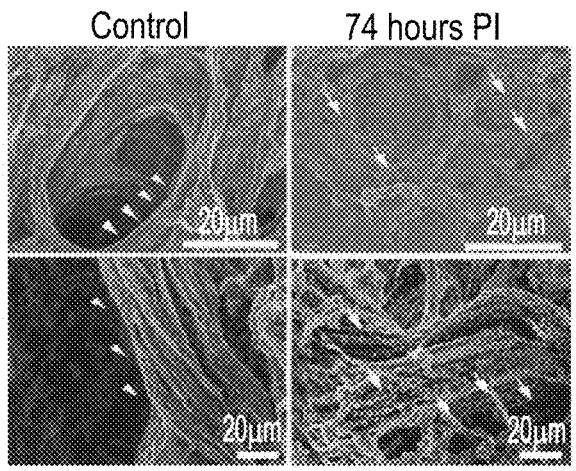
Figure 3C:
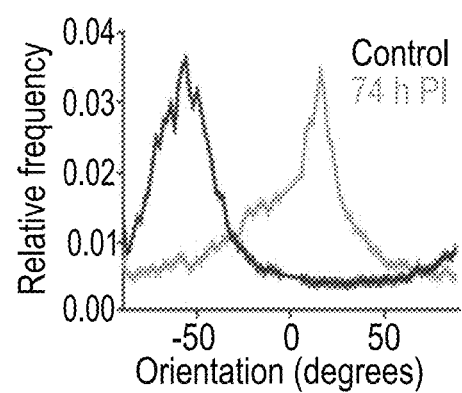
Figure 3D:
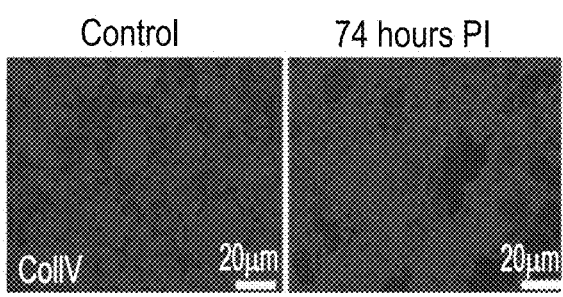
Figure 3E:
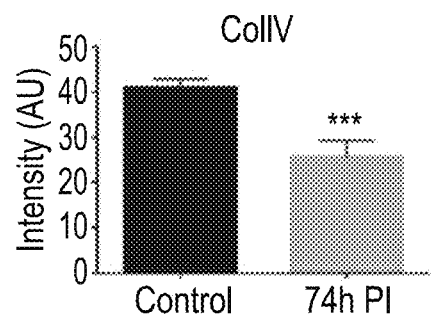
Figure 3F:
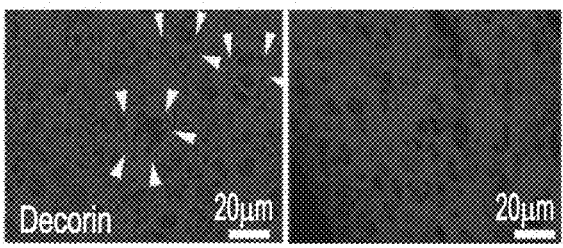
Figure 3G:
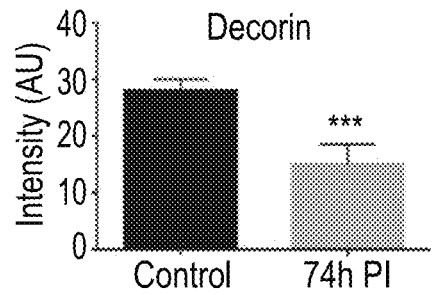
Figure 3H:
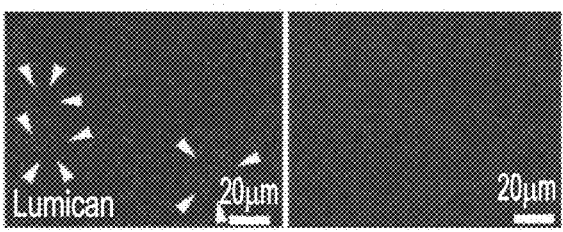
Figure 3I:
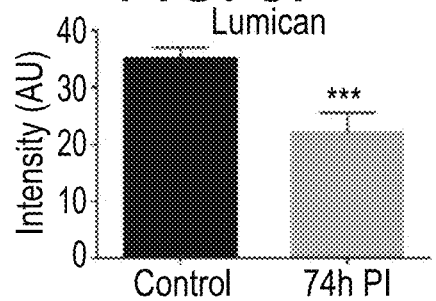

Global Proteomics Analysis Identifies Degradation of ECM Scaffolds During Influenza Infection In order to globally examine the proteolytic implications on ECM remodeling during influenza infection, a tandem mass spectrometry (LC-MS-MS) approach was used (FIG. 3A, Table 3, herein below). Analysis of the de-cellularized lung tissue 74 and 120 hours post infection compared with non-infected tissue showed compositional changes that could be connected to structural changes observed in the architecture of collagen fibrils lining the alveolar wall (FIG. 3B-C). Specifically, the proteomic data analysis of the influenza-infected lungs identified modifications in the molecular composition of the ECM, including gradual depletion of collagen and subtypes of laminin molecules (FIG. 3A). In addition, multiple basement-membrane-associated components as well as basal-cell-adhesion molecules (e.g. Nidogen, Decorin, Collagen types IV, XII, XIV and Fibrillin; FIG. 3A) were depleted from infected lung tissue indicating massive transformation of ECM integrity and molecular composition. The loss of representative ECM molecules (Collagen IV, Decorin and Lumican) was confirmed by staining the ECM scaffolds of infected and non-infected lungs (FIG. 3D-I). Importantly, several of the components depleted during infection, such as type I collagen, laminin nidogen, lumican, mimecan, fibrillin and decorin, are known MT1-MMP-substrates (Koziol et al., 2012; McQuibban et al., 2000; Noel et al., 2012; Overall, 2002; Shimizu-Hirota et al., 2012; Stegemann et al., 2013). Since multiple MT1-MMP substrates are degraded during the course of influenza infection, it was hypothesized that lung ECM proteolysis and host mortality can be protected by specifically blocking the collagenase activity of MT1-MMP.

TABLE 3

| Protein annotation | Normalized control | Normalized T72 | Normalized T120 |
|---|---|---|---|
| ADP/ATP translocase 1 OS = Mus musculus GN = Slc25a4 PE = 1 SV = 4 – [ADT1_MOUSE] | 6.153575947 | 5.977276302 | 0 |
| ADP/ATP translocase 2 OS = Mus musculus GN = Slc25a5 PE = 1 SV = 3 – [ADT2_MOUSE] | 6.223198168 | 5.887684499 | 0 |
| Advanced glycosylation end product-specific receptor OS = Mus musculus GN = Ager PE = 2 SV = 1 – [C5H3H4_MOUSE] | 6.473725601 | 0 | 0 |
| Agrin OS = Mus musculus GN = Agrn PE = 4 SV = 1 – [M0QWP1_MOUSE] | 6.308175158 | 6.593093331 | 6.511599322 |
| Apha-amylase 1 OS = Mus musculus GN = Amy1 PE = 1 SV = 2 – [AMY1_MOUSE] | 0 | 5.65986227 | 7.460711241 |

TABLE 3-continued

| Protein annotation | Normalized control | Normalized T72 | Normalized T120 |
|---|---|---|---|
| Annexin A1 OS = *Mus musculus* GN = Anxa1 PE = 1 SV = 2 – [ANXA1_MOUSE] | 0 | 5.824702042 | 0 |
| Annexin A2 (Fragment) OS = *Mus musculus* GN = Anxa2 PE = 2 SV = 1 – [BOV2N8_MOUSE] | 5.679465046 | 5.957616046 | 6.195405289 |
| Aquaporin-5 OS = *Mus musculus* GN = Aqp5 PE = 2 SV = 1 – [AQP5_MOUSE] | 6.162716299 | 5.961971735 | 0 |
| Basal cell adhesion molecule OS = *Mus musculus* GN = Bcam PE = 2 SV = 1 – [BCAM_MOUSE] | 6.227912096 | 5.999952109 | 0 |
| Basement membrane-specific heparan sulfate proteoglycan core protein OS = *Mus musculus* GN = Hspg2 PE = 2 SV = 1 – [E9PZ16_MOUSE] | 7.415377503 | 7.322287706 | 7.230770907 |
| Beta-actin-like protein 2 OS = *Mus musculus* GN = Actbl2 PE = 1 SV = 1 – [ACTBL_MOUSE] | 6.386138757 | 6.785714287 | 7.052084571 |
| Beta-globin OS = *Mus musculus* GN = Hbb-b1 PE = 2 SV = 1 – [A8DUK4_MOUSE] | 6.447007246 | 6.964298502 | 6.938126292 |
| Carboxylesterase 1D OS = *Mus musculus* GN = Ces1d PE = 1 SV = 1 – [CES1D_MOUSE] | 5.527869285 | 5.634653635 | 0 |
| Caveolin (Fragment) OS = *Mus musculus* GN = Cav1 PE = 2 SV = 2 – [D3Z148_MOUSE] | 6.495955194 | 6.212414678 | 0 |
| Chitinase-3-like protein 4 OS = *Mus musculus* GN = Chi3l4 PE = 1 SV = 2 – [CH3L4_MOUSE] | 5.78250122 | 0 | 0 |
| Collagen alpha-1(I) chain OS = *Mus musculus* GN = Col1a1 PE = 1 SV = 4 – [CO1A1_MOUSE] | 7.075805627 | 7.028473097 | 6.753210524 |
| Collagen alpha-1(III) chain OS = *Mus musculus* GN = Col3a1 PE = 2 SV = 4 – [CO3A1_MOUSE] | 6.934207535 | 7.060366511 | 7.23163175 |
| Collagen alpha-1(IV) chain OS = *Mus musculus* GN = Col4a1 PE = 2 SV = 4 – [CO4A1_MOUSE] | 7.695020525 | 7.694567589 | 7.536290851 |
| Collagen alpha-1(VI) chain OS = *Mus musculus* GN = Col6a1 PE = 2 SV = 1 – [CO6A1_MOUSE] | 6.86809465 | 6.551279889 | 6.15880609 |
| Collagen alpha-1(XII) chain OS = *Mus musculus* GN = Col12a1 PE = 4 SV = 1 – [J3KMS9_MOUSE] | 5.714611383 | 0 | 0 |
| Collagen alpha-1(XIV) chain OS = *Mus musculus* GN = Col14a1 PE = 2 SV = 1 – [B7ZNH7_MOUSE] | 6.125016434 | 0 | 0 |
| Collagen alpha-2(I) chain OS = *Mus musculus* GN = Col1a2 PE = 2 SV = 2 – [CO1A2_MOUSE] | 6.543280973 | 6.813995104 | 7.023591569 |
| Collagen alpha-2(IV) chain OS = *Mus musculus* GN = Col4a2 PE = 2 SV = 4 – [CO4A2_MOUSE] | 7.550827668 | 7.530963433 | 7.332686213 |
| Collagen alpha-2(VI) chain OS = *Mus musculus* GN = Col6a2 PE = 2 SV = 3 – [CO6A2_MOUSE] | 6.947369979 | 6.792465562 | 6.635688357 |
| Collagen alpha-3(IV) chain OS = *Mus musculus* GN = Col4a3 PE = 1 SV = 2 – [CO4A3_MOUSE] | 7.21593568 | 7.650127224 | 7.416342179 |
| Collagenase 3 OS = *Mus musculus* GN = Mmp13 PE = 1 SV = 1 – [MMP13_MOUSE] | 7.72568074 | 7.15902446 | 7.286304725 |
| Decorin OS = *Mus musculus* GN = Dcn PE = 2 SV = 1 – [PGS2_MOUSE] | 6.22520272 | 0 | 0 |
| Desmoglein-1-alpha OS = *Mus musculus* GN = Dsg1a PE = 2 SV = 2 – [DSG1A_MOUSE] | 5.548747085 | 5.852724683 | 6.62085048 |
| Desmoplakin OS = *Mus musculus* GN = Dsp PE = 2 SV = 1 – [DESP_MOUSE] | 6.162304582 | 6.382926331 | 6.992943381 |
| Dimethylaniline monooxygenase [N-oxide-forming] 2 OS = *Mus musculus* GN = Fmo2 PE = 1 SV = 3 – [FMO2_MOUSE] | 5.714661158 | 5.311917766 | 0 |
| Elongation factor 1-alpha 1 OS = *Mus musculus* GN = Eef1a1 PE = 1 SV = 3 – [EF1A1_MOUSE] | 5.598955869 | 5.764182366 | 0 |
| EMILIN-1 OS = *Mus musculus* GN = Emilin1 PE = 1 SV = 1 – [EMIL1_MOUSE] | 0 | 0 | 6.392836508 |
| Fibrillin-1 OS = *Mus musculus* GN = Fbn1 PE = 4 SV = 1 – [A2AQ53_MOUSE] | 5.877764759 | 5.704777353 | 0 |
| Fibrinogen beta chain OS = *Mus musculus* GN = Fgb PE = 2 SV = 1 – [FIBB_MOUSE] | 5.858490424 | 6.687289698 | 0 |
| Fibrinogen gamma chain OS = *Mus musculus* GN = Fgg PE = 2 SV = 1 – [FIBG_MOUSE] | 5.83914522 | 7.040881119 | 6.623714799 |
| Fibrinogen, alpha polypeptide OS = *Mus musculus* GN = Fga PE = 2 SV = 1 – [Q99K47_MOUSE] | 6.056325883 | 7.261485562 | 6.90940505 |
| Fibronectin OS = *Mus musculus* GN = Fn1 PE = 1 SV = 4 – [FINC_MOUSE] | 6.818688119 | 6.880740949 | 7.353539538 |
| Filamin, alpha (Fragment) OS = *Mus musculus* GN = Flna PE = 4 SV = 1 – [B7FAV1_MOUSE] | 7.008505708 | 6.628436178 | 6.827984047 |
| Gelsolin OS = *Mus musculus* GN = Gsn PE = 1 SV = 3 – [GELS_MOUSE] | 5.729356743 | 5.763326472 | 0 |
| Haptoglobin OS = *Mus musculus* GN = Hp PE = 1 SV = 1 – [HPT_MOUSE] | 0 | 6.109791413 | 0 |
| Hemoglobin subunit alpha OS = *Mus musculus* GN = Hba PE = 1 SV = 2 – [HBA_MOUSE] | 0 | 6.10790139 | 6.398904972 |
| Hemopexin OS = *Mus musculus* GN = Hpx PE = 1 SV = 2 – [HEMO_MOUSE] | 0 | 6.010280907 | 0 |

TABLE 3-continued

| Protein annotation | Normalized control | Normalized T72 | Normalized T120 |
|---|---|---|---|
| Histone H2A OS = *Mus musculus* GN = Hist1h2al PE = 2 SV = 1 – [F8WIX8_MOUSE] | 7.392138835 | 6.917080096 | 7.013660548 |
| Histone H2A type 1-H OS = *Mus musculus* GN = Hist1h2ah PE = 1 SV = 3 – [H2A1H_MOUSE] | 7.392138835 | 6.926879953 | 6.857002872 |
| Histone H2B type 1-F/J/L OS = *Mus musculus* GN = Hist1h2bf PE = 1 SV = 2 – [H2B1F_MOUSE] | 7.491390907 | 7.124577253 | 7.005403699 |
| Histone H3 (Fragment) OS = *Mus musculus* GN = H3f3a PE = 2 SV = 1 – [E0CZ27_MOUSE] | 7.101484514 | 6.959792034 | 7.049922513 |
| Histone H4 OS = *Mus musculus* GN = Hist1h4a PE = 1 SV = 2 – [H4_MOUSE] | 7.676125661 | 7.580781002 | 7.458167442 |
| Ig gamma-1 chain C region secreted form OS = *Mus musculus* GN = Ighg1 PE = 1 SV = 1 – [IGHG1_MOUSE] | 5.961455553 | 0 | 0 |
| Ig kappa chain V-II region 26-10 OS = *Mus musculus* PE = 1 SV = 1 – [KV2A7_MOUSE] | 6.419014568 | 5.836803643 | 0 |
| Ig mu chain C region secreted form OS = *Mus musculus* GN = Igh-6 PE = 1 SV = 2 – [IGHM_MOUSE] | 6.201286175 | 6.434377902 | 6.526314192 |
| Indolethylamine N-methyltransferase OS = *Mus musculus* GN = Inmt PE = 1 SV = 1 – [INMT_MOUSE] | 5.637864703 | 0 | 0 |
| Junction plakoglobin OS = *Mus musculus* GN = Jup PE = 1 SV = 3 – [PLAK_MOUSE] | 6.264791243 | 6.465410008 | 7.017601329 |
| Lactotransferrin OS = *Mus musculus* GN = Ltf PE = 2 SV = 4 – [TRFL_MOUSE] | 0 | 5.762688986 | 0 |
| Laminin subunit alpha-2 OS = *Mus musculus* GN = Lama2 PE = 2 SV = 1 – [F8VQ43_MOUSE] | 5.937766596 | 0 | 0 |
| Laminin subunit alpha-3 OS = *Mus musculus* GN = Lama3 PE = 4 SV = 1 – [E9PUR4_MOUSE] | 6.674990286 | 6.260528414 | 0 |
| Laminin subunit alpha-4 OS = *Mus musculus* GN = Lama4 PE = 1 SV = 2 – [LAMA4_MOUSE] | 6.511385176 | 6.099945813 | 0 |
| Laminin subunit alpha-5 OS = *Mus musculus* GN = Lama5 PE = 1 SV = 4 – [LAMA5_MOUSE] | 6.607315399 | 6.547091642 | 6.327053775 |
| Laminin subunit beta-1 OS = *Mus musculus* GN = Lamb1 PE = 1 SV = 3 – [LAMB1_MOUSE] | 5.951335808 | 0 | 0 |
| Laminin subunit beta-2 OS = *Mus musculus* GN = Lamb2 PE = 2 SV = 2 – [LAMB2_MOUSE] | 6.610256604 | 6.263976054 | 0 |
| Laminin subunit beta-3 OS = *Mus musculus* GN = Lamb3 PE = 2 SV = 2 – [LAMB3_MOUSE] | 6.687215625 | 6.379447773 | 0 |
| Laminin subunit gamma-1 OS = *Mus musculus* GN = Lamc1 PE = 2 SV = 1 – [F8VQJ3_MOUSE] | 6.70043806 | 6.209442052 | 6.048843786 |
| Laminin subunit gamma-2 OS = *Mus musculus* GN = Lamc2 PE = 4 SV = 1 – [G5E874_MOUSE] | 6.218905096 | 6.142010192 | 0 |
| Lumican OS = *Mus musculus* GN = Lum PE = 1 SV = 2 – [LUM_MOUSE] | 6.189723414 | 0 | 0 |
| Lysozyme C-2 OS = *Mus musculus* GN = Lyz2 PE = 1 SV = 2 – [LYZ2_MOUSE] | 5.83391544 | 6.30672877 | 0 |
| MCG1050941 OS = *Mus musculus* GN = Gm5414 PE = 2 SV = 1 – [Q6IFZ8_MOUSE] | 6.899619386 | 7.13581107 | 7.369324207 |
| MCG16555 OS = *Mus musculus* GN = Vdac3-ps1 PE = 4 SV = 1 – [J3QPE8_MOUSE] | 5.516224232 | 0 | 0 |
| Microfibril-associated glycoprotein 4 OS = *Mus musculus* GN = Mfap4 PE = 1 SV = 1 – [MFAP4_MOUSE] | 6.342904739 | 6.43463342 | 0 |
| Mimecan OS = *Mus musculus* GN = Ogn PE = 2 SV = 1 – [MIME_MOUSE] | 0 | 5.701058917 | 0 |
| Myelin proteolipid protein OS = *Mus musculus* GN = Plp1 PE = 1 SV = 2 – [MYPR_MOUSE] | 6.987098666 | 6.432634236 | 6.586369313 |
| Myeloid bactenecin (F1) OS = *Mus musculus* GN = Ngp PE = 2 SV = 1 – [O08692_MOUSE] | 5.44115199 | 6.142101018 | 0 |
| Myeloperoxidase OS = *Mus musculus* GN = Mpo PE = 2 SV = 2 – [PERM_MOUSE] | 0 | 6.382761391 | 0 |
| Myosin-10 OS = *Mus musculus* GN = Myh10 PE = 1 SV = 2 – [MYH10_MOUSE] | 6.107244043 | 0 | 0 |
| Myosin-11 OS = *Mus musculus* GN = Myh11 PE = 4 SV = 1 – [E9QPE7_MOUSE] | 6.549138497 | 6.023621662 | 6.486852262 |
| Myosin-9 OS = *Mus musculus* GN = Myh9 PE = 1 SV = 4 – [MYH9_MOUSE] | 6.534077311 | 5.875775823 | 6.34610934 |
| Neurofilament heavy polypeptide OS = *Mus musculus* GN = Nefh PE = 1 SV = 3 – [NFH_MOUSE] | 6.138902554 | 6.97864523 | 6.975120413 |
| Nidogen-1 OS = *Mus musculus* GN = Nid1 PE = 1 SV = 2 – [NID1_MOUSE] | 7.128370461 | 7.113290014 | 6.730533502 |
| Nidogen-2 OS = *Mus musculus* GN = Nid2 PE = 1 SV = 2 – [NID2_MOUSE] | 6.241408448 | 5.983593362 | 0 |
| Peptidyl-prolyl cis–trans isomerase B OS = *Mus musculus* GN = Ppib PE = 2 SV = 2 – [PPIB_MOUSE] | 6.012874469 | 0 | 0 |
| Periostin OS = *Mus musculus* GN = Postn PE = 1 SV = 2 – [POSTN_MOUSE] | 6.725725241 | 6.251665549 | 6.20505634 |
| Peroxiredoxin-1 (Fragment) OS = *Mus musculus* GN = Prdx1 PE = 2 SV = 1 – [B1AXW5_MOUSE] | 5.981037111 | 5.753060397 | 6.142601977 |

TABLE 3-continued

| Protein annotation | Normalized control | Normalized T72 | Normalized T120 |
|---|---|---|---|
| Phosphate carrier protein, mitochondrial OS = Mus musculus GN = Slc25a3 PE = 1 SV = 1 – [MPCP_MOUSE] | 5.91683531 | 0 | 0 |
| Platelet glycoprotein 4 OS = Mus musculus GN = Cd36 PE = 1 SV = 2 – [CD36_MOUSE] | 6.16384265 | 5.950272926 | 0 |
| Polyubiquitin-C (Fragment) OS = Mus musculus GN = Ubc PE = 2 SV = 1 – [E9Q5F6_MOUSE] | 6.968911307 | 6.84889605 | 6.756181153 |
| Prelamin-A/C OS = Mus musculus GN = Lmna PE = 1 SV = 2 – [LMNA_MOUSE] | 5.749092722 | 0 | 0 |
| Protein 4732456N10Rik OS = Mus musculus GN = 4732456N10Rik PE = 3 SV = 1 – [E9Q1Z0_MOUSE] | 7.2526558 | 7.399852941 | 7.726082657 |
| Protein Col4a5 (Fragment) OS = Mus musculus GN = Col4a5 PE = 4 SV = 1 – [F7CK55_MOUSE] | 7.141558716 | 7.11299109 | 7.245885041 |
| Protein Col4a6 OS = Mus musculus GN = Col4a6 PE = 2 SV = 1 – [B1AVK5_MOUSE] | 6.667663539 | 7.041405713 | 0 |
| Protein Col6a3 OS = Mus musculus GN = Col6a3 PE = 4 SV = 1 – [J3QQ16_MOUSE] | 7.182772976 | 6.887860833 | 6.651938048 |
| Protein Krt78 OS = Mus musculus GN = Krt78 PE = 2 SV = 1 – [E9Q0F0_MOUSE] | 7.991649161 | 8.184126545 | 8.640017022 |
| Protein-glutamine gamma-glutamyltransferase 2 OS = Mus musculus GN = Tgm2 PE = 1 SV = 4 – [TGM2_MOUSE] | 6.606623968 | 6.34960286 | 6.828607255 |
| Serotransferrin OS = Mus musculus GN = Tf PE = 1 SV = 1 – [TRFE_MOUSE] | 5.569903604 | 5.983104216 | 0 |
| Serum albumin OS = Mus musculus GN = Alb PE = 1 SV = 3 – [ALBU_MOUSE] | 6.769856217 | 7.211712096 | 6.555648421 |
| Spectrin alpha chain, non-erythrocytic 1 OS = Mus musculus GN = Sptan1 PE = 2 SV = 1 – [A3KGU5_MOUSE] | 6.273962184 | 0 | 0 |
| Spectrin beta chain, non-erythrocytic 1 OS = Mus musculus GN = Sptbn1 PE = 1 SV = 2 – [SPTB2_MOUSE] | 5.993515702 | 0 | 0 |
| Tenascin GRCm38.p3 [GCF_000001635.23] | 7.12532211 | 6.112490357 | 6.730512501 |
| Titin OS = Mus musculus GN = Ttn PE = 2 SV = 1 – [E9Q8K5_MOUSE] | 5.743291257 | 6.295132427 | 0 |
| Tubulin alpha-1C chain OS = Mus musculus GN = Tuba1c PE = 1 SV = 1 – [TBA1C_MOUSE] | 6.33172549 | 5.982744883 | 6.399140301 |
| Tubulointerstitial nephritis antigen-like OS = Mus musculus GN = Tinagl1 PE = 2 SV = 1 – [H3BJ97_MOUSE] | 5.831458484 | 0 | 0 |
| Voltage-dependent anion-selective channel protein 1 OS = Mus musculus GN = Vdac1 PE = 1 SV = 3 – [VDAC1_MOUSE] | 5.666833354 | 5.405315445 | 0 |
| von Willebrand factor OS = Mus musculus GN = Vwf PE = 1 SV = 2 – [VWF_MOUSE] | 5.757768857 | 0 | 0 |

Example 5

Inhibition of MT1-MMP Protects from Tissue Destruction without Modulating the Immune Response MT1-MMP knockout mice suffer from multiple abnormalities and die within 3-5 weeks after birth (Holmbeck et al., 1999); hence, the role of MT1-MMP was evaluated using a selective allosteric inhibitory antibody of MT1-MMP (LEM 2/15) effective at nano-molar concentrations (Udi et al., 2015). Importantly, this antibody has been shown to selectively interact with MT1-MMP expressed on the cell surface and inhibit its collagenase activity without significantly interfering with proMMP-2 activation and enzyme dimerization on the cell surface (Udi et al., 2015). In order to evaluate the role of MT1-MMP during influenza infection, mice were infected with sub-lethal doses of influenza virus and treated with either vehicle (PBS), control antibody or anti-MT1-MMP antibody during the course of the disease (26, 49, 74 hours; FIGS. 4A-K). Representative images are shown from tissue sections at 74 hours post infection in FIGS. 4A-K. AirSEM imaging of hydrated de-cellularized tissues demonstrated that blocking MT1-MMP collagenolytic activity protected tissue integrity (both alveolar and bronchi structures), ECM morphology, and collagen structure as well as the molecular composition of ECM scaffolds (FIG. 4B-E). 3D analysis of two-photon microscopy in second harmonic generation showed that collagen type I fibers were more abundant and maintained a continuous alveolar sac boundaries when infected mice were treated with an anti-MT1-MMP inhibitor (FIG. 4F-G). Furthermore, blocking MT1-MMP proteolytic activity also protected laminin, a major basement-membrane constituent, from degradation in the infected lungs (FIG. 4H-J). Finally, functional in situ zymography indicated significant attenuation of proteolysis following treatment (FIG. 4J-K), suggesting that MT1-MMP is a major driver of tissue destruction in the infection setting.

Figure 11A:
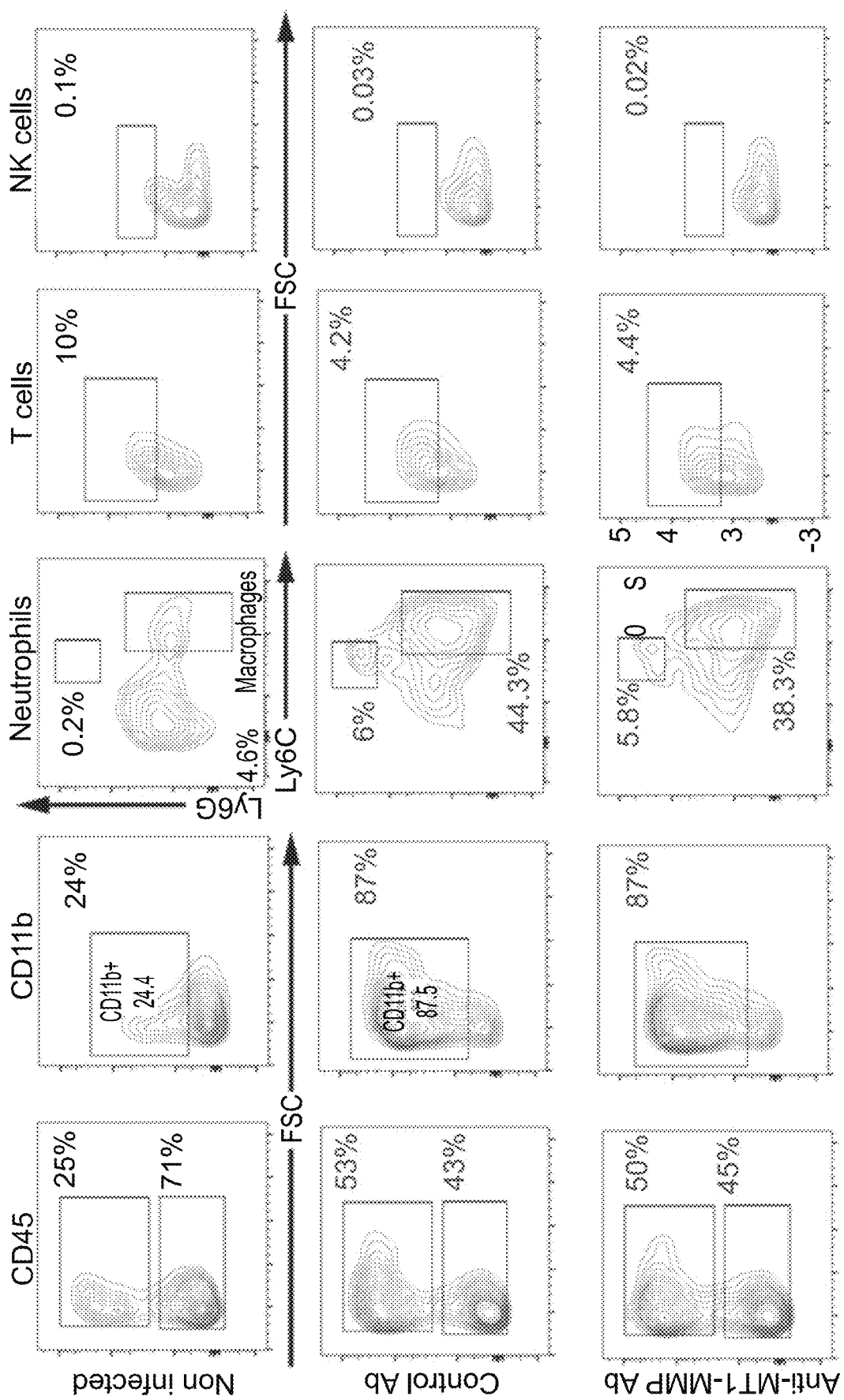

In order to better understand whether MT1-MMP is involved in immune modulation, the abundance of macrophages, neutrophils, lymphocytes and natural killer (NK) cells was analyzed at 74 hours post-infection using either anti-MT1-MMP inhibitor or a control antibody. The results show that there is enhanced recruitment of both macrophages and neutrophils to infected lungs with no detectable differences between anti-MT1-MMP and control-treated animals (FIG. 11A). In addition, in lung tissue sections stained for F4/80 marker, similar macrophage infiltration was observed upon anti-MT1-MMP treatment (FIG. 11B-C). Additionally, broncho-alveolar lavage fluid (BALF) was collected from both anti-MT1-MMP treated as well as control treated mice in order to evaluate cytokine level of major immune-modulating cytokines (IL-1β and TNF-α), which have been shown to play a major role in the infection process (Aldridge et al., 2009; Glaccum et al., 1997; Goldbach-Mansky and Kastner, 2009). Both IL-1β and TNF-α were strongly induced in influenza-infected mice regardless of MT1-MMP activity (FIG. 11D-F), suggesting the immune response was unaffected.

To evaluate whether MT1-MMP activity modulates viral loads during influenza infection, the plaque forming unit (PFU) assay was carried out (FIG. 12A) and also the viral RNA was quantified using PFU assay (FIG. 12B). In addition, lung tissue sections were stained for viral abundance at both 24 and 74 hours post infection (FIG. 12D-F). Overall, these analyses showed minimal effect of MT1-MMP inhibition on viral burden which was limited to the early phases of infection (24 hours); at later stages, no effect was discernible. These results demonstrate that MT1-MMP is not significantly involved in immune modulation or regulation of viral loads; thus, the major MT1-MMP influence on influenza infection is the massive ECM fibrillary protein degradation and tissue damage stemming from its collagenase activity.

Example 6

Figure 13A:
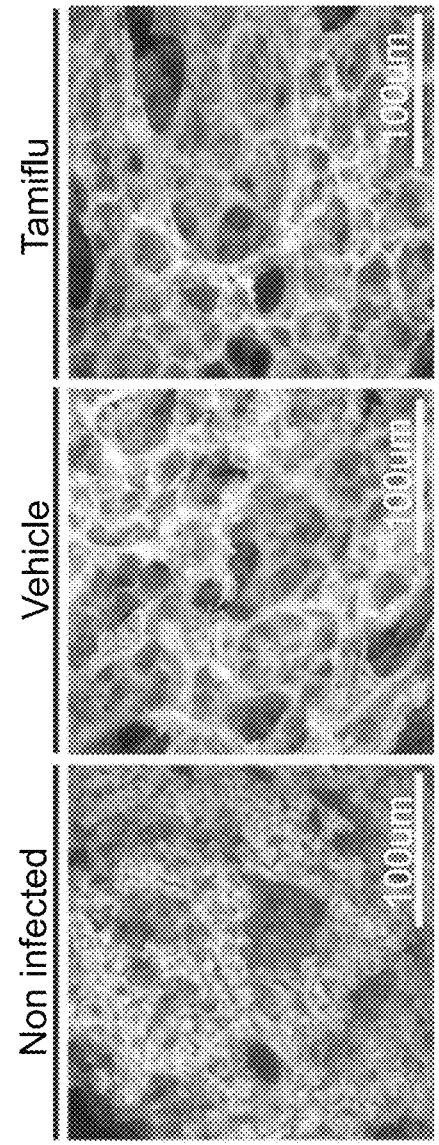
Figure 13D:
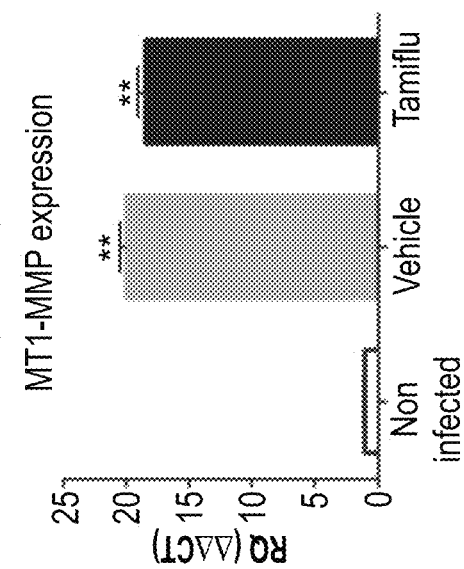
Figure 13C:
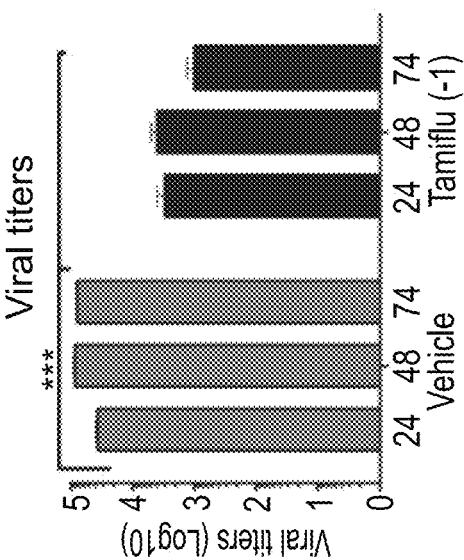
Figure 13B:
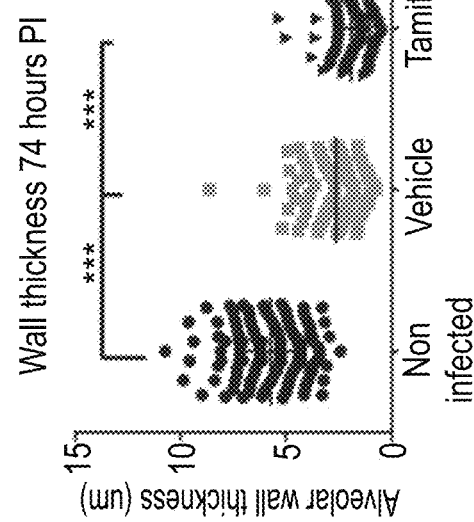

Tissue Damage Results from Host Proteolytic Activity Rather than Viral Cytopathology The present inventors then investigated whether the destructive phenotypes in the lung tissue are a direct consequence of viral cytopathology or rather a result of a host-associated immune response driving the dysregulated ECM proteolysis. The conventional influenza treatment, Oseltamivir phosphate (Tamiflu), a selective inhibitor of influenza A and B viral neuraminidase was analyzed (FIG. 13A-D). Virus titers from whole-lung homogenates of vehicle-treated and Tamiflu-treated mice were quantified using qPCR (FIG. 13C) and compared to topography of lung structural features visualized in lung tissue sections using AirSEM (FIG. 9A-B). Tamiflu dramatically reduces the viral burden (10-100 fold), meaning the tissue is exposed to low but persistent viral presence (FIG. 13C). In spite of the lower viral titers, the same destructive lung tissue and ECM phenotypes were observed, including multifocal alveolar wall thinning and a substantial loss of alveolar cells, in both vehicle-treated and Tamiflu-treated mice (FIG. 13A, B). Such irreversible destruction may be the main cause for loss of barrier integrity, and thus provides a window of opportunity for bacterial invasion. These results prompted the present inventors to test whether protecting ECM integrity via blocking MT1-MMP proteolysis can improve the lethal outcome of influenza-bacteria co-infections.

Example 7

Figure 5A:
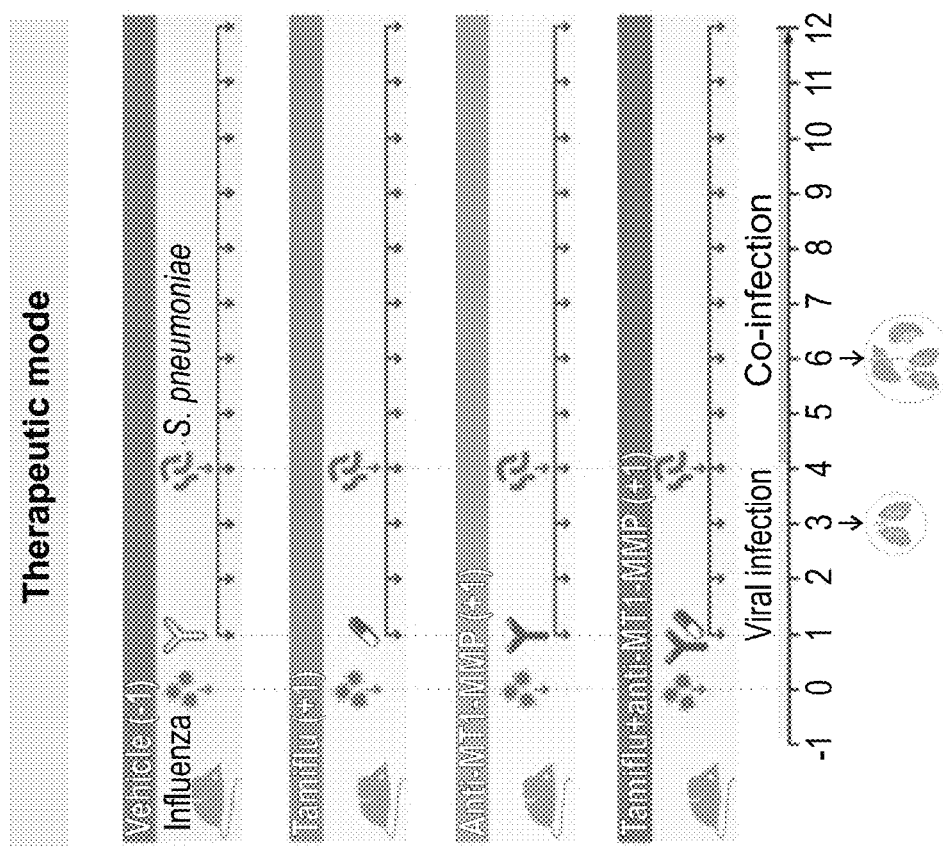
Figure 5D:
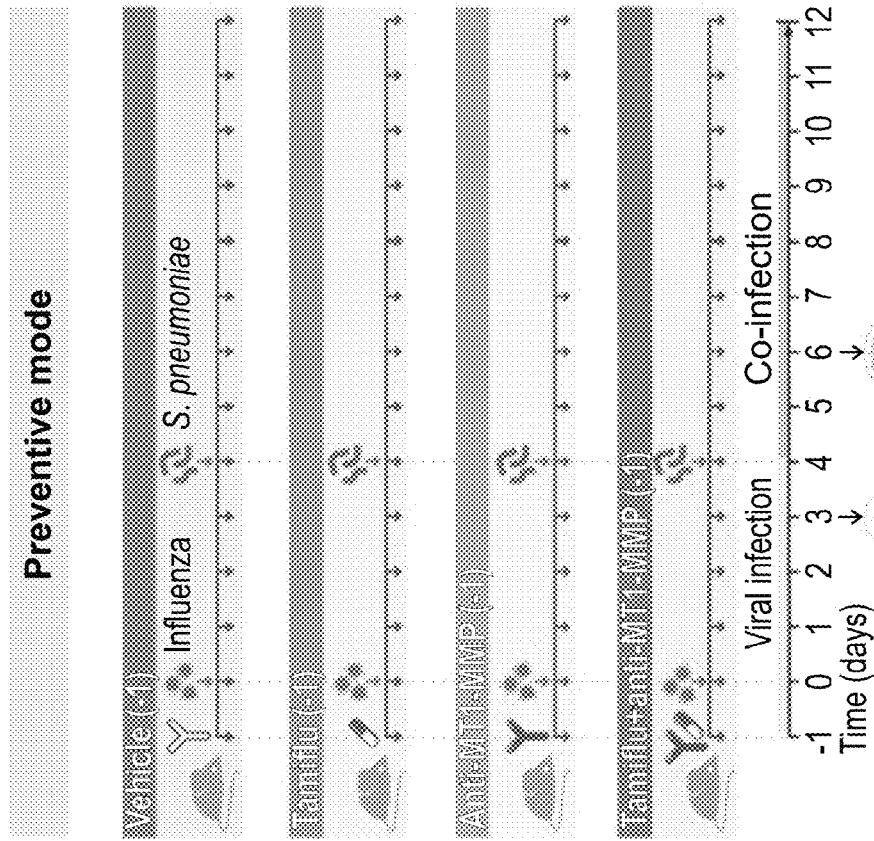

Blocking MT1-MMP in Infected Mice Promotes Tissue Maintenance and Prevents Sepsis As noted above, the viral infection of influenza results in overwhelming damage to the ECM molecular composition and lung structure even with current first-line influenza medication targeting the virus. To further support the physiological consequences of influenza-induced ECM proteolysis and to mimic the frequent conditions that endanger influenza-infected hospitalized patients, an established protocol of influenza secondary bacterial infection using S. pneumoniae was used (McCullers and Herman, 2001; McCullers, 2003; McCullers, 2004). 10 groups of mice (10 mice per group) were infected twice within a range of 96 hours combining PR8 influenza virus followed by S. pneumoniae, with both at sub-lethal doses (FIGS. 5A-H), and the different groups were treated with either vehicle, irrelevant control antibody, Tamiflu, anti-MT1-MMP, or a combined therapy of both agents. To mimic potential treatment modes, mice were treated in two different protocols; prophylactic (before the infection) or therapeutic (post infection) (FIG. 5A-B). The group of mice that was treated with Tamiflu as a preventive agent (Tamiflu-1) exihibited the same survival rates and clinical scores as the group that received anti-MT1-MMP (FIG. 5B-C), suggesting that anti-viral or ECM protection are equally effective in preventing co-infection induced mortality when administered as a preventive treatment.

In line with reports (Jefferson et al., 2014) demonstrating that Tamiflu is not effective in reducing hospitalozation duration or influenza symptoms when administered post-infection, co-infected mice treated with Tamiflu (+1 group) did not exhibit an improved response when compared with the vehicle group (20% survival) (FIG. 5E-F). In these same therapeutic settings (FIG. 5D), treatment with the anti-MT1-MMP inhibitor was significantly better, indicating a pronounced theraputic effect (70% survival). Importantly, combined application of Tamiflu and anti-MT1-MMP treatment resulted in 100% survival rates when used preventatively or therapeutically (FIG. 5B-E). This was further supported by AirSEM images demonstrating the destructive phenotype of alveolar and bronchial structures of the Tamiflu (−1) group, which suggest that even as a prophylactic measure, Tamiflu is ineffective in preventing collateral damage in the lung ECM (FIGS. 14A-B). To extend these observations of ECM fibrillar protein degradation, destruction of basement membrane constituents and disruption of the air-blood barrier in influenza infection, the present inventors further tested for bacterial dissemination into the blood stream (sepsis) and infections in distant organs of co-infected mice. It was found that vehicle-treated mice developed bacteremia and show dissemination of S. pneumoniae into the spleen 2 days post bacterial infection, while mice receiving anti-MT1-MMP inhibitor did not develop systemic bacterial dissemination and maintained a local and confined lung infection (FIG. 5G-H).

DISCUSSION

The present examples suggest that therapeutic strategies to fight influenza infections should be aimed not only at the viral infectivity but also with the purpose of increasing tissue tolerance. This is especially true when taking into consideration that secondary bacterial infections involving S. pneumoniae, Staphylococcus aureus, and Haemophilus influenzae among others that are the main risk factors for reduced survival among high-risk populations (McCullers and Herman, 2001; McCullers, 2014; Morens et al., 2008). Co-infections, in many cases, involve severe lung inflammation driven by robust responses of the immune system to the viral insult. These responses dramatically impair tissue homeostasis, including disruption of the respiratory epithelium, ECM and basement membrane elements. The host response to viral infections includes tissue damage associated with oxidative stress (Avissar et al., 1996; Bozinovski et al., 2012; Campbell et al., 1987; Suliman et al., 2001; Yatmaz et al., 2013). On the one hand, MMP activity is required for the normal immune response to infection. On the other hand, host-derived MMPs may also cause infection-related immunopathology. This paradox results from the delicate balance between normal MMP function and destructive MMP-related host tissue damage (Elkington et al., 2005). Since MMPs play a crucial role in irreversible remodeling of the ECM, these robust proteases are tightly controlled and regulated (Gaffney J, 2015; Lopez-Otin and Matrisian, 2007; Turk, 2006). Moreover, maintaining tissue homeostasis during infection can be challenging when immune cells expressing active proteases are recruited towards respiratory pathogens.

Using genome-wide transcriptional profiling of influenza infected lungs, an extraordinarily large number of genes engaged in extracellular matrix turnover and protein catabolism were observed at various time points during the infection course. Previous studies have assessed the transcriptional signatures during influenza infection by comparing in vitro host responses to different influenza viral strains using human respiratory bronchial and epithelial cell lines as well as in vivo experiments in mice and ferrets (Bortz et al., 2011; Brandes M, 2013; Chevrier et al., 2011; Elkington et al., 2005; Hartmann et al., 2015; Josset et al., 2014; Kash et al., 2004; Leon et al., 2013; Ljungberg et al., 2012; Peng et al., 2014; Shapira et al., 2009). To evaluate the relevance of MT1-MMP to human infections, data from primary human bronchial epithelial cells infected in vitro with a H1N1 influenza strain A/PR/8/34 was analyzed. While human macrophages would be a better model, this data show that MT1-MMP is up-regulated also in a primary human cell model (FIG. 15) (Shapira et al., 2009) suggesting the relevance of our findings to the human ECM remodeling response to influenza infection.

Expanding on these studies, the present inventors focused a systematic analysis on ECM remodeling and, specifically, the activity of MT1-MMP during influenza infection. Noticeably, it was found that MT1-MMP is expressed almost entirely by stromal cells in the healthy lung during homeostasis. In contrast, following infection, MT1-MMP expression is primarily observed in the immune compartment and was accompanied by increased collagenolytic activity. Analysis of MT1-MMP-expressing cell populations showed a robust relationship with cytokine, chemokines and anti-viral response genes confirming that MT1-MMP is an inherent circuit of the host anti-viral response program. It was also found that multiple known substrates of MT1-MMP (Koziol Al, 2012; Stegemann et al., 2013), including fibrillary and basement membrane collagens (colIV, colXII, colXIV) as well as proteoglycans, are irreversibly cleaved and lost from the lungs of influenza-infected mice. These compositional changes were accompanied by ECM scaffold degradation and depletion of epithelial cells, thus contributing to a destructive phenotype that included loss of alveolar space, thinning of the alveolar wall and distortion of airway structures. Together, it has been shown that influenza infections induce expression and activity of MT1-MMP, which contributes to uncontrolled degradation of the structural ECM components that are required for maintaining the lung integrity and function.

Elevated MT1-MMP expression levels have been described in the context of cancer cell metastasis implicating MT1-MMP as an invasive marker associated with advanced stages and poor prognosis (Zarrabi et al., 2011). This property was attributed to the collagenolytic activity of MT1-MMP, degrading the peri-cellular environment and endothelial barriers to make a path for metastatic cells. However, the role of MT1-MMP in influenza infection has not been previously reported. Accordingly, elevated expression levels of tissue inhibitors of metalloproteinases (TIMPs), such as TIMP-1 and TIMP-3, the endogenous inhibitors of most metalloproteinases were noted. Nevertheless, expression levels of TIMP-2 the endogenous inhibitor of MT1-MMP were not significantly changed. Other ECM enzymes have been shown to play a role in influenza infection as well (Bradley et al., 2012). A significant increase in MMP-8 at the protein level was also noted (FIGS. 6A-D).

Previous studies have sought to disentangle viral cytopathic effects from inflammatory collateral damage during influenza infection (Boon et al., 2011; Kash et al., 2004; Kobasa et al., 2007; Tate et al., 2009). It has now been shown that even in low viral titers, lung ECM destruction is significant. This suggests that the main damage to the ECM during infection is a parallel pathway driven by proteolytic events associated with host response irrespective of direct viral loads (Jamieson et al., 2013; Medzhitov et al., 2012; Schneider and Ayres, 2008). Under these conditions, it has now been shown that ECM damage can be almost completely rescued by selectively modulating MT1-MMP proteolytic activity. Using an anti-MT1-MMP inhibitory Fab fragment, it was possible to maintain tissue structure and improve the outcome of influenza infections irrespective of viral replication. It is noteworthy that this MT1-MMP antibody is highly selective in targeting the collagenase activity and does not interfere with enzyme dimerization and maturation of pro-MMP-2 required for tissue homeostasis (Udi et al., 2015). The present study shows that MT1-MMP is not critically involved in immune cell recruitment or IL-1β and TNF-α production. This is in line with previous studies showing that macrophage-derived MT1-MMP regulated subjacent cellular proteolysis rather than directly being involved in migration or cell trafficking through host tissues (Shimizu-Hirota et al., 2012).

In order to mimic the natural disease progression, co-infection settings of influenza and S. pneumoniae were used to show that targeting the virus with Tamiflu alone is ineffective in controlling ECM damage and does not predict successful management of the disease following bacterial infection. Importantly, inhibition of MT1-MMP activity, which protected tissue architecture and composition without significantly affecting the viral loads, exhibited improved disease management when administrated as either a prophylactic or therapeutic agent. In agreement, mice treated with Tamiflu developed sepsis due to dissemination of bacteria from the lungs to the systemic circulation, while those treated with the MT1-MMP inhibitory antibody exhibited reduced spread of bacteria through blood-air disruption. This further suggests that the maintenance of tissue homeostasis is a parallel process that, at least in our influenza model, is as important therapeutically as controlling the viral load. Importantly, the combination of the two treatments achieved complete survival rates both in the prophylactic and therapeutic modes. This further supports the present findings that the combination of the two strategies, targeting viral replication as well as maintaining host barrier homeostasis and preventing tissue destruction, greatly increases the survival outcome.

REFERENCES

Achdout, H., Arnon, T. I., Markel, G., Gonen-Gross, T., Katz, G., Lieberman, N., Gazit, R., Joseph, A., Kedar, E., and Mandelboim, O. (2003). Enhanced recognition of human NK receptors after influenza virus infection. J Immunol 171, 915-923.

Aldridge, J. R., Jr., Moseley, C. E., Boltz, D. A., Negovetich, N.J., Reynolds, C., Franks, J., Brown, S. A., Doherty, P. C., Webster, R. G., and Thomas, P. G. (2009). TNF/iNOSproducing dendritic cells are the necessary evil of lethal influenza virus infection. Proc Natl Acad Sci USA 106, 5306-5311.

Allen, I. C., Scull, M. A., Moore, C. B., Holl, E. K., McElvania-TeKippe, E., Taxman, D. J., Guthrie, E. H., Pickles, R. J., and Ting, J. P. (2009). The NLRP3 inflammasome mediates in vivo innate immunity to influenza A virus through recognition of viral RNA. Immunity 30, 556-565.

Altboum, Z., Steuerman, Y., David, E., Barnett-Itzhaki, Z., Valadarsky, L., Keren-Shaul, H., Meningher, T., Mendelson, E., Mandelboim, M., Gat-Viks, I., et al. (2014). Digital cell quantification identifies global immune cell dynamics during influenza infection. Molecular systems biology 10, 720.

Avissar, N., Finkelstein, J. N., Horowitz, S., Willey, J. C., Coy, E., Frampton, M. W., Watkins, R. H., Khullar, P., Xu, Y. L., and Cohen, H. J. (1996). Extracellular glutathione peroxidase in human lung epithelial lining fluid and in lung cells. The American journal of physiology 270, L173-182.

Boon, A. C., Finkelstein, D., Zheng, M., Liao, G., Allard, J., Klumpp, K., Webster, R., Peltz, G., and Webby, R. J. (2011). H5N1 influenza virus pathogenesis in genetically diverse mice is mediated at the level of viral load. mBio 2.

Bortz, E., Westera, L., Maamary, J., Steel, J., Albrecht, R. A., Manicassamy, B., Chase, G., Martinez-Sobrido, L., Schwemmle, M., and Garcia-Sastre, A. (2011). Host- and strain-specific regulation of influenza virus polymerase activity by interacting cellular proteins. mBio 2.

Bozinovski, S., Seow, H. J., Crack, P. J., Anderson, G. P., and Vlahos, R. (2012). Glutathione peroxidase-1 primes proinflammatory cytokine production after LPS challenge in vivo. PloS one 7, e33172.

Bradley, L. M., Douglass, M. F., Chatterjee, D., Akira, S., and Baaten, B. J. (2012). Matrix metalloprotease 9 mediates neutrophil migration into the airways in response to influenza virus-induced toll-like receptor signaling. PLoS pathogens 8, e1002641.

Brandes M, K. F., Kuchen S, Germain R N. (2013). A systems analysis identifies a feedforward inflammatory circuit leading to lethal influenza infection. Cell 3, 197-212.

Brandes, M., Klauschen, F., Kuchen, S., and Germain, R. N. (2013). A systems analysis identifies a feedforward inflammatory circuit leading to lethal influenza infection. Cell 154, 197-212.

Campbell, E. J., Senior, R. M., and Welgus, H. G. (1987). Extracellular matrix injury during lung inflammation. Chest 92, 161-167.

Chevrier, N., Mertins, P., Artyomov, M. N., Shalek, A. K., Iannacone, M., Ciaccio, M. F., Gat-Viks, I., Tonti, E., DeGrace, M. M., Clauser, K. R., et al. (2011). Systematic discovery of TLR signaling components delineates viral-sensing circuits. Cell 147, 853-867.

Elkington, P. T., O'Kane, C. M., and Friedland, J. S. (2005). The paradox of matrix metalloproteinases in infectious disease. Clinical and experimental immunology 142, 12-20.

Gaffney J, S. I., Zehorai E, Sagi I (2015). Multilevel regulation of matrix metalloproteinases in tissue homeostasis indicates their molecular specificity in vivo (Honoken, N.J.: John Wiley & Sons, Inc).

Genis, L., Galvez, B. G., Gonzalo, P., and Arroyo, A. G. (2006). MT1-MMP: Universal or particular player in angiogenesis? Cancer Metast Rev 25, 77-86.

Glaccum, M. B., Stocking, K. L., Charrier, K., Smith, J. L., Willis, C. R., Maliszewski, C., Livingston, D. J., Peschon, J. J., and Morrissey, P. J. (1997). Phenotypic and functional characterization of mice that lack the type I receptor for IL-1. J Immunol 159, 3364-3371.

Goldbach-Mansky, R., and Kastner, D. L. (2009). Autoinflammation: the prominent role of IL-1 in monogenic autoinflammatory diseases and implications for common illnesses. The Journal of allergy and clinical immunology 124, 1141-1149; quiz 1150-1141.

Greenlee, K. J., Werb, Z., and Kheradmand, F. (2007). Matrix metalloproteinases in lung: multiple, multifarious, and multifaceted. Physiological reviews 87, 69-98.

Hartmann, B. M., Thakar, J., Albrecht, R. A., Avey, S., Zaslaysky, E., Marjanovic, N., Chikina, M., Fribourg, M., Hayot, F., Schmolke, M., et al. (2015). Human Dendritic Cell Response Signatures Distinguish 1918, Pandemic, and Seasonal H1N1 Influenza Viruses. Journal of virology 89, 10190-10205.

Hindiyeh, M., Levy, V., Azar, R., Varsano, N., Regev, L., Shalev, Y., Grossman, Z., and Mendelson, E. (2005). Evaluation of a multiplex real-time reverse transcriptase PCR assay for detection and differentiation of influenza viruses A and B during the 2001-2002 influenza season in Israel. Journal of clinical microbiology 43, 589-595.

Holmbeck, K., Bianco, P., Caterina, J., Yamada, S., Kromer, M., Kuznetsov, S. A., Mankani, M., Robey, P. G., Poole, A. R., Pidoux, I., et al. (1999). MT1-MMP-deficient mice develop dwarfism, osteopenia, arthritis, and connective tissue disease due to inadequate collagen turnover. Cell 99, 81-92.

Jaitin, D. A., Kenigsberg, E., Keren-Shaul, H., Elefant, N., Paul, F., Zaretsky, I., Mildner, A., Cohen, N., Jung, S., Tanay, A., et al. (2014). Massively parallel single-cell RNA-seq for marker-free decomposition of tissues into cell types. Science 343, 776-779.

Jamieson, A. M., Pasman, L., Yu, S., Gamradt, P., Homer, R. J., Decker, T., and Medzhitov, R. (2013). Role of tissue protection in lethal respiratory viral-bacterial coinfection. Science 340, 1230-1234.

Jefferson, T., Jones, M., Doshi, P., Spencer, E. A., Onakpoya, I., and Heneghan, C. J. (2014). Oseltamivir for influenza in adults and children: systematic review of clinical study reports and summary of regulatory comments. BMJ 348, g2545.

Josset, L., Zeng, H., Kelly, S. M., Tumpey, T. M., and Katze, M. G. (2014). Transcriptomic characterization of the novel avian-origin influenza A (H7N9) virus: specific host response and responses intermediate between avian (H5N1 and H7N7) and human (H3N2) viruses and implications for treatment options. mBio 5, e01102-01113.

Kash, J. C., Basler, C. F., Garcia-Sastre, A., Carter, V., Billharz, R., Swayne, D. E., Przygodzki, R. M., Taubenberger, J. K., Katze, M. G., and Tumpey, T. M. (2004). Global host immune response: pathogenesis and transcriptional profiling of type A influenza viruses expressing the hemagglutinin and neuraminidase genes from the 1918 pandemic virus. J Virol 78, 9499-9511.

Kobasa, D., Jones, S. M., Shinya, K., Kash, J. C., Copps, J., Ebihara, H., Hatta, Y., Kim, J. H., Halfmann, P., Hatta, M., et al. (2007). Aberrant innate immune response in lethal infection of macaques with the 1918 influenza virus. Nature 445, 319-323.

Koziol AI, M.-A. M., Clemente C, Gonzalo P, Arroyo A G. (2012). Site-specific cellular functions of MT1-MMP. Eur J Cell Biol 91, 889-895.

Koziol, A., Martin-Alonso, M., Clemente, C., Gonzalo, P., and Arroyo, A. G. (2012). Site-specific cellular functions of MT1-MMP. European journal of cell biology 91, 889-895.

Lavin, Y., Winter, D., Blecher-Gonen, R., David, E., Keren-Shaul, H., Merad, M., Jung, S., and Amit, I. (2014). Tissue-resident macrophage enhancer landscapes are shaped by the local microenvironment. Cell 159, 1312-1326.

Leon, A. J., Banner, D., Xu, L. L., Ran, L. S., Peng, Z. Y., Yi, K., Chen, C., Xu, F. P., Huang, J. R., Zhao, Z., et al. (2013). Sequencing, Annotation, and Characterization of the Influenza Ferret Infectome. Journal of virology 87, 1957-1966.

Lin, K. L., Suzuki, Y., Nakano, H., Ramsburg, E., and Gunn, M. D. (2008). CCR2+ monocyte-derived dendritic cells and exudate macrophages produce influenza-induced pulmonary immune pathology and mortality. J Immunol 180, 2562-2572.

Ljungberg, K., McBrayer, A., Camp, J. V., Chu, Y. K., Tapp, R., Noah, D. L., Grimes, S., Proctor, M. L., Liljestrom, P., Jonsson, C. B., et al. (2012). Host Gene Expression Signatures Discriminate between Ferrets Infected with Genetically Similar H1N1 Strains. PloS one 7.

Lopez-Otin, C., and Matrisian, L. M. (2007). Emerging roles of proteases in tumour suppression. Nature reviews Cancer 7, 800-808.

Lopez-Otin, C., and Overall, C. M. (2002). Protease degradomics: a new challenge for proteomics. Nature reviews Molecular cell biology 3, 509-519.

Lu, P., Takai, K., Weaver, V. M., and Werb, Z. (2011). Extracellular matrix degradation and remodeling in development and disease. Cold Spring Harb Perspect Biol 3.

McCullers, D. L., and Herman, J. P. (2001). Adrenocorticosteroid receptor blockade and excitotoxic challenge regulate adrenocorticosteroid receptor mRNA levels in hippocampus. Journal of neuroscience research 64, 277-283.

McCullers, J., Bartmess, K C (2003). Role of neuraminidase in lethal synergism between influenza virus and *Streptococcus pneumoniae*. J Infect Dis 187, 1000-1009.

McCullers, J. A. (2004). Effect of antiviral treatment on the outcome of secondary bacterial pneumonia after influenza. The Journal of infectious diseases 190, 519-526.

McCullers, J. A. (2006). Insights into the interaction between influenza virus and pneumococcus. Clinical microbiology reviews 19, 571-582.

McCullers, J. A. (2014). The co-pathogenesis of influenza viruses with bacteria in the lung. Nature reviews Microbiology 12, 252-262.

McCullers, J. A., and Rehg, J. E. (2002). Lethal synergism between influenza virus and *Streptococcus pneumoniae*: characterization of a mouse model and the role of platelet-activating factor receptor. The Journal of infectious diseases 186, 341-350.

McQuibban, G. A., Gong, J. H., Tam, E. M., McCulloch, C. A., Clark-Lewis, I., and Overall, C. M. (2000). Inflammation dampened by gelatinase A cleavage of monocyte chemoattractant protein-3. Science 289, 1202-1206.

Medzhitov, R., Schneider, D. S., and Soares, M. P. (2012). Disease tolerance as a defense strategy. Science 335, 936-941.

Morens, D. M., Taubenberger, J. K., and Fauci, A. S. (2008). Predominant role of bacterial pneumonia as a cause of death in pandemic influenza: implications for pandemic influenza preparedness. The Journal of infectious diseases 198, 962-970.

Morrison, C. J., Butler, G. S., Rodriguez, D., and Overall, C. M. (2009). Matrix metalloproteinase proteomics: substrates, targets, and therapy. Curr Opin Cell Biol 21, 645-653.

Newby, A. C. (2008). Metalloproteinase expression in monocytes and macrophages and its relationship to atherosclerotic plaque instability. Arteriosclerosis, thrombosis, and vascular biology 28, 2108-2114.

Noel, A., Gutierrez-Fernandez, A., Sounni, N. E., Behrendt, N., Maquoi, E., Lund, I. K., Cal, S., Hoyer-Hansen, G., and Lopez-Otin, C. (2012). New and paradoxical roles of matrix metalloproteinases in the tumor microenvironment. Frontiers in pharmacology 3, 140.

Ogunniyi, A. D., Giammarinaro, P., and Paton, J. C. (2002). The genes encoding virulence-associated proteins and the capsule of *Streptococcus pneumoniae* are up-regulated and differentially expressed in vivo. Microbiology 148, 2045-2053.

Overall, C. M. (2002). Molecular determinants of metalloproteinase substrate specificity: matrix metalloproteinase substrate binding domains, modules, and exosites. Mol Biotechnol 22, 51-86.

Parks, W. C., and Shapiro, S. D. (2001). Matrix metalloproteinases in lung biology. Respiratory research 2, 10-19.

Peltola, V. T., and McCullers, J. A. (2004). Respiratory viruses predisposing to bacterial infections: role of neuraminidase. The Pediatric infectious disease journal 23, S87-97.

Peng, X., Alfoldi, J., Gori, K., Eisfeld, A. J., Tyler, S. R., Tisoncik-Go, J., Brawand, D., Law, G. L., Skunca, N., Hatta, M., et al. (2014). The draft genome sequence of the ferret (*Mustela putorius* furo) facilitates study of human respiratory disease. Nat Biotechnol 32, 1250-U1114.

Read, A. F., Graham, A. L., and Raberg, L. (2008). Animal Defenses against Infectious Agents: Is Damage Control More Important Than Pathogen Control? Plos Biol 6, 2638-2641.

Schneider, D. S., and Ayres, J. S. (2008). Two ways to survive infection: what resistance and tolerance can teach us about treating infectious diseases. Nature reviews Immunology 8, 889-895.

Sela-Passwell, N., Kikkeri, R., Dym, O., Rozenberg, H., Margalit, R., Arad-Yellin, R., Eisenstein, M., Brenner, O., Shoham, T., Danon, T., et al. (2012). Antibodies targeting the catalytic zinc complex of activated matrix metalloproteinases show therapeutic potential. Nature medicine 18, 143-147.

Shapira, S. D., Gat-Viks, I., Shum, B. O., Dricot, A., de Grace, M. M., Wu, L., Gupta, P. B., Hao, T., Silver, S. J., Root, D. E., et al. (2009). A physical and regulatory map of host-influenza interactions reveals pathways in H1N1 infection. Cell 139, 1255-1267.

Shimizu-Hirota, R., Xiong, W., Baxter, B. T., Kunkel, S. L., Maillard, I., Chen, X. W., Sabeh, F., Liu, R., Li, X. Y., and Weiss, S. J. (2012). MT1-MMP regulates the PI3K delta.Mi-2/NuRD-dependent control of macrophage immune function (vol 26, pg 395, 2012). Gene Dev 26, 1122-1122.

Soares, M. P., Gozzelino, R., and Weis, S. (2014). Tissue damage control in disease tolerance. Trends in immunology 35, 483-494.

Solomonov, I., Talmi-Frank, D., Milstein, Y., Addadi, S., Aloshin, A., and Sagi, I. (2014). Introduction of correlative light and airSEM microscopy imaging for tissue research under ambient conditions. Scientific reports 4, 5987.

Stegemann, C., Didangelos, A., Barallobre-Barreiro, J., Langley, S. R., Mandal, K., Jahangiri, M., and Mayr, M.

(2013). Proteomic identification of matrix metalloproteinase substrates in the human vasculature. Circulation Cardiovascular genetics 6, 106-117.

Suliman, H. B., Ryan, L. K., Bishop, L., and Folz, R. J. (2001). Prevention of influenza-induced lung injury in mice overexpressing extracellular superoxide dismutase. American journal of physiology Lung cellular and molecular physiology 280, L69-78.

Tate, M. D., Brooks, A. G., and Reading, P. C. (2011). Specific sites of N-linked glycosylation on the hemagglutinin of H1N1 subtype influenza A virus determine sensitivity to inhibitors of the innate immune system and virulence in mice. J Immunol 187, 1884-1894.

Tate, M. D., Deng, Y. M., Jones, J. E., Anderson, G. P., Brooks, A. G., and Reading, P. C. (2009). Neutrophils ameliorate lung injury and the development of severe disease during influenza infection. J Immunol 183, 7441-7450.

Taubenberger, J. K., and Morens, D. M. (2006). 1918 Influenza: the mother of all pandemics. Emerging infectious diseases 12, 15-22.

Teijaro, J. R., Walsh, K. B., Rice, S., Rosen, H., and Oldstone, M. B. (2014). Mapping the innate signaling cascade essential for cytokine storm during influenza virus infection. Proceedings of the National Academy of Sciences of the United States of America 111, 3799-3804.

Thomas, P. G., Dash, P., Aldridge, J. R., Jr., Ellebedy, A. H., Reynolds, C., Funk, A. J., Martin, W. J., Lamkanfi, M., Webby, R. J., Boyd, K. L., et al. (2009). The intracellular sensor NLRP3 mediates key innate and healing responses to influenza A virus via the regulation of caspase-1. Immunity 30, 566-575.

Tumpey, T. M., Garcia-Sastre, A., Taubenberger, J. K., Palese, P., Swayne, D. E., Pantin-Jackwood, M. J., Schultz-Cherry, S., Solorzano, A., Van Rooijen, N., Katz, J. M., et al. (2005). Pathogenicity of influenza viruses with genes from the 1918 pandemic virus: functional roles of alveolar macrophages and neutrophils in limiting virus replication and mortality in mice. Journal of virology 79, 14933-14944.

Turk, B. (2006). Targeting proteases: successes, failures and future prospects. Nature reviews Drug discovery 5, 785-799.

Udi, Y., Grossman, M., Solomonov, I., Dym, O., Rozenberg, H., Moreno, V., Cuniasse, P., Dive, V., Arroyo, A. G., and Sagi, I. (2015). Inhibition mechanism of membrane metalloprotease by an exosite-swiveling conformational antibody. Structure 23, 104-115.

Watanabe, T., Kiso, M., Fukuyama, S., Nakajima, N., Imai, M., Yamada, S., Murakami, S., Yamayoshi, S., Iwatsuki-Horimoto, K., Sakoda, Y., et al. (2013). Characterization of H7N9 influenza A viruses isolated from humans. Nature 501, 551-555.

White, M. R., Doss, M., Boland, P., Tecle, T., and Hartshorn, K. L. (2008). Innate immunity to influenza virus: implications for future therapy. Expert review of clinical immunology 4, 497-514.

Yatmaz, S., Seow, H. J., Gualano, R. C., Wong, Z. X., Stambas, J., Selemidis, S., Crack, P. J., Bozinovski, S., Anderson, G. P., and Vlahos, R. (2013). Glutathione peroxidase-1 reduces influenza A virus-induced lung inflammation. American journal of respiratory cell and molecular biology 48, 17-26.

Zarrabi, K., Dufour, A., Li, J., Kuscu, C., Pulkoski-Gross, A., Zhi, J., Hu, Y., Sampson, N. S., Zucker, S., and Cao, J. (2011). Inhibition of matrix metalloproteinase 14 (MMP-14)-mediated cancer cell migration. The Journal of biological chemistry 286, 33167-33177.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a subject infected with a pathogen comprising administering to the subject a therapeutically effective amount of an anti-pathogenic agent directed towards said pathogen and a therapeutically effective amount of an agent which specifically down-regulates membrane type 1-matrix metalloproteinase 1 (MT1-MMP1), thereby treating the subject.

2. A method of treating influenza in a subject in need thereof comprising administering to the subject a therapeutically effective amount of an agent which specifically down-regulates MT1-MMP1.

3. The method of claim 2, wherein the administering is effected no more than 2 days after the start of symptoms of the infection.

4. The method of claim 1, wherein said agent which specifically down-regulates MT1-MMP1 is an antibody.

* * * * *